(12) United States Patent
Manthorpe et al.

(10) Patent No.: US 6,875,748 B2
(45) Date of Patent: Apr. 5, 2005

(54) COMPOSITIONS AND METHODS FOR IN VIVO DELIVERY OF POLYNUCLEOTIDE-BASED THERAPEUTICS

(75) Inventors: Marston Manthorpe, San Diego, CA (US); Jukka Hartikka, San Diego, CA (US); Loretta Sukhu, San Diego, CA (US); Jennifer Meek, San Diego, CA (US)

(73) Assignee: Vical Incorporated, San Diego, CA (US)

( * ) Notice: Subject to any disclaimer, the term of this patent is extended or adjusted under 35 U.S.C. 154(b) by 0 days.

(21) Appl. No.: 09/839,574

(22) Filed: Apr. 23, 2001

(65) Prior Publication Data

US 2002/0019358 A1 Feb. 14, 2002

Related U.S. Application Data

(60) Provisional application No. 60/198,823, filed on Apr. 21, 2000, and provisional application No. 60/253,153, filed on Nov. 28, 2000.

(51) Int. Cl.[7] .............................................. A61K 31/70
(52) U.S. Cl. ..................... 514/44; 536/23.1; 536/23.51; 536/23.52; 536/23.7; 435/320.1; 435/455; 435/458; 435/78.08; 568/624
(58) Field of Search ........................... 514/44; 536/23.1, 536/23.51–23.53, 23.7, 23.5, 23.72, 23.74, 23.2; 435/320.1, 455, 458, 78.08; 568/624; 424/450

(56) References Cited

U.S. PATENT DOCUMENTS 5,264,618 A 11/1993 Felgner et al.
5,459,127 A 10/1995 Felgner et al.
5,470,568 A 11/1995 Lee ............................ 424/78.02

(Continued)

FOREIGN PATENT DOCUMENTS

| AU | 737720 | 8/1998 |
| CA | 2 284 399 | 3/2000 |
| WO | WO 95/10265 A1 | 4/1995 |
| WO | WO 96/21470 | 7/1996 |

(Continued)

OTHER PUBLICATIONS

Norihisa Ishii et al., AIDS Research and Human Retroviruses, vol. 13, No. 16, 1997, pp. 1421–1428.*
Jeffrey B. Ulmer et al., Science, vol. 259, Mar. 19, 1993, pp. 1745–1749.*
No Author Listed, "Nomenclature and the Pluronic® Surfactant Grid," <<http://www.basf.com/static/OpenMarket/Xcelerate/Preview_cid–982931199731_pubid–974236729499_c–Article.html>>, accessed Dec. 16, 2002.

(Continued)

Primary Examiner—Dave T. Nguyen
Assistant Examiner—Richard Schnizer
(74) Attorney, Agent, or Firm—Sterne, Kessler, Goldstein & Fox P.L.L.C.

(57) ABSTRACT

The present invention relates to pharmaceutical compositions and methods to improve expression of exogenous polypeptides into vertebrate cells in vivo, utilizing delivery of polynucleotides encoding such polypeptides. More particularly, the present invention provides the use of salts, in particular sodium and potassium salts of phosphate, in aqueous solution, and auxiliary agents, in particular detergents and surfactants, in pharmaceutical compositions and methods useful for direct polynucleotide-based polypeptide delivery into the cells of vertebrates.

60 Claims, 32 Drawing Sheets

U.S. PATENT DOCUMENTS

| | | | |
|---|---|---|---|
| 5,552,309 A | 9/1996 | March | |
| 5,580,859 A | 12/1996 | Felgner et al. | 514/44 |
| 5,589,466 A | 12/1996 | Felgner et al. | 514/44 |
| 5,641,665 A | 6/1997 | Hobart et al. | |
| 5,656,611 A | 8/1997 | Kabanov et al. | |
| 5,693,622 A | 12/1997 | Wolff et al. | |
| 5,703,055 A | 12/1997 | Felgner et al. | 514/44 |
| 5,855,913 A | 1/1999 | Hanes et al. | 424/489 |
| 5,861,397 A * | 1/1999 | Wheeler | 514/247 |
| 5,883,103 A | 3/1999 | Burnside et al. | 514/262 |
| 5,885,590 A | 3/1999 | Hunter et al. | 424/280.1 |
| 5,897,876 A | 4/1999 | Rudnic et al. | 424/455 |
| 5,910,488 A | 6/1999 | Nabel et al. | |
| 5,952,004 A | 9/1999 | Rudnic et al. | 424/455 |
| 5,962,428 A | 10/1999 | Carrano et al. | 514/44 |
| 5,985,309 A | 11/1999 | Edwards et al. | 424/426 |
| 5,994,314 A | 11/1999 | Eljamal et al. | 514/44 |
| 5,994,317 A | 11/1999 | Wheeler | |
| 6,022,874 A | 2/2000 | Wheeler | |
| 6,040,295 A | 3/2000 | Rolland et al. | |
| 6,086,899 A | 7/2000 | Balasubramanian et al. | |
| 6,120,794 A * | 9/2000 | Liu et al. | 424/450 |
| 6,147,055 A | 11/2000 | Hobart et al. | |
| 6,149,922 A | 11/2000 | Balasubramanian et al. | |
| 6,214,804 B1 | 4/2001 | Felgner et al. | 514/44 |
| 6,221,959 B1 | 4/2001 | Kabanov et al. | |
| 6,228,844 B1 | 5/2001 | Wolff et al. | |
| 6,353,055 B1 | 3/2002 | Kabanov et al. | |
| 6,359,054 B1 | 3/2002 | Lemieux et al. | |
| 6,399,588 B1 | 6/2002 | Hobart et al. | |
| 6,416,947 B1 | 7/2002 | Balasubramanian et al. | |
| 6,440,743 B1 | 8/2002 | Kabanov et al. | |
| 6,586,409 B1 | 7/2003 | Wheeler | |
| 6,670,332 B1 | 12/2003 | Wheeler | |
| 6,696,424 B1 | 2/2004 | Wheeler | |
| 2003/0032615 A1 | 2/2003 | Fegner et al. | |
| 2003/0186913 A1 | 10/2003 | Wolff et al. | |
| 2003/0191082 A1 | 10/2003 | Wheeler | |
| 2003/0203863 A1 | 10/2003 | Hobart et al. | |
| 2004/0157789 A1 | 8/2004 | Geall | |

FOREIGN PATENT DOCUMENTS

| | | |
|---|---|---|
| WO | WO 97/30731 | 8/1997 |
| WO | WO 99/26663 A2 | 6/1999 |
| WO | WO 99/31262 A2 | 6/1999 |
| WO | WO 99/64615 A1 | 12/1999 |
| WO | WO 00/57917 * | 3/2000 |
| WO | WO 00/40273 A3 | 7/2000 |
| WO | WO 00/40273 A2 | 7/2000 |
| WO | WO 01/09303 | 2/2001 |
| WO | WO 01/65911 A2 | 9/2001 |
| WO | WO 01/83698 A2 | 11/2001 |
| WO | WO 01/87234 A2 | 11/2001 |
| WO | WO 02/00844 A2 | 1/2002 |

OTHER PUBLICATIONS

Schmolka, I.R., "A Review of Block Polymer Surfactants," *J. Am. Oil Chem. Soc. 54*:110–116, The American Oil Chemist's Society (1977).

Adams–Graves et al., "RheothRx (poloxamer 188) injection for the acute painful episode of sickle cell disease: a pilot study," *Blood 90*:2041–2046, American Society for Hematology, W. B. Saunders Co. (1997).

Anwer, K. et al., "Synergistic effect of formulated plasmid and needle–free injection for genetic vaccines," *Pharm. Res. 16*:889–895, American Associated of Pharmaceutical Scientists (Jun. 1999).

Baranov, A. et al., "Local and distant transfection of mdx muscle fibers with dystrophin and LacZ genes delivered in vivo by synthetic microspheres," *Gene Ther. 6*:1406–1414, Stockton Press (Aug. 1999).

Bertling, W.M. et al., "Use of liposomes, viral capsids, and nanoparticle as DNA carriers," *Biotechnol. Appl. Biochm. 13*:390–405, Portland Press Limited (1991).

Boussif, O. et al., "A versatile vector for gene and oligonucleotide transfer into cells in culture and in vivo: polyethylenimine," *Proc. Natl. Acad. Sci. USA 92*:7297–7301, National Academy of Sciences (1995).

Cho, C.–W. et al., "Improvement of receptor–mediated gene delivery to HepG2 cells using an amphiphilic gelling agent," *Biotechnol. Appl. Biochem. 32*:21–26, Portland Press Limited (Aug. 2000).

Doh, S.G. et al., "Spatial–temporal patterns of gene expression in mouse skeletal muscle after injection of lacZ plasmid DNA," *Gene Ther. 4*:648–663, Stockton Press (1997).

Freeman, D.J. and Niven, R.W., "The influence of sodium glycocholate and other additives on the in vivo transfection of plasmid DNA in the lungs," *Pharm. Res. 13*:202–209, American Association of Pharmaceutical Scientists (1996).

Kariko, K. et al., "Phosphate–enhanced transfection of cationic lipid–complexed mRNA and plasmid DNA," *Biochim. Biophys. Acta. 1369*:320–334, Elsevier Science Ltd. (1998).

Kichler, A. et al., "Influence of the DNA complexation medium on the transfection efficiency of lipospermine/DNA particles," *Gene Ther. 5*:855–860, Stockton Press (1998).

Lee, R. et al., "Surfactant–induced sealing of electropermeabilized skeletal muscle membranes in vivo," *Proc. Natl. Acad. Sci. U.S.A. 89*:4524–4528, National Academy of Sciences (1992).

Lemieux, P. et al., "A Combination of Poloxamers Increases and Prolongs Gene Expression of Plasmid DNA in Skeletal Muscle," Abstracts Presented at the Seventh Meeting of the European Society of Gene Therapy. Munich, Germany, Nov. 26–28 1999.

Lemieux, P. et al., "A combination of poloxamers increases gene expression of plasmid DNA in skeletal muscle," *Gene Ther. 7*:986–991, Stockton Press (Jun. 2000).

Leong, K.W. et al., "DNA–polycation nanospheres as non-viral gene delivery vehicles," *J. Control. Release 53*:183–93, Elsevier Science B.V. (1998).

Liu, F. et al., "Effect of Non–Ionic Surfactants on the Formation of DNA/Emulsion Complexes and EmulsionMediated Gene Transfer," *Pharmaceutical Research 13*:1642–1646, Plenum Publishing Corporation (1996).

Lunsford, L. et al., "Tissue distribution and persistence in mice of plasmid DNA encapsulated in a PLGA–based microsphere delivery vehicle," *J. Drug Target. 8*:39–50, Gordon and Breach Publishing Group (Nov. 2000).

Mumper, R.J. et al., "Protective interactive noncondensing (PINC) polymers for enhanced plasmid distribution and expression in rat skeletal muscle," *J. Control. Release 52*:191–203, Elsevier Science B.V. (1998).

Mumper, R.J et al., "Polyvinyl derivatives as novel interactive polymers for controlled gene delivery to muscle," *Pharm. Res. 13*:701–709, American Association of Pharmaceutical Scientists (1996).

O'Keefe et al., "Poloxamer–188 as an adjunct to primary percutaneous transluminal coronary angioplasty for actute myocardial infarction," *Am. J. Cardiol. 78*:747–750, Elsevier Science Ltd. (1996).

Orson, F.M. et al., "Genetic immunization with lung–targeting macroaggregated polyethyleneimine–albumin conjugates elicits combined systemic and mucosal immune responses," *J. Immunol. 164:*6313–6321, American Association of Immunologists (Jun. 2000).

Raczka, E. et al., "The effect of synthetic surfactant Exosurf on gene transfer in mouse lung in vivo," *Gene Ther. 5:*1333–1339, Stockton Press (1998).

Sawa, T. et al., "Intraluminal water increases expression of plasmid DNA in rat lung," *Hum. Gene. Ther. 7:*933–941, Mary Ann Liebert, Inc. (1996).

Shi, N.Y. et al., "Noninvasive gene targeting to the brain," *Proc. Natl. Acad. Sci. USA 97:*7567–7572, National Academy of Sciences (Jun. 2000).

Turunen, M.P. et al., "Efficient adventitial gene delivery to rabbit carotid artery with cationic polymer–plasmid complexes," *Gene Ther. 6:*6–11, Stockton Press (Jan. 1999).

Wells, D.J. et al., "Evaluation of Plasmid DNA for in Vivo Gene Therapy: Factors Affecting the Number of Transfected Fibers," *Journal of Pharmaceutical Sciences 87:*763–768, American Chemical Society and American Pharmaceutical Association (1998).

Wheeler, C.J. et al., "A novel cationic lipid greatly enhances plasmid DNA delivery and expression in mouse lung," *Proc. Natl. Acad. Sci. USA 93:*11454–11459, National Academy of Sciences (1996).

Danko, I. et al., "Pharmacological enhancement of in vivo foreign gene expression in muscle," *Gene Ther. 1:*114–121, Macmillan Press (1994).

Davis, H.L. et al., "Direct Gene Transfer into Skeletal Muscle In Vivo: Factors Affecting Efficiency of Transfer and Stability of Expression," *Hum. Gene Ther. 4:*151–159, Mary Ann Liebert, Inc. (1993).

Hartikka, J. et al., "An Improved Plasmid DNA Expression Vector for Direct Injection into Skeletal Muscle," *Hum. Gene Ther. 7:*1205–1217, Mary Ann Liebert, Inc. (1996).

Hartikka, J. et al., "*Sodium phosphate enhances plasmid DNA expression in vivo,*" *Gene Ther. 7:*1171–1182, Macmillan Publishers Ltd. (Jul. 2000).

Nguyen, H.–K. et al., "Evaluation of polyether–polyethyleneimine graft copolymers as gene transfer agents," *Gene Ther. 7:*126–138, Macmillan Publishers Ltd. (Jan. 2000).

Copy of Co–Pending U.S. Appl. No. 10/725,015, Geall et al., filed Dec. 2, 2003.

Copy of Co–Pending U.S. Appl. No. 10/748,853, Wheeler, C.J., filed Dec. 30, 2003.

\* cited by examiner

| PLASMID NAME | GENE | PARENTAL PLASMID | PROMOTOR/ ENHANCER | TERMINATOR |
|---|---|---|---|---|
| VR1223 | FIREFLY LUX | VR1012* | CMV | BGH |
| VR1412 | BACTERIAL LACZ | VR1012* | CMV | BGH |
| VR2901 | MOUSE EPO | VR1012* | CMV | BGH |
| VR2996 | MOUSE EPO | VR1012 | MV/Desmin | BGH |
| VR3301 | HUMAN SEAP | VR1012* | CMV | BGH |
| VR3502 | RAT PROINSULIN | VR1012* | CMV | BGH |
| VR4151 | HUMAN IFN-OMEGA | VR1055 | CMV | mRBG |
| VR4700 | INFLUENZA NP | VR1255** | CMV | mRBG |
| VR1418 | BACTERIAL LACZ | VR1043 | RSV | BGH |
| VR1255 | FIREFLY LUX | VR1223 | CMV | mRBG |

INTERMEDIATE PLASMIDS

| PLASMID NAME | GENE | PARENTAL PLASMID | PROMOTOR/ ENHANCER | TERMINATOR |
|---|---|---|---|---|
| VR1012 | NONE | V1J*** | CMV | BGH |
| VR1043 | NONE | VR1343 | RSV | BGH |
| VR1055 | NONE | VR1255 | CMV | mRBG |

FIG.1

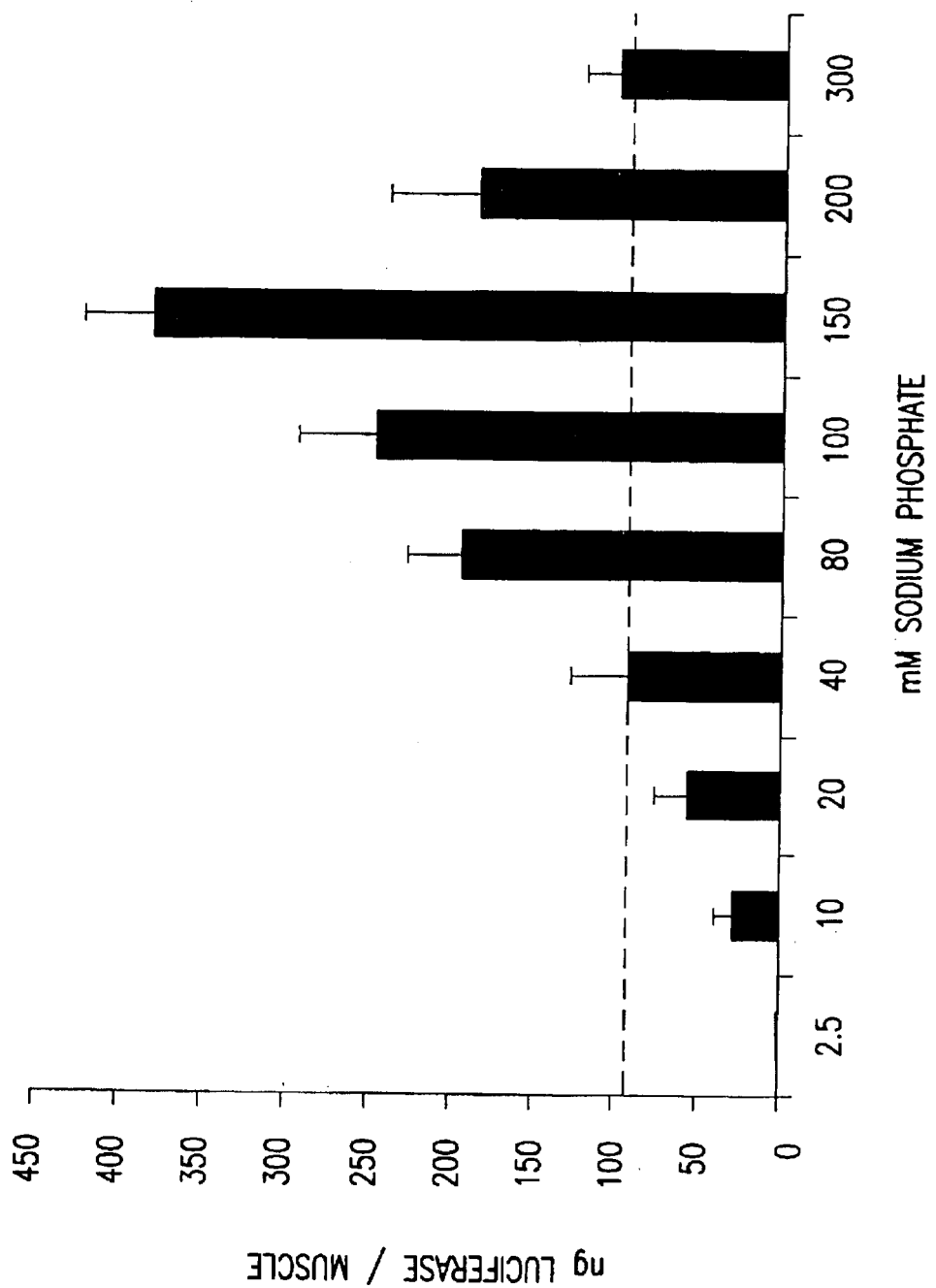

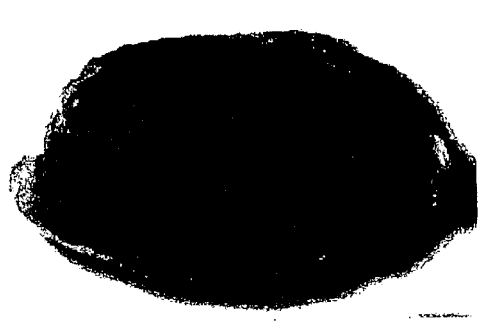
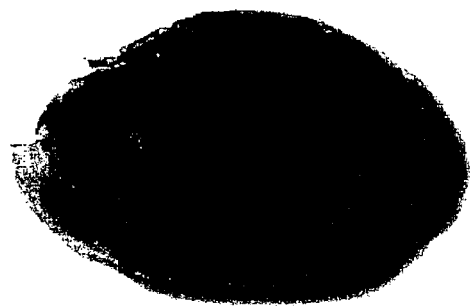
FIG.6A          FIG.6B
FIG.6C          FIG.6D
FIG.6E          FIG.6F

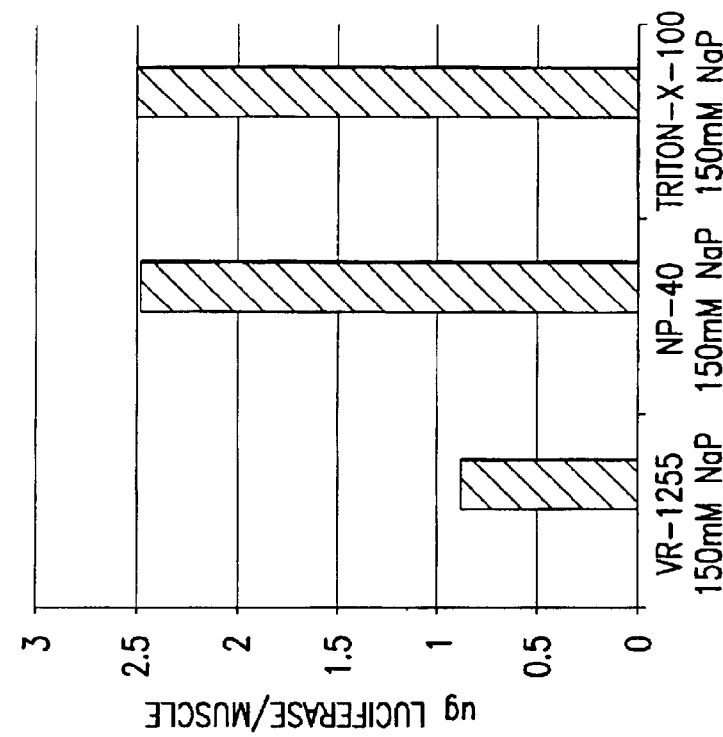
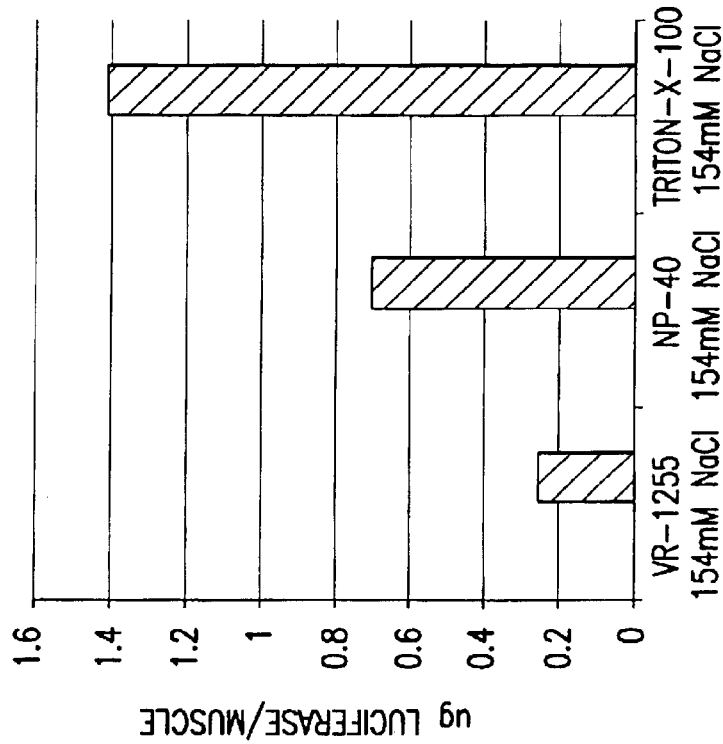
FIG. 9

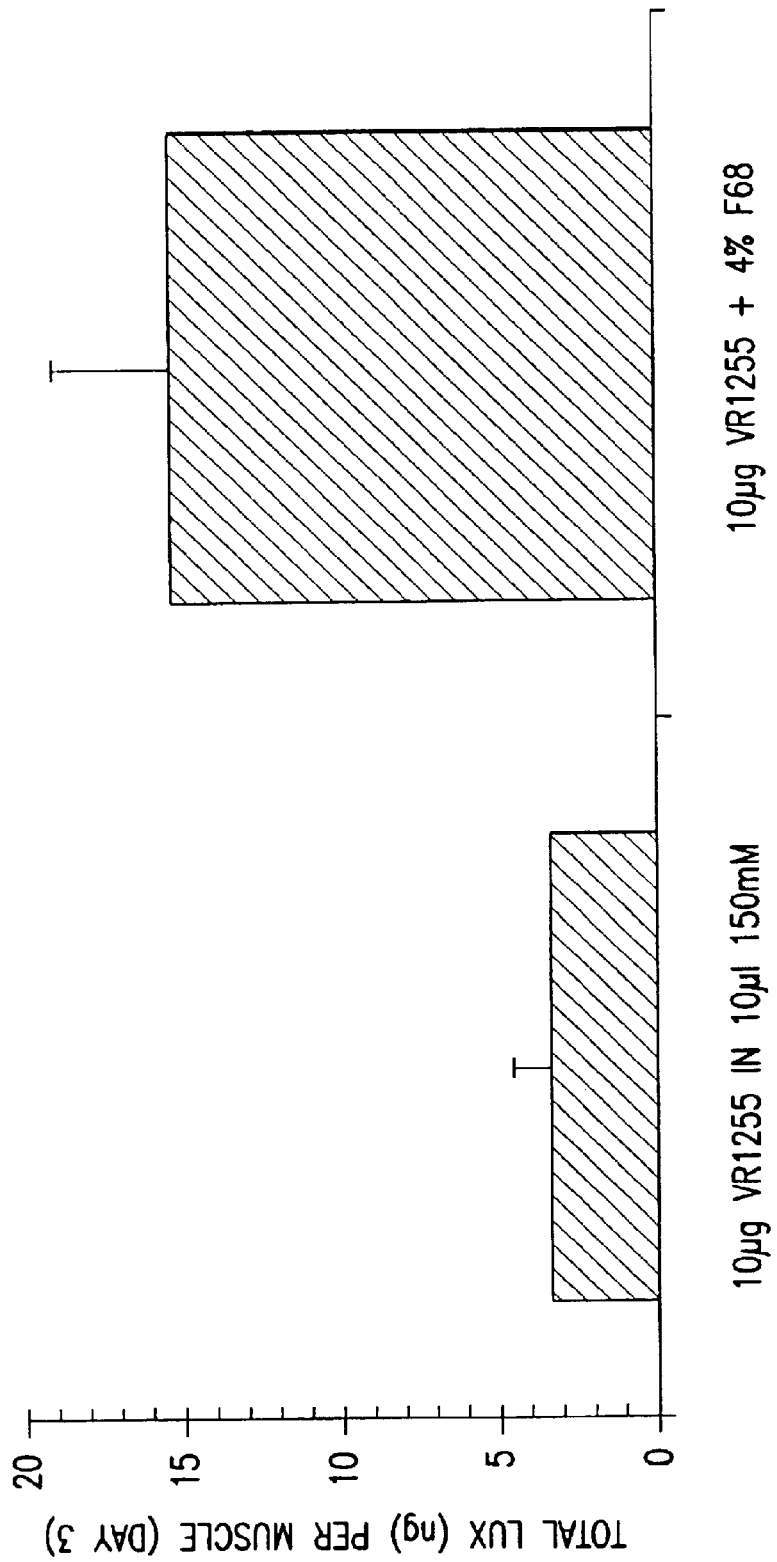

COMPOSITIONS AND METHODS FOR IN VIVO DELIVERY OF POLYNUCLEOTIDE-BASED THERAPEUTICS

CROSS-REFERENCE TO RELATED APPLICATIONS

This application claims benefit of U.S. Provisional Application No. 60/198,823, filed Apr. 21, 2000, and U.S. Provisional Application No. 60/253,153, filed Nov. 28, 2000.

STATEMENT REGARDING FEDERALLY FUNDED RESEARCH AND DEVELOPMENT

Not Applicable.

Not applicable.

BACKGROUND OF THE INVENTION

1. Field of the Invention

The present invention relates generally to compositions and methods useful for in vivo polynucleotide-based polypeptide delivery into cells of vertebrates. More particularly, the present invention provides the use of salts and/or auxiliary agents in compositions and methods useful for direct polynucleotide-based polypeptide delivery into the cells of vertebrates.

2. Related Art

The in vivo delivery of a polynucleotide (e.g., plasmid DNA) into vertebrate tissues has been shown to result in the cellular uptake and expression of the polynucleotide into a desired polypeptide (Wolff, J. A. et al., *Science* 247:1465–1468 (1990); Wheeler, C. J. et al., *Proc. Natl. Acad. Sci.* USA 93:11454–11459 (1996)). Potential human therapeutic uses of such polynucleotide-based polypeptide delivery include immune response induction and modulation, therapeutic polypeptide delivery, and amelioration of genetic defects. For example, a polynucleotide may encode an antigen that induces an immune response against an infectious pathogen or against tumor cells (Restifo, N. P. et al., *Folia Biol.* 40:74–88 (1994); Ulmer, J. B. et al., *Ann. NY Acad. Sci.* 772:117–125 (1995); Horton, H. M. et al., *Proc. Natl. Acad. Sci. USA* 96:1553–1558 (1999); Yagi, K. et al., *Hum. Gene Ther.* 10: 1975–1982 (1999)). The polynucleotide may encode an immunomodulatory polypeptide, e.g., a cytokine, that diminishes an immune response against self antigens or modifies the immune response to foreign antigens, allergens, or transplanted tissues (Qin, L. et al., *Ann. Surg.* 220:508–518 (1994); Dalesandro, J. et al., *J. Thorac. Cardiovasc. Surg.* 111: 416–421 (1996); Moffatt, M. and Cookson, W., *Nat. Med.* 2:515–516 (1996); Ragno, S. et al., *Arth. and Rheum.* 40:277–283 (1997); Dow, S. W. et al., *Hum. Gene Ther.* 10:1905–1914 (1999); Piccirillo, C. A. et al., *J. Immunol.* 161:3950–3956 (1998); Piccirillo, C. A. and Prud'homme, G. J., *Hum. Gene Ther.* 10: 915–1922 (1999)). For therapeutic polypeptide delivery, the polynucleotide may encode, for example, an angiogenic protein, hormone, growth factor, or enzyme (Levy, M. Y. et al., *Gene Ther.* 3:201–211 (1996); Tripathy, S. K. et al., *Proc. Natl. Acad. Sci. USA* 93:10876–10880 (1996); Tsurumi, Y. et al., *Circulation* 94:3281–3290 (1996); Novo, F. J. et al., *Gene Ther.* 4:488–492 (1997); Baumgartner, I. et al., *Circulation* 97:1114–1123 (1998); Mir, L. M. et al., *Proc. Natl. Acad. Sci. USA* 96:4262–4267 (1999)). For amelioration of genetic defects, the polynucleotide may encode normal copies of defective proteins such as dystrophin or cystic fibrosis transmembrane conductance regulator (Danko, I. et al., *Hum. Mol. Genet.* 2:2055–2061 (1993); Cheng, S. H. and Scheule, R. K., *Adv. Drug Deliv. Rev.* 30:173–184 (1998)).

However, the efficiency of a polynucleotide uptake and expression, especially when the polynucleotide is not associated with infectious agents, is relatively low. For example, Doh, S. G. et al., *Gene Ther.* 4:648–663 (1997) report that the administration of plasmid DNA into mouse muscle results in the detectable transduction of an average of only 6%, i.e., about 234 out of approximately 4000 of the myofibers in the injected muscle. Also notable is that of the myofibers transfected, the actual number of transfected nuclei is presumed to be a small proportion.

Wheeler, C. J. et al., ibid., show that administration of plasmid DNA complexed with cationic lipid into a mouse lung results in the transduction of less than 1% of the lung cells.

Attempts have been made to increase the efficiency of in vivo polynucleotide administration into vertebrates using chemical agents or physical manipulations. Such chemical agents include cellular toxins such as bupivacaine, cardiotoxin or barium chloride (Wells, D. J., *FEBS Letters* 332:179–182 (1993); Vitadello, M. et al., *Hum. Gene. Ther.* 5:11–18 (1994); Danko, I., et al., *Hum. Mol. Genet.* 2:2055–2061 (1993); Fomsgaard, et al., *Apmis* 106:636–646 (1998); Fomsgaard, A., *Immunol. Lett.* 65:127–131 (1999)) which act to cause muscle damage followed by muscle regeneration by cell division which makes the cells more receptive to DNA entry (Thomason, D. B. and Booth, F. W., *Am. J. Physiol.* 258:C578–581 (1990)); polymers such as polyvinyl pyrolidone, polyvinyl alcohol, polyethyleneimine, polyamidomine, and polyethylene glycol-polyethyleneimine-transferrin complexes that coat the DNA and protect it from DNases and enhance plasmid DNA-based expression or immune responses (Mumper, R. J., et al., *Pharm. Res.* 13:701–709 (1996); Mumper R. J., et al., *J. Cont. Rel.* 52:191–203 (1998); Anwer, K., et al., *Pharm. Res*, 16:889–895 (1999); Boussif O., et al., *Proc. Natl. Acad. Sci. USA* 92:7297–7301 (1995); Orson F. M., et al., *J. Immunol.* 164:6313–6321 (2000); Turunen M. P., et al., *Gene Ther.* 6:6–11 (1999); Shi N.Y., et al., *Proc. Natl. Acad. Sci. USA.* 97:7567–7572 (2000)); particles that interact with the DNA and act as carriers and enhance DNA expression such as narrospheres, microspheres, dendrimers, collagen and polylactide co-glycolides (Leong K. W., et al., *J. Controlled Release* 53:183–193 (1998); Baranov A., et al., *Gene Ther.* 6:1406–1414 (1999); Lunsford L., et al., *J. Drug Targeting* 8:39–50 (2000); Bertling W. M., et al., *Biotechnol. Appl. Biochem.* 13:390–405 (1991)), bulking agents such as sucrose that are injected before DNA injection to help expand the spaces between muscle cells and therefore allow better distribution of the subsequently injected DNA (Davis, H. L. et al., *Hum. Gene Ther.* 4:151–159 (1993)); detergents such as sodium glycocholate, sodium deoxycholate, beta-cyclodextrin and Exosurf® surfactant that may increase or decrease DNA expression (Freeman D. J. and Niven R. W., *Pharm. Res.* 13:202–209 (1996); Raczka E., et al. *Gene Ther.* 5:1333–1339 (1998)), cationic or non-cationic lipids that may facilitate DNA entry into lipid bilayers of cells (Liu Y., et al., *Nat. Biotechnol.* 15:167–173 (1997); Eastman S. J., et al. *Hum. Gene Ther.* 8:313–322 (1997); Simoes, S., et al., *Biochim. Biophys. Acta Biomembranes* 1463:459–469 (2000); Thierry, A. R., et al., *Gene Ther.* 4:226–237 (1997); Floch V., et al. *Biochim. Biophys. Acta Biomembranes* 1464:95–103 (2000); Egilmez N. K., et al. *Biochem. Biophys. Res. Commun.* 221:169–173 (1996)), DNA binding agents such as histones or intercalaters that protect the DNA from DNases (Manthorpe, M., et al., *Hum. Gene Ther.* 4:419–431 (1993); Wolff, J. A., *Neuromuscul. Disord.* 7:314–318 (1997): WO 99/31262) or agents that enhance plasmid DNA transcription such as histone deacetylase inhibitor FR901228 or 8-Bromo-cyclic AMP (Yamano, T., et al., *Mol. Ther.* 6:574–580 (2000); Aria H., et al. *Gene Ther.* 7:694–702 (2000)). Physical manipulations include removal of nerves that control muscle contraction (Wolff, J. A., et al., *BioTechniques* 11:575–585 (1991)); electroporation that electrically opens muscle cell pores allowing more DNA entry (Aihara, H. and Miyazaki, J., *Nature Biotechnol.* 16:867–870 (1998); Mir, L. M., et al., *C R Acad Sci. III* 321:893–899 (1998), Mir, L. M., et al., *Proc. Natl. Acad. Sci, USA* 96:4262–4267 (1999); Mathiesen, I., *Gene Ther.* 6:508–514 (1999); Rizzuto, G., et al., *Proc. Natl. Acad. Sci. USA* 96:6417–6422 (1999)); use of intravascular pressure (Budker, V., et al., *Gene Ther.* 5:272–276 (1998)); use of sutures coated with plasmid DNA (Labhasetwar, V., et al,, *J. Pharm. Sci.* 87:1347–1350 (1998); Qin, Y., et al., *Life Sci.* 65:2193–2203 (1999)); use of sponges soaked with DNA as intramuscular depots to prolong DNA delivery (Wolff, J. A., et al. (1991), Ibid.); use of special needle-based injection methods (Levy, M. Y., et al., *Gene Ther.* 3:201–211 (1996); Doh, S. G., et al. (1997), Ibid.); and of needleless-injectors that propel the DNA into cells (Gramzinski, R. A., et al., *Molec. Med.* 4:109–118 (1998); Smith, B. F., et al., *Gene Ther.* 5:865–868 (1998); Anwer, K., et al. (1999) Ibid.). In addition, Wolff, J. A., et al. (1991) Ibid. and Manthorpe, M., et al., (1993) Ibid. refer to conditions affecting direct gene transfer into rodent muscle in vivo.

WO99/64615 identifies the use of products and methods useful for delivering formulated nucleic acid molecules using electrical pulse voltage delivery. Examples include the formulation of plasmid DNA in a saline solution containing agents that promote better delivery of the plasmid DNA into cells in vivo when the formulation is delivered with an electrical pulse. Electrical pulse delivery often comprises electroporation where an electrical pulse is delivered to a tissue that is previously injected with a drug. Electroporation of a tissue causes transient interruption of cell membranes allowing more drug to enter the cell through the interruptions or "pores." The agents in the saline DNA solution that promote delivery of the DNA into electroporated tissues include propylene glycols, polyethylene glycols, poloxamers (block copolymers of propylene oxide and ethylene oxide), or cationic lipids. The WO99/64615 publication claims that the way that these agents enhance delivery of the DNA into cells is by either protecting the DNA from degradation by DNases or by condensing the DNA into a smaller form, or both.

U.S. Pat. No. 5,470,568 describes the use of surface active copolymers to enhance repair of permeablized cells, treat tissue damage, and to increase the efficiency of incorporation of exogenous molecules, e.g., DNA into cells in vitro. The '568 patent describes the use of poloxamers for these purposes, either with or without the use of a high energy phosphate compound, for example, ATP or phosphocreatine.

Many of these attempts to enhance tissue transduction have used agents that destroy muscle (bupivacaine, barium chloride) and actually lower expression (Norman, J. et al., *Methods in Molec. Med.* 29:185–196 (1999)); have to be pre-injected before the DNA (sucrose); are expensive organic polymers (polyvinyl pyrollidine), mutagens (intercalaters), antigenic proteins (histones) or devices that destroy muscle tissue (needleless or needle-free injectors); or need to be inserted surgically (sutures, sponges, intravascular pressure). Furthermore, most of these methods may be expensive and not suitable or practical for human use.

On the other hand, little attention has been given to the use of alternative salt solutions and/or auxiliary agents in the pharmaceutical formulation as a way of enhancing the efficiency of a polynucleotide-based polypeptide delivery. Investigators in this field routinely use normal saline or phosphate buffered saline ("PBS": 0.9% (i.e., about 154 mM) NaCl and 10 mM Na-phosphate) solutions for polynucleotide delivery, e.g., by intramuscular injection, because they are physiologically isotonic, isoosmotic, stable, nontoxic, and also because they have been traditionally used for human intramuscular injections of other drugs. Sodium phosphate, in the absence of saline, has been used in humans for delivery of non-polynucleotide-based (e.g., small molecules) administered via the intramuscular or intravenous routes (See generally, *Physician's Desk Reference.* Medical Economics Co, Monyvale, N.J. (1998)).

Sodium or potassium phosphate have been reported to enhance Lipofectin™-mediated transfection of human osteosarcoma cells in vitro (Kariko, K., et al., *Biochim Biophys Acta* 1369:320–334 (1998)), and the use of RPMI cell culture medium buffered with $NaHCO_3/Na_2HPO_4$ were reported to be the best medium for forming DNA/cationic lipid complexes in vitro. (Kichler, A., et al., *Gene Ther.* 5:855–860 (1998)).

Poloxamers have been approved for human use for intramuscular, intravenous, intraventricular, oral and topical administration. For example, Poloxamer 188 has been used as an adjunct to primary percutaneous transluminal coronary angioplasty for acute myocardial infarction (O'Keefe et al, *Am. J Cardiol.*, 78:747–750 (1996)). Poloxamer 188 (RheothRx) has also been used in a pilot study on acute painful episode of sickle cell disease (Adams-graves et al., *Blood,* 90:5:2041–2046 (1997)).

There remains a need in the art for a convenient and safe way of improving the effectiveness of in vivo polypeptide delivery via direct administration of a polynucleotide. Aqueous solutions of certain salts including sodium phosphate have been used in humans (i.e., intramuscular injection of various small molecule drugs), and detergents or surfactants as auxiliary agents are common additives in drugs administered into human tissues. However, the use of certain salts or auxiliary agents, or a combination thereof to improve the transduction, i.e., the entry into cells, and/or expression-enhancing efficiency of polynucleotides delivered in vivo is new.

SUMMARY OF THE INVENTION

The present invention is broadly directed to compositions, and methods for using such compositions, for improving the effectiveness of a polypeptide, delivery into a vertebrate by administering in vivo, a polypeptide-encoding polynucleotide in an aqueous solution of specific salts and/or auxiliary agents. The polynucleotide is incorporated into the cells of the vertebrate in vivo, and encodes a detectable amount of a prophylactically or therapeutically effective amount, of a desired polypeptide.

The present invention provides a composition selected from the group consisting of: (a) a composition comprising about 1 ng to about 30 mg of a polynucleotide in an aqueous solution, where the polynucleotide operably encodes a polypeptide within vertebrate cells in vivo; a salt M-X dissolved in the aqueous solution at a molar concentration from about 20 mM to about 300 mM, and reaction, association, or dissociation products thereof, where M is an alkali metal (e.g., Li+, Na+, K+, Rb+), preferably sodium or potassium, and where X is an anion selected from the group consisting of phosphate, acetate, bicarbonate, sulfate, pyruvate, and an organic monophosphate ester, preferably glucose 6-phosphate or DL-α-glycerol phosphate; (b) a composition comprising about 1 ng to about 30 mg of a polynucleotide in aqueous solution, where the polynucleotide operably encodes a polypeptide within vertebrate cells in vivo; and an auxiliary agent such as, but not limited to poloxamers, DMSO, IGEPAL® CA 630, NONIDET NP-40®, Nonidet P40, Triton X-100™, Triton X-114™, sodium dodecyl sulfate, Tween-20®, Tween-80®, stachyose, EDTA, Thesit®, combinations thereof, and reaction, association, or dissociation products thereof, (c) a composition comprising: about 1 ng to about 30 mg of a polynucleotide in an aqueous solution, where the polynucleotide operably encodes a polypeptide within vertebrate cells in vivo; a salt M-X dissolved in the aqueous solution at a molar concentration from about 0.1 mM to about 150 mM, and reaction, association, or dissociation products thereof, where M is an alkali metal (e.g., Li+, Na+, K+, Rb+), preferably sodium and potassium, and where X is an anion selected from the group consisting of phosphate, acetate, bicarbonate, sulfate, pyruvate, and an organic monophosphate ester, preferably glucose 6-phosphate or DL-α-glycerol phosphate; and a cationic lipid suspended in said aqueous solution; where the aqueous solution is substantially free of chloride anion; (d) the composition of (a) further comprising the auxiliary agent as described in (b); and (e) the composition of (c) further comprising the auxiliary agent as described in (b).

Another aspect of the present invention is a method for delivering a polypeptide into a vertebrate, comprising administering to the vertebrate one or more of compositions (a) through (e); such that the polypeptide encoded by the delivered polynucleotide is expressed in the vertebrate, in an amount sufficient to be detectable or to elicit a biological response in the vertebrate.

Another aspect of the present invention is a method for delivering a therapeutic polypeptide into a vertebrate, comprising administering to a vertebrate in need of such a therapeutic polypeptide one or more of compositions (a) through (e); such that a therapeutic polypeptide encoded by the delivered polynucleotide is expressed in the vertebrate, in a therapeutically effective amount.

The present invention also provides a method of producing antibodies to a polypeptide in a vertebrate, comprising administering to the vertebrate one or more of compositions (a) through (e); such that a polypeptide encoded by the delivered polynucleotide is expressed in the vertebrate, in a sufficient amount to generate antibody to the encoded polypeptide in the vertebrate.

The present invention also provides a method of enhancing or modulating an immune response in a vertebrate in need of such an enhanced or modulated immune response, comprising administering to the vertebrate one or more of compositions (a) through (e); such that an immunogenic and/or immunomodulatory polypeptide encoded by the delivered polynucleotide is expressed in the vertebrate, in a sufficient amount to induce a desired immune response in the vertebrate to prevent disease or treat disease, i.e., cure disease, reduce the severity of disease symptoms, or prolong the life of the vertebrate.

The invention further provides a method of delivering a physiologically or metabolically necessary polypeptide to a vertebrate incapable of making a sufficient amount of a functional form of the polypeptide, comprising administering to the vertebrate one or more of compositions (a) through (e); such that a functional self polypeptide, i.e., a physiologically or metabolically necessary polypeptide encoded by the delivered polynucleotide is expressed in the vertebrate, in a sufficient amount to supply the vertebrate's requirements for the polypeptides, e.g., to restore to the vertebrate adequate, or normal levels of the polypeptides.

The present invention also provides a pharmaceutical kit selected from the group consisting of: (a) a pharmaceutical kit comprising: a container or containers holding about 1 ng to about 30 mg of a polynucleotide which operably encodes a polypeptide within vertebrate cells in vivo; an amount of a salt M-X which, when dissolved in a prescribed volume of distilled water, results in an aqueous solution with a molar concentration of said salt from about 20 mM to about 300 mM, and reaction, association, or dissociation products thereof, where M is an alkali metal (e.g., Li+, Na+, K+, Rb+), preferably sodium or potassium, and where X is an anion selected from the group consisting of phosphate, acetate, bicarbonate, sulfate, pyruvate, and an organic monophosphate ester, preferably glucose 6-phosphate or DL-(α-glycerol phosphate; and optionally, an administration means and/or an instruction sheet; whereby the polynucleotide is provided in a prophylactically or therapeutically effective amount to treat a vertebrate; (b) a pharmaceutical kit comprising: a container or containers holding about 1 ng to about 30 mg of a polynucleotide which operably encodes a polypeptide within vertebrate cells in vivo; an auxiliary agent such as, but not limited to poloxamers, DMSO, IGEPAL® CA 630, NONIDET NP-40®, Nonidet P40, Triton X-100™, Triton X-114™, sodium dodecyl sulfate, Tween-20®, Tween-80®, stachyose, EDTA, Thesit®, combinations thereof, and reaction, association, or dissociation products thereof; and optionally, an administration means and/or an instruction sheet; whereby the polynucleotide is provided in a prophylactically or therapeutically effective amount to treat a vertebrate; (c) a pharmaceutical kit comprising: a container or containers holding about 1 ng to about 30 mg of a polynucleotide which operably encodes a polypeptide within vertebrate cells in vivo; an amount of a salt M-X which, when dissolved in a prescribed volume of distilled water, results in an aqueous solution with a molar concentration of said salt from about 0.1 mM to about 150 mM, and reaction, association, or dissociation products thereof, where M is an alkali metal (e g., Li+, Na+, K+, Rb+), preferably sodium and potassium, where X is an anion selected from the group consisting of phosphate, acetate, bicarbonate, sulfate, pyruvate, and an organic monophosphate ester, preferably glucose 6-phosphate or DL-α-glycerol phosphate, and where the aqueous solution formed thereby is essentially free of chloride anion; a cationic lipid; and optionally, an administration means and/or an instruction sheet; whereby the polynucleotide is provided in a prophylactically or therapeutically effective amount; (d) the pharmaceutical kit of (a) further comprising an auxiliary agent as described in (b); and (e) the pharmaceutical kit of (c) further comprising the auxiliary agent as described in (b). Any of components of the pharmaceutical kits (a) through (e) can be provided in a single container, or in multiple containers packaged together.

The inventors have discovered that delivery of the compositions provided herein to a vertebrate results in much improved in vivo polypeptide expression over the delivery of existing nucleic acid-based compositions, e.g., compositions comprising polynucleotides which encode a polypeptide and an aqueous solution consisting of sterile water, normal saline (i.e., 154 mM sodium chloride), or phosphate buffered saline (i.e., 154 mM sodium chloride plus 10 mM sodium phosphate). One advantage of the present invention is cost effectiveness since the invention requires a relatively smaller amount of a polynucleotide to reach a predetermined level of expression.

BRIEF DESCRIPTION OF THE DRAWINGS/FIGURES

The foregoing aspects and advantages of the present invention will be readily apparent to one skilled in the art upon reference to the figures and the detailed description which follows.

FIG. 1 shows the schematic contents of plasmid DNAs used in the examples that follow. All vectors contain a pUC19 origin of replication, human cytomegalovirus intron A, and the bacterial kanamycin resistance gene. "Lux" denotes the coding region encoding luciferase, from the firefly, *Photinus pyralis*; "CMV" denotes the human cytomegalovirus immediate early region—promoter and enhancer; "BGH" denotes the bovine growth hormone transcriptional terminator; "LacZ" denotes the coding region encoding the β-galactosidase protein of *Escherichia coli*; "RSV" denotes the Rous sarcoma virus promoter and enhancer; "EPO" denotes the coding region encoding murine erythropoietin; "SEAP" denotes the coding region for secreted human placental alkaline phosphatase; "Rat preproinsulin" denotes the coding region for rat preproinsulin containing a point mutation to change histidine B10 (codon CAC) to aspartic acid (codon GAC), Abai, A. M., et al. *Human Gene Therapy* 10:2637–2649 (1999); "IFN-omega" denotes the coding region encoding human interferon-ω; "mRGB" denotes the modified rabbit β-globin transcriptional terminator; and "NP" denotes the coding region encoding the nucleoprotein of influenza virus A/PR/8/34. Intermediate and parental plasmids *VR1012, VR1255 and *VIJ were prepared as described by Manthorpe, M. et al., *Hum. Gene Ther.* 4:419–431 (1993), Hartikka, J. et al., *Hum. Gen. Ther.* 7:1205–1217 (1996), and Montgomery, D. L. et al., *DNA Cell Biol.* 12:777–783 (1993), respectively. VR1043 was derived from VR1012 by replacing the SacI-NdeI CMV promoter enhancer fragment with the RSV promotor enhancer.

FIG. 2A is a bar graph demonstrating the effectiveness of sodium phosphate concentration on luciferase expression in mouse muscle. Fifty μg of plasmid VR1223 DNA per 50 μl sodium phosphate solution at the indicated molar concentrations was injected into mouse quadriceps and the muscles were extracted and assayed for enzyme activity 7 days later. Bars represent Standard Error of the Mean (n=50, 5 experiments each with n=10 per concentration). Peak expression occurred with DNA dissolved in 150 mM sodium phosphate, and yielded 386 ng luciferase per muscle which is 4.3-fold higher than the saline average (dashed line at 89 ng luciferase per muscle). The 80, 100, 150 and 200 mM sodium phosphate values were significantly higher than saline by Mann-Whitney rank sum test (p<0.05).

FIG. 2B is a bar graph demonstrating the effect of pH of the sodium phosphate and potassium phosphate solutions on luciferase expression in mouse muscle. Fifty μg of plasmid VR1223 DNA per 50 μl sodium phosphate and potassium phosphate solution at the indicated pH was injected into mouse quadriceps and the muscles were extracted and assayed for enzyme activity 7 days later. Bars represent Standard Error of the Mean (n=20 muscles per group).

Figure 3:
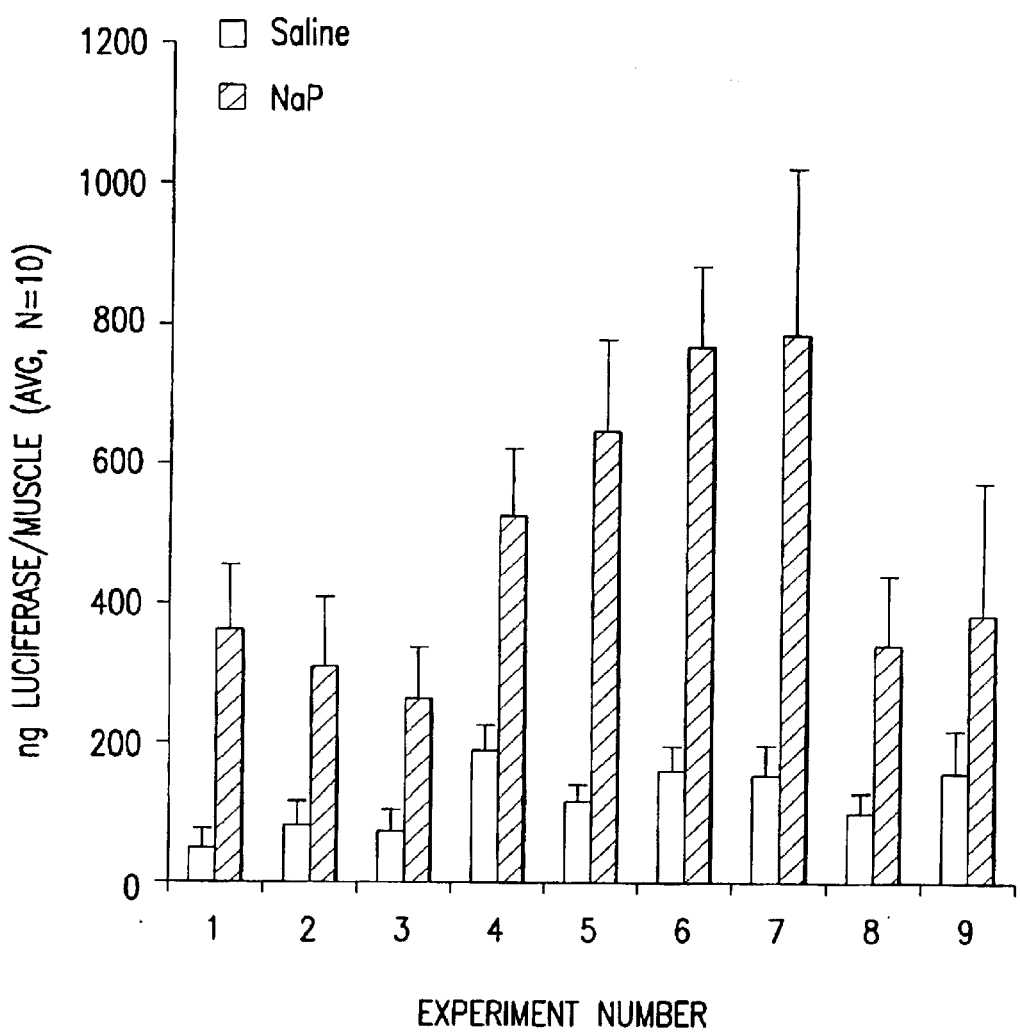

FIG. 3 is a bar graph demonstrating the reproducibility of the enhancement of luciferase expression in muscle upon delivery in 150 mM sodium phosphate. In each of nine experiments, ten quadriceps muscles in 5 mice per group were injected with 50 μg of plasmid VR1223 DNA dissolved in 50 μl saline or in 150 mM sodium phosphate (NaP). Bars represent the average ng luciferase per muscle for each experiment numbered 1 through 9. Error bars represent Standard Error of the Mean.

Figure 4A:
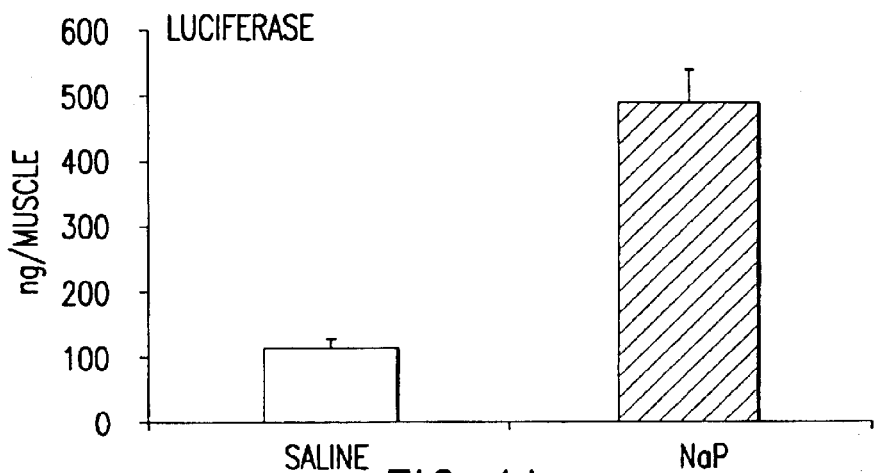
Figure 4B:
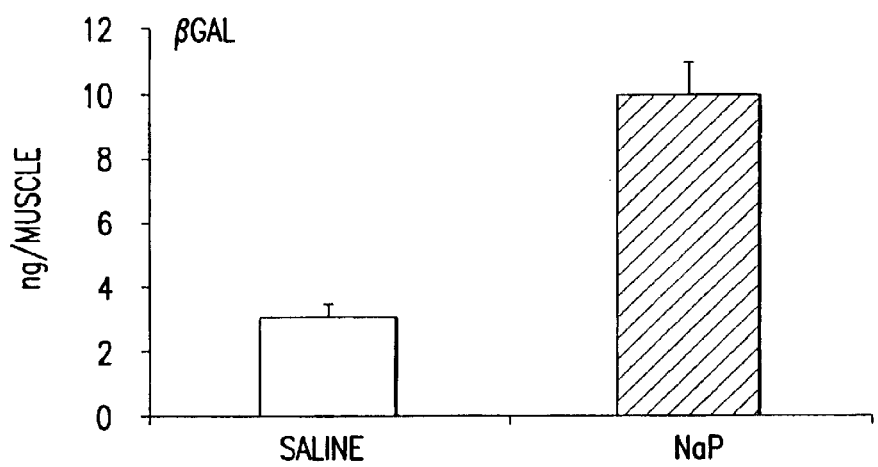
Figure 4C:
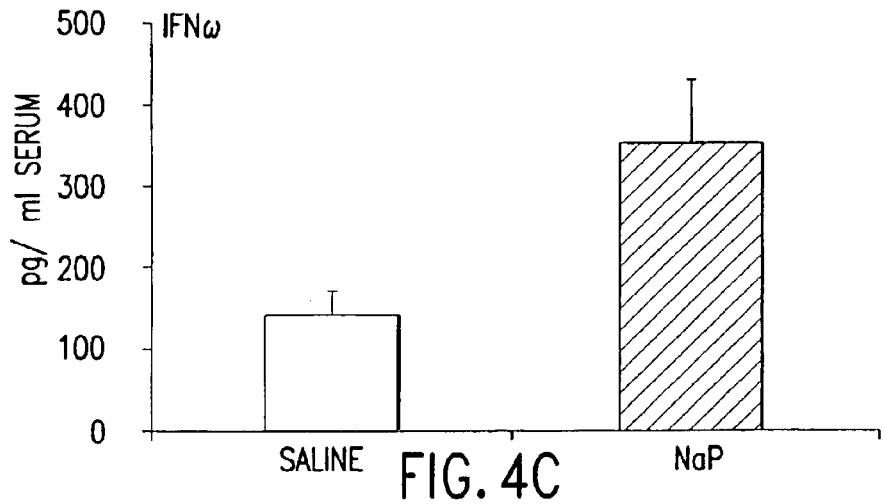

FIG. 4 shows the comparison of the effect of a 150 mM sodium phosphate solution on the expression of three reporter genes. Fifty μg of plasmid VR1223 (luciferase), 10 μg of plasmid VR1418 (β-galactosidase, or LacZ) or 50 μg of plasmid VR4151 (human IFNω) dissolved in 50 μl saline or in 150 mM sodium phosphate solution were injected into the quadriceps muscles of BALB/c mice. For luciferase and LacZ DNAs, the muscles were extracted and assayed 7 days later for enzyme activity. For IFN-ω DNA, serum was collected at 7 days after the injection and assayed for IFN-ω protein. Values are expressed as average ng of gene product per muscle or per ml serum. Bars represent Standard Error of the Mean. For luciferase, $n_{Saline}=413$, $n_{NaP}=120$; for β-galactosidase, $n_{Saline}=119$, $n_{Nap}=180$; for IFN-ω, $n_{Saline}=10$, $n_{Nap}=9$. The average expression in NaP was significantly higher than saline by Mann-Whitney rank sum test for luciferase (p=0.001), β-galactosidase (p=0.001) and IFN-ω (p=0.02).

Figure 5A:
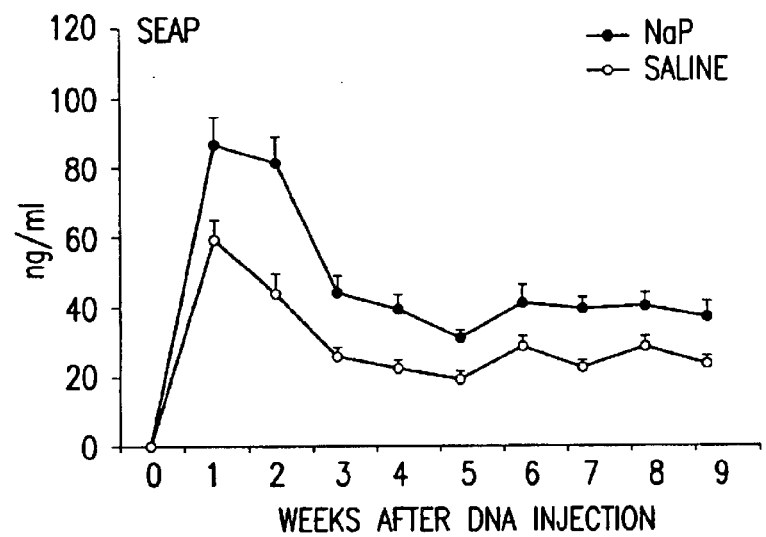
Figure 5B:
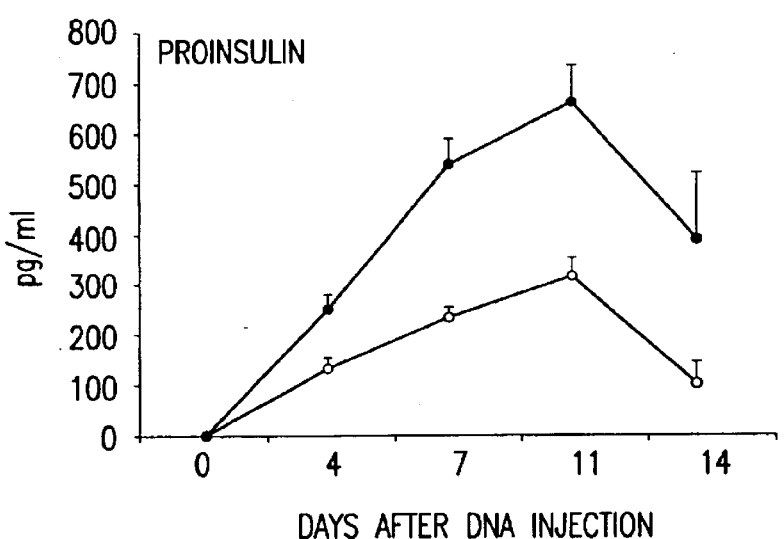
Figure 5C:
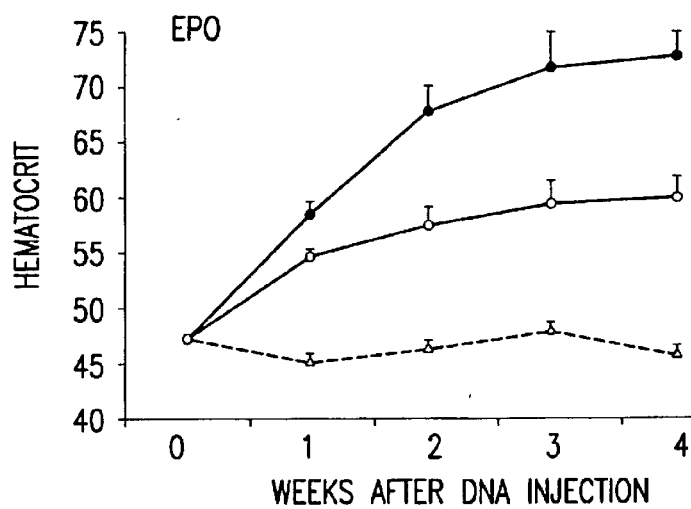

FIGS. 5A–C show long-term effects of a 150 mM sodium phosphate solution on the expression of secreted reporter gene products. Compositions comprising plasmids VR3301 encoding human placental alkaline phosphatase (SEAP), VR3502 encoding rat preproinsulin, and VR2901 encoding mouse erythropoietin, dissolved in saline or in 150 mM sodium phosphate, were injected bilaterally into mice as described in Example 1. At the indicated times after injections, serum was collected and assayed for SEAP or proinsulin expression, or hematocrits were measured as an indication of erythropoietin expression. Control mice injected with plasmid DNA encoding canine clotting Factor IX (open triangles in the lower graph) in 150 mM sodium phosphate exhibited an average hematocrit of 46. Bars represent Standard Error of the Mean (n=10). By the Mann-Whitney rank sum test, the sodium phosphate values were significantly different (p values all <0.007) from the saline values for each time point and for all three reporters.

FIGS. 6A–F show β-galactosidase staining of mouse muscle 7 days after i.m. injection of 50 μl of VR1412 formulated in saline (A, C, E) or 150 mM sodium phosphate vehicle (B, D, F). FIGS. A and B show representative muscles stained in wholemount. FIGS. C, D, E, and F show representative sections at two different magnifications of the same sections. Magnifications: A & B=25×; C & D=100×; E & F=250×.

Figure 7A:
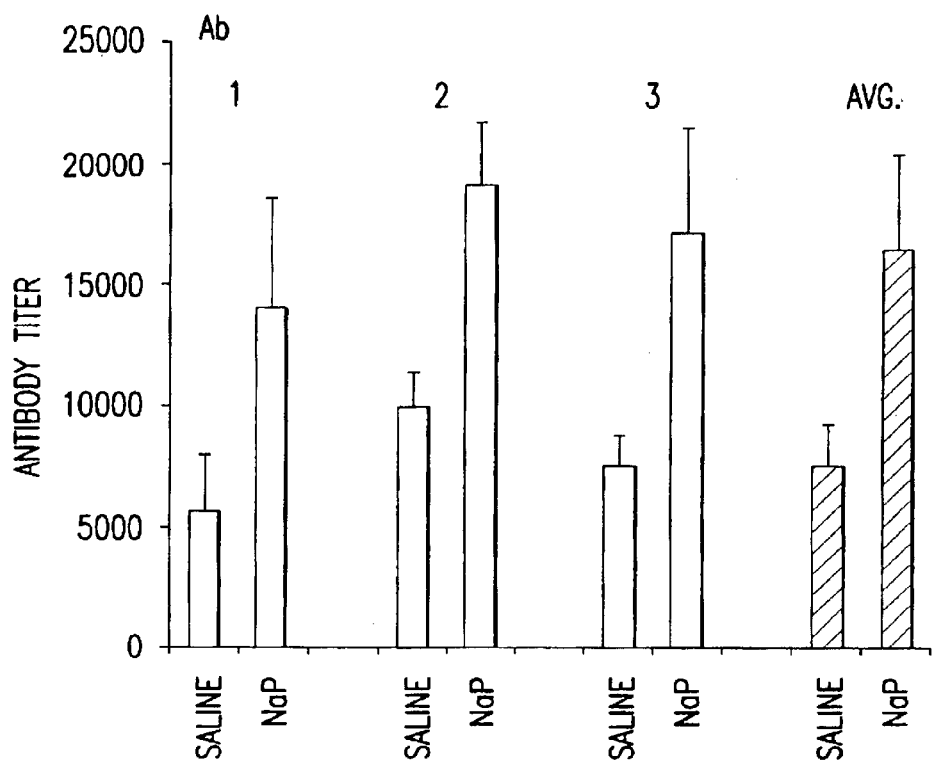

FIGS. 7A and B shows the effect of a 150 mM sodium phosphate solution on DNA vaccination. Mice were vaccinated bilaterally in the quadriceps muscle with 5 μg of plasmid VR4700, encoding the influenza virus nucleoprotein, which was dissolved in 50 μl of saline or in 50 μl of 150 mM sodium phosphate on days 0 and 21. (A) Serum was collected at day 42 and assayed for anti-NP antibody titer by ELISA. Three separate experiments were performed with 9 to 10 mice per group in each of the separate experiments, labeled 1–3. The average (Avg.) of all three experiments is indicated in the black bar. Values are expressed as anti-NP specific titer. Error bars represent Standard Error of the Mean. Average anti-NP titers from NaP groups 1–3 were significantly different from the saline averages by Mann-Whitney rank sum test (p<0.04) as was the average titers from all 3 groups (p<0.001). (B) At day 60 the spleens were collected, dissociated and assayed for the presence of NP-specific cytolytic T lymphocyte activity (4 to 5 mice for each group from one of the representative experiment). Splenocytes from unvaccinated mice served as controls ("Naïve"). Average % NP specific lysis from the saline and NaP groups were not significantly different by Mann Whitney rank sum test.

Figure 8:
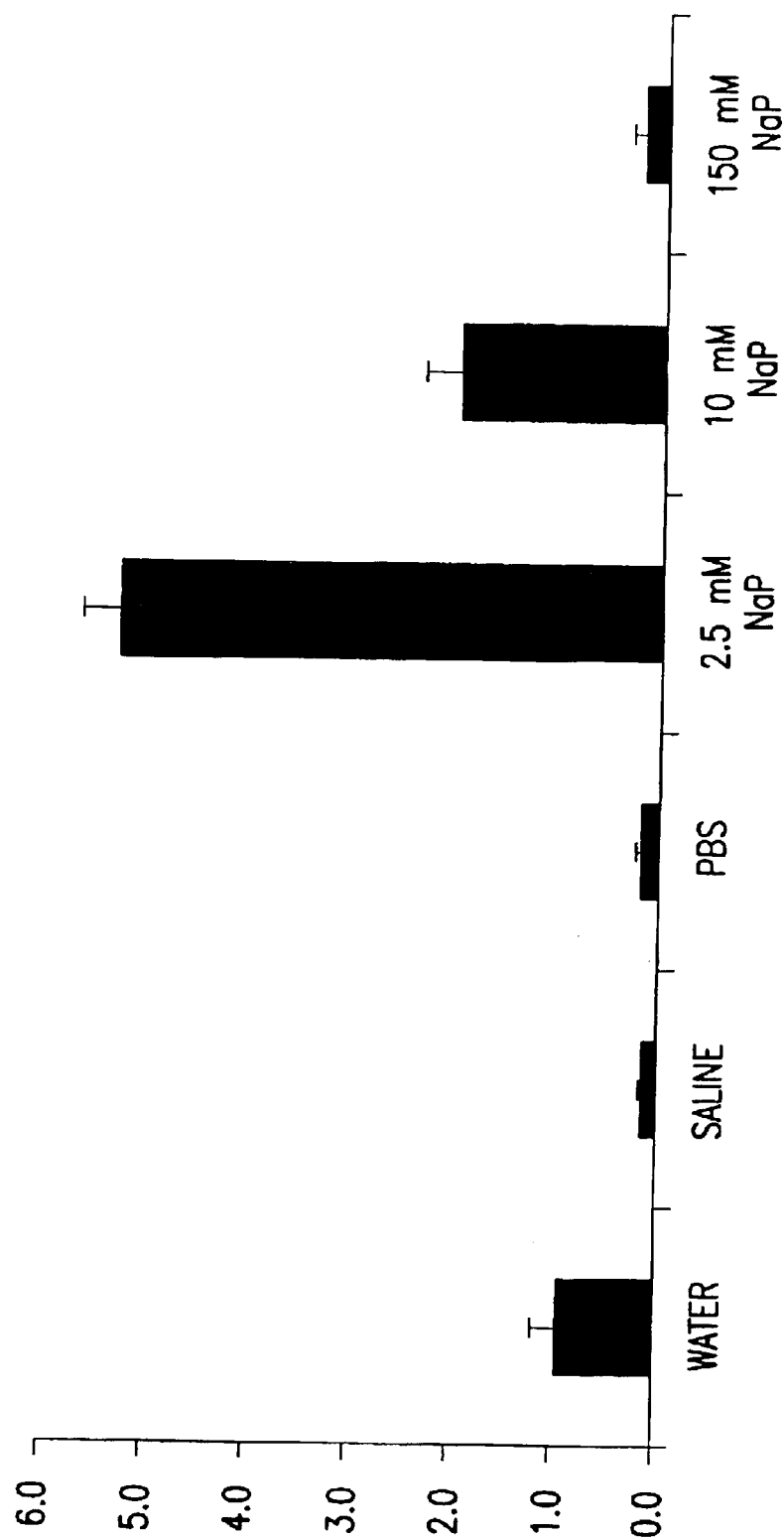

FIG. 8 shows the effects of sodium phosphate solutions on luciferase expression in lung following delivery of compositions comprising plasmid DNA encoding luciferase. Mouse lungs were intranasally instilled with compositions comprising 132 µg of plasmid VR1223 encoding luciferase, complexed with GAP-DLRIE/DOPE (1:1) cationic liposomes at a molar ratio of 4:1 DNA to lipid in water or in various aqueous solutions of sodium phosphate. The lungs were extracted 3 days later and assayed for luciferase activity. Values are expressed in ng luciferase per lung+/- Standard Error of the Mean ($n_{water}$ and $n_{2.5mNaP}$=35; $n_{10mMNaP}$, and $n_{150mMNaP}$=15 with n=5 per each individual experiment). The average of the group treated with VR1223 in 2.5 mM NaP solution was significantly higher compared to the other groups.

FIG. 9 is a bar graph demonstrating the effects of adding certain auxiliary agents into a pharmaceutical composition comprising an aqueous solution of 154 mM sodium chloride or 150 mM sodium phosphate upon luciferase expression in mouse muscle in vivo. Fifty µg of plasmid VR1255 DNA per 50 µl saline solution or 150 mM sodium phosphate solution alone, or containing the indicated auxiliary agents at the indicated concentrations, was injected into mouse quadriceps and the muscles were extracted and assayed for enzyme activity 7 days later. Addition of the auxiliary agents resulted in a 3- to 6-fold increase in luciferase expression in both 154 mM sodium chloride and 150 mM sodium phosphate (p<0.05).

Figure 10:
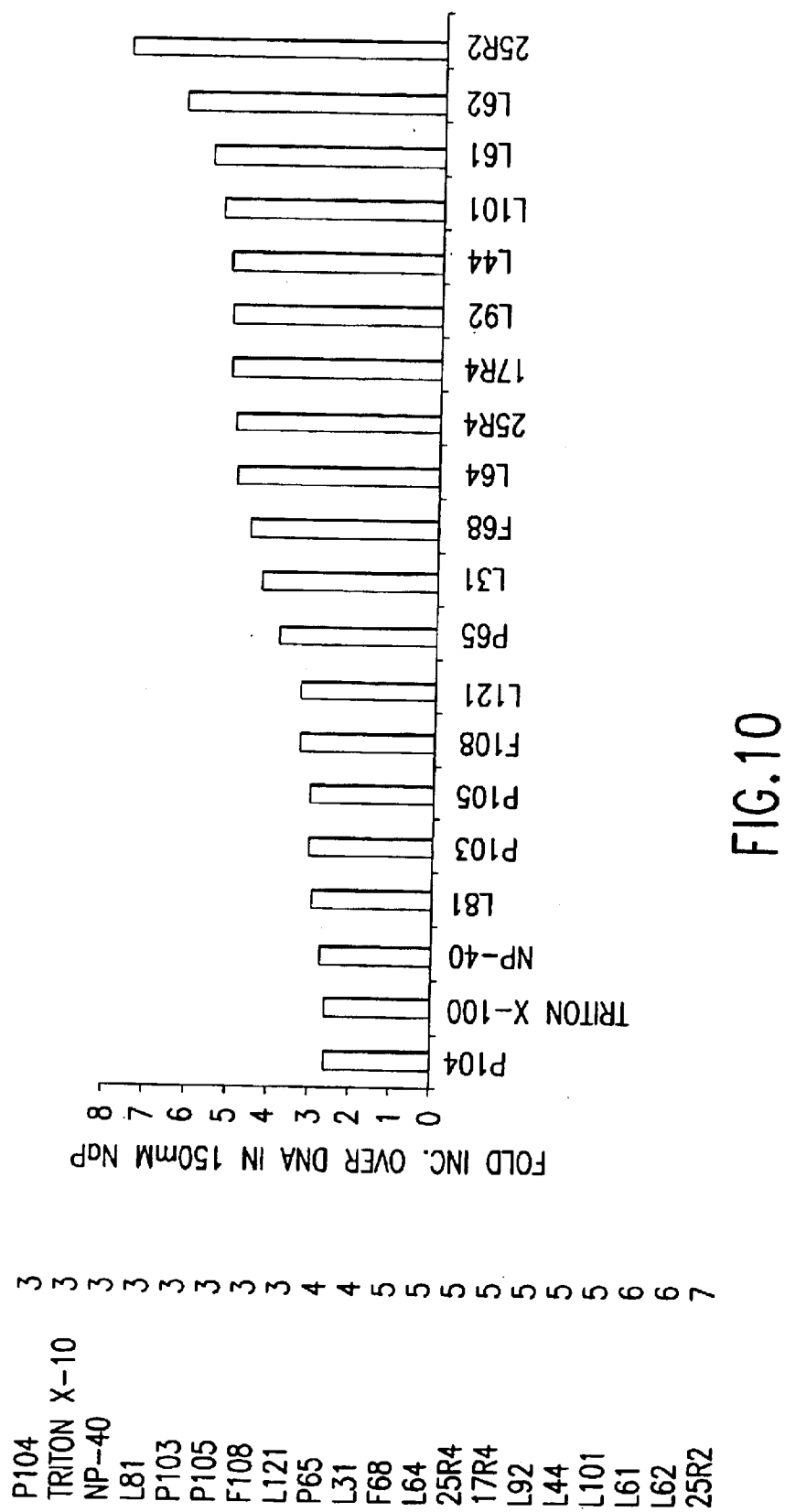

FIG. 10 is a bar graph demonstrating the effects of including certain auxiliary agents in compositions comprising an aqueous solution of 150 mM sodium phosphate upon luciferase expression in mouse muscle in vivo. Fifty µg of plasmid VR1255 DNA per 50 µl 150 mM sodium phosphate solution alone, or containing the indicated auxiliary agents at the indicated concentrations, was injected into mouse quadriceps and the muscles were extracted and assayed for enzyme activity 7 days later (n=10 per group) (p<0.05).

Figure 11:
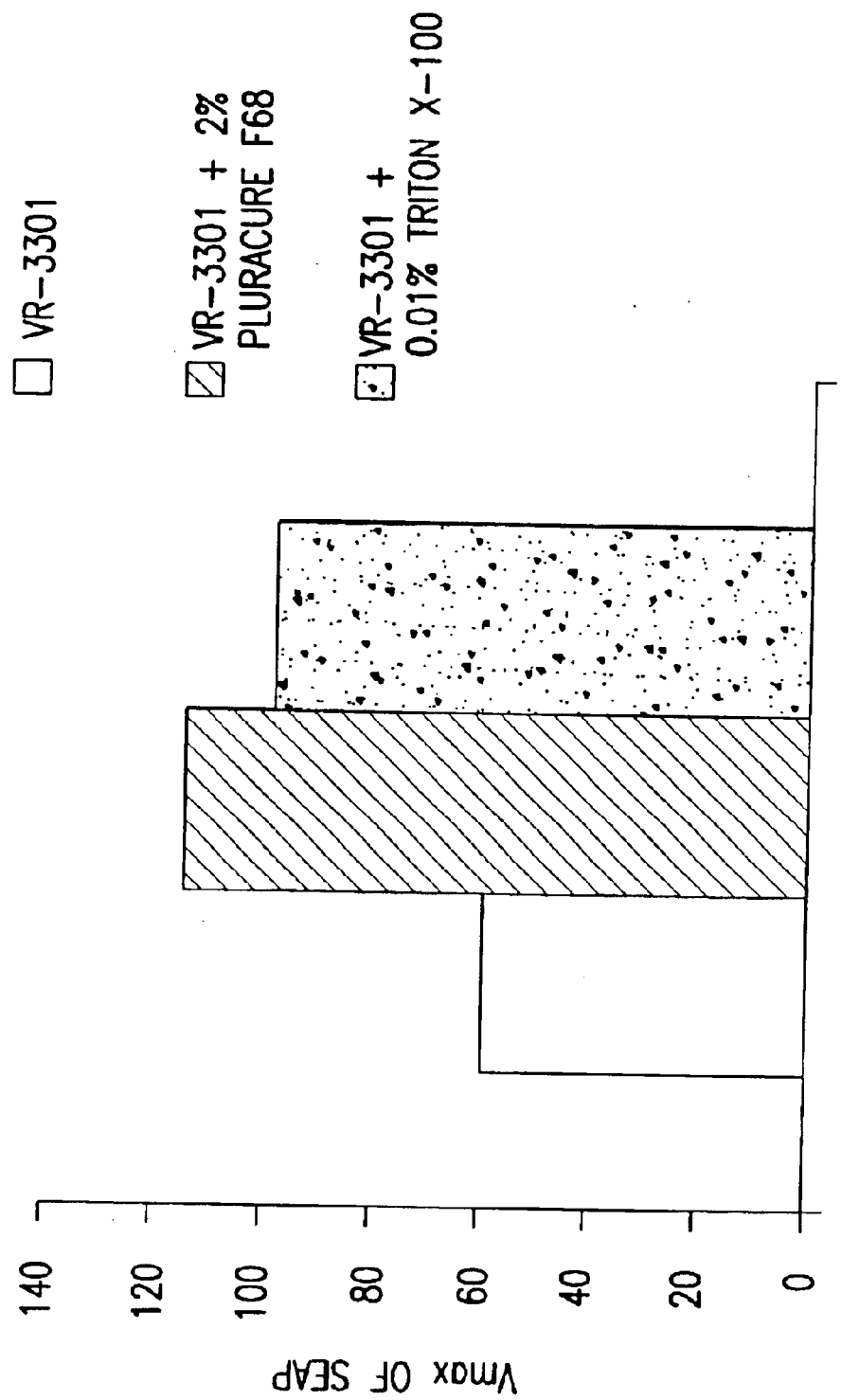

FIG. 11 is a bar graph demonstrating the effect of certain auxiliary agents upon the expression of a secreted reporter gene (secreted human alkaline phosphatase (SEAP)) in mouse muscle in vivo. Fifty µg of plasmid VR3301 DNA per 50 µl 150 mM sodium phosphate solution alone, or containing the indicated auxiliary agents at the indicated concentrations, was injected into tibialis anterior muscles of nude mice and serum was collected and assayed for SEAP activity 7 days later (n=5 per group) (p<0.05). "Pluracare" is the same as Pluronic®.

Figure 12:
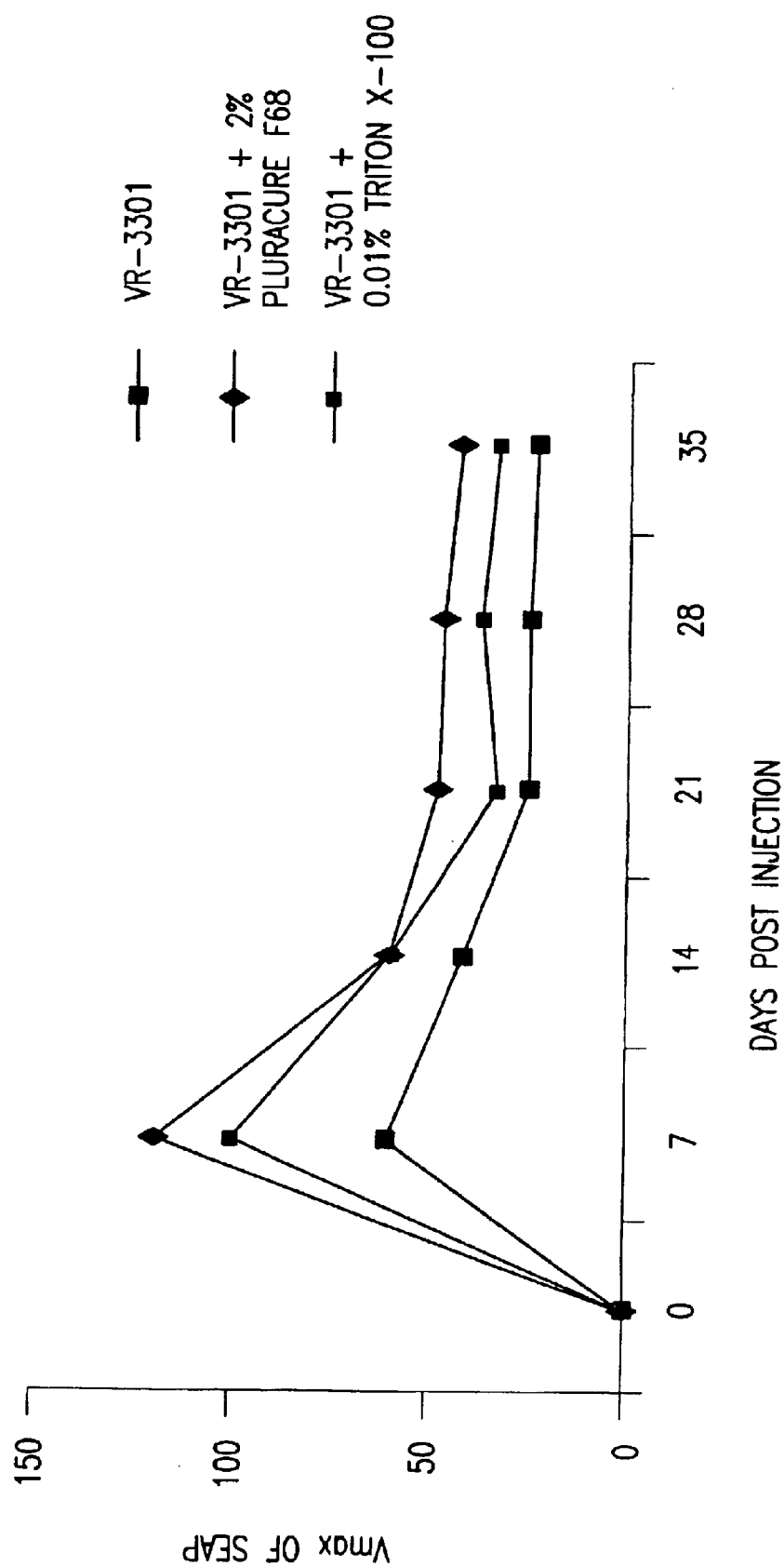

FIG. 12 illustrates the long-term effect of certain auxiliary agents upon the expression of a secreted reporter gene (SEAP) in mouse muscle in vivo. Fifty µg of plasmid VR3301 DNA per 50 µl 150 mM sodium phosphate solution alone, or containing the indicated auxiliary agents at the indicated concentrations, was injected into tibialis anterior muscles of nude mice. Serum was collected and assayed for SEAP activity at the indicated times after injection. Addition of the auxiliary agents resulted in at least a two-fold enhancement of SEAP expression out to day 35 (n=5 mice per group) (p<0.05).

Figure 13:
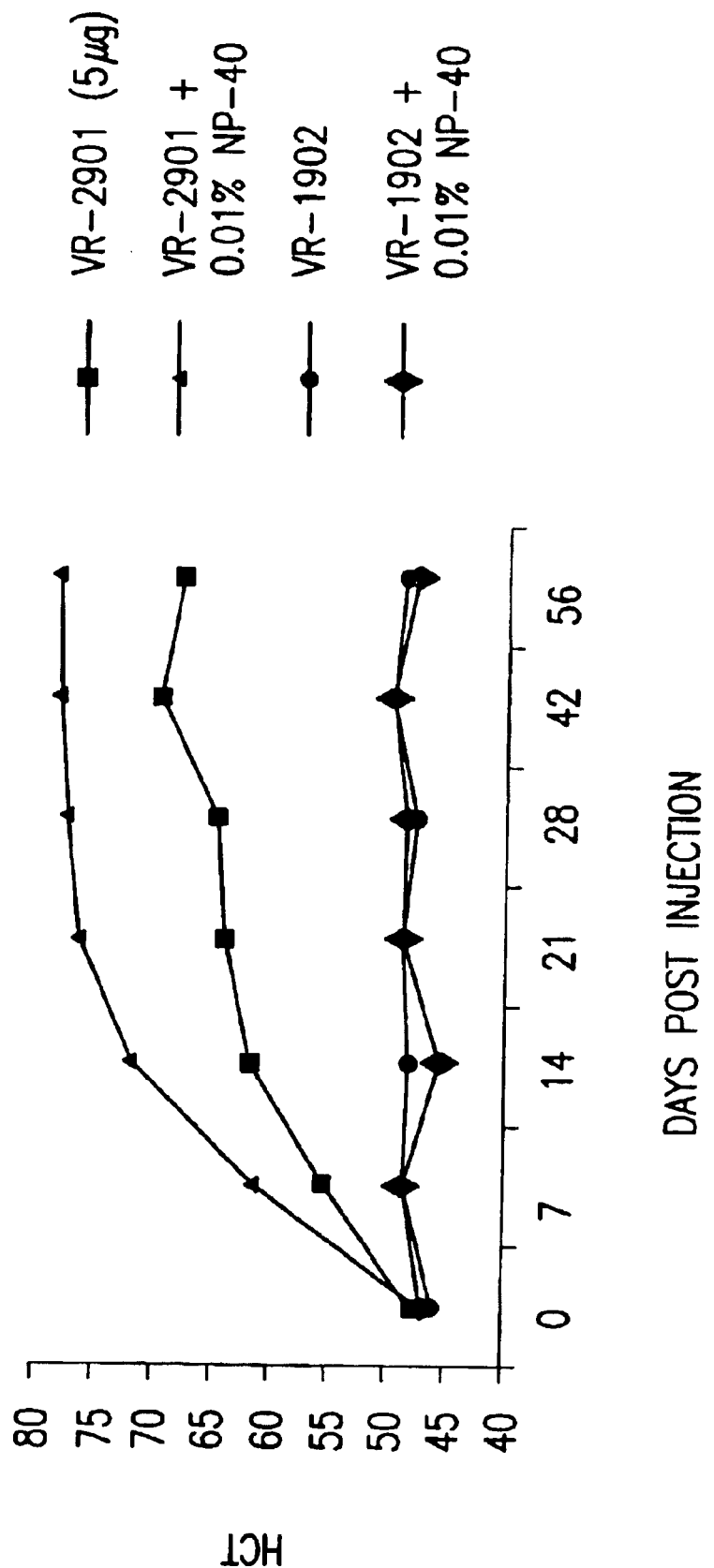

FIG. 13 illustrates the effect of an auxiliary agent on the biological activity of a therapeutic protein (erythropoietin). Five µg of plasmid VR2901 DNA (or negative control VR1902 DNA) per 50 µl 150 mM sodium phosphate solution alone, or containing the 0.01% NONIDET NP-40® was injected into mouse quadriceps muscle. At the indicated times after injection, serum was collected and hematocrits (HCT) were measured as an indication of erythropoietin expression (n=10 per group) (p<0.05).

Figure 14:
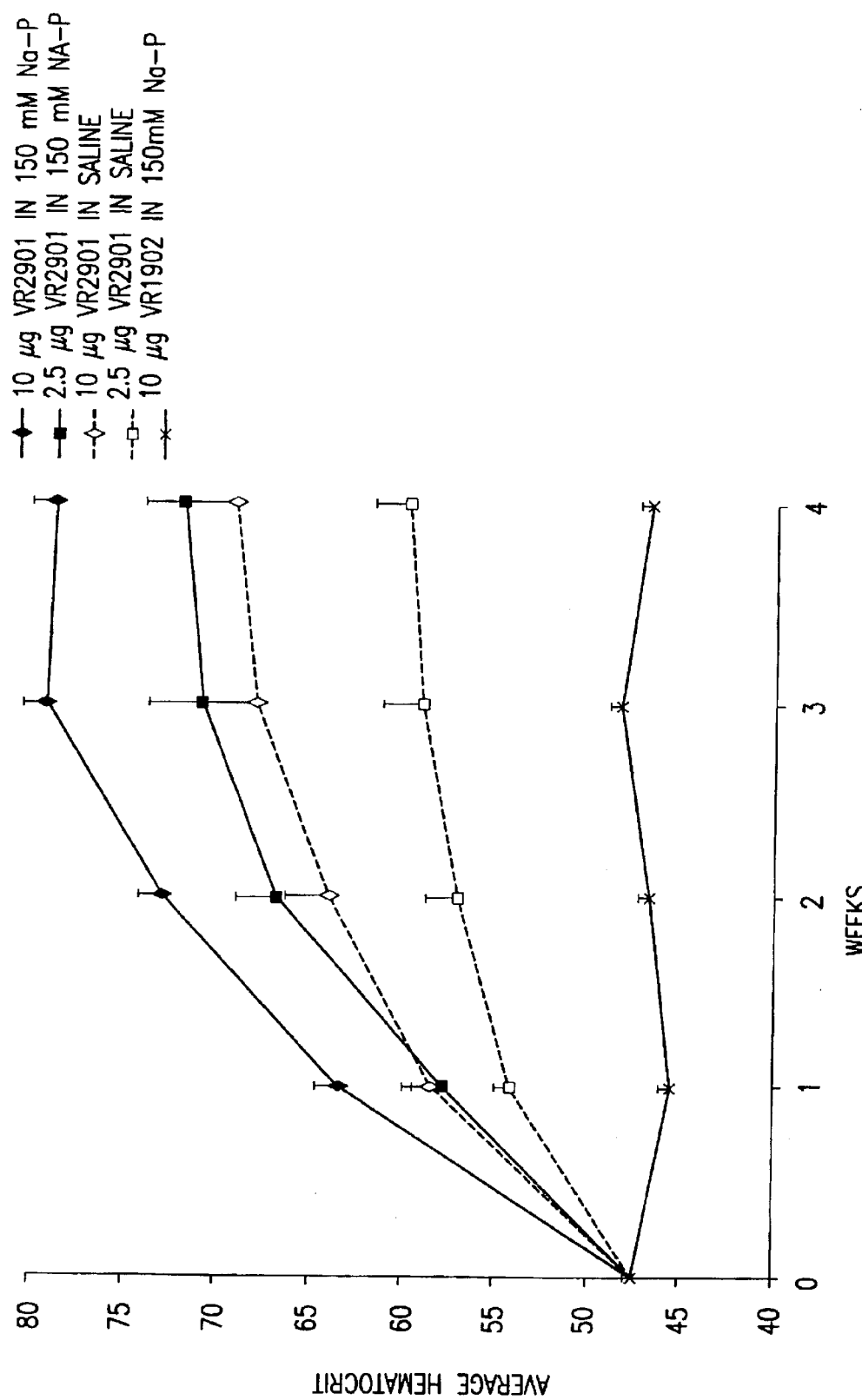

FIG. 14 illustrates that a sodium phosphate solution, compared to saline, allows for the use of a significantly smaller amount of a therapeutic protein (erythropoietin) to achieve a biological effect. Doses of 10 µg or 2.5 µg of plasmid VR2901 DNA (or negative control VR 1902 DNA encoding canine clotting Factor IX) dissolved in either 50 µl 150 mM sodium phosphate solution or saline were injected into mouse quadriceps muscle. At the indicated times after the injections, serum was collected and hematocrits were measured as an indication of erythropoietin expression. Bars represent Standard Error of the Mean (n=10 for groups 1–4, n=5 for group 5).

Figure 15:
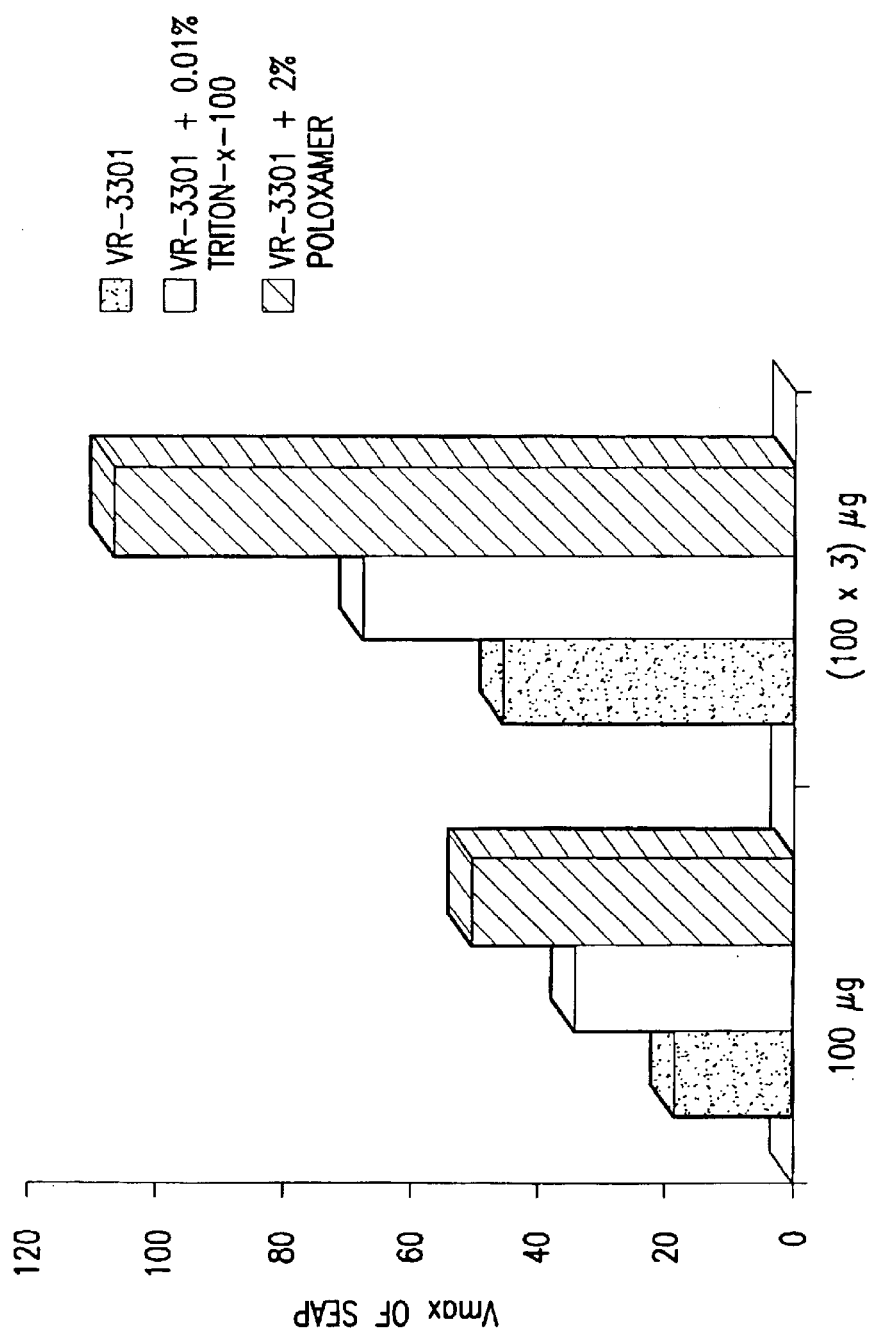

FIG. 15 illustrates the enhancing effect of adding certain auxiliary agents upon the expression of a secreted reporter gene (SEAP) in mouse muscle in vivo. Doses of 100 µg or 300 µg of plasmid VR3301 DNA per 50 µl 150 mM sodium phosphate solution alone, or containing the indicated auxiliary agent at the indicated concentrations were injected into tibialis anterior muscles of nude mice and serum was collected and assayed for SEAP activity at 7 days post-injection. Addition of the auxiliary agents resulted in levels of SEAP expression which were the same or better than 3-times greater DNA injected alone (n=5 per group) (p<0.5).

Figure 16B:
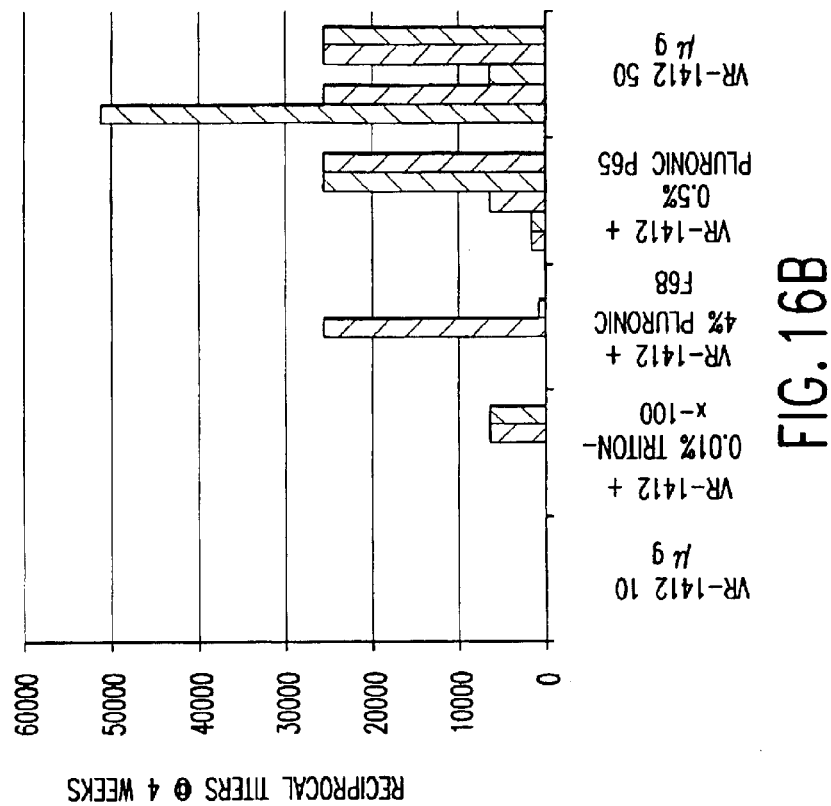
Figure 16A:
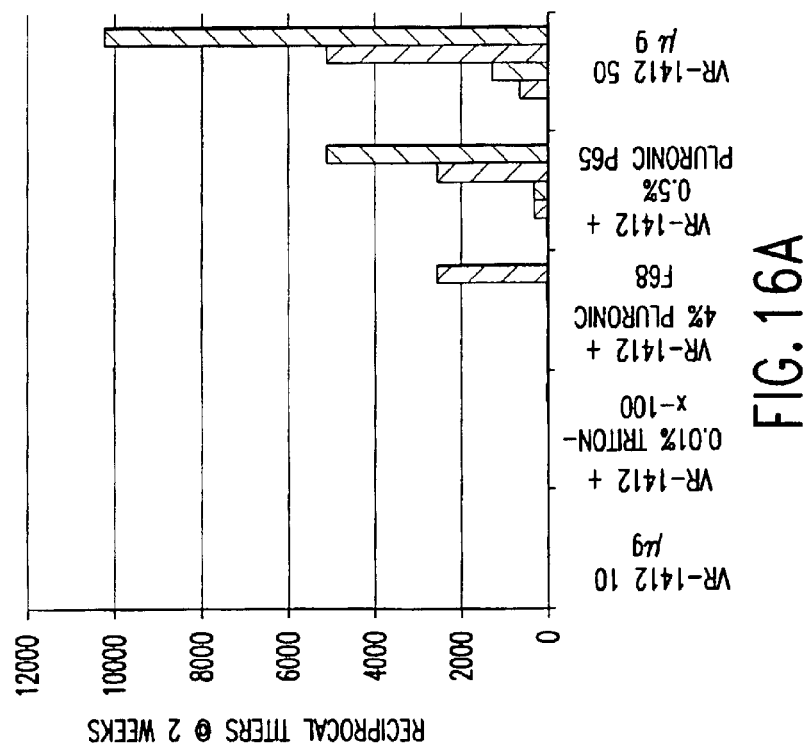
Figure 16C:
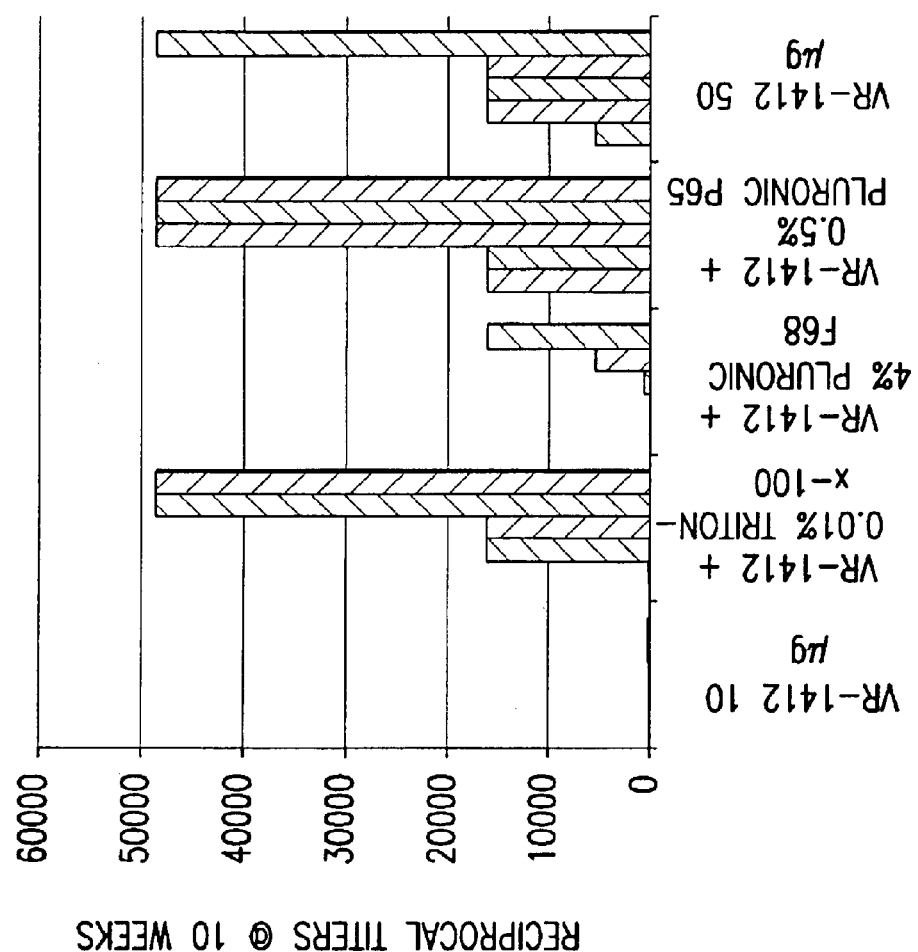
Figure 16D:
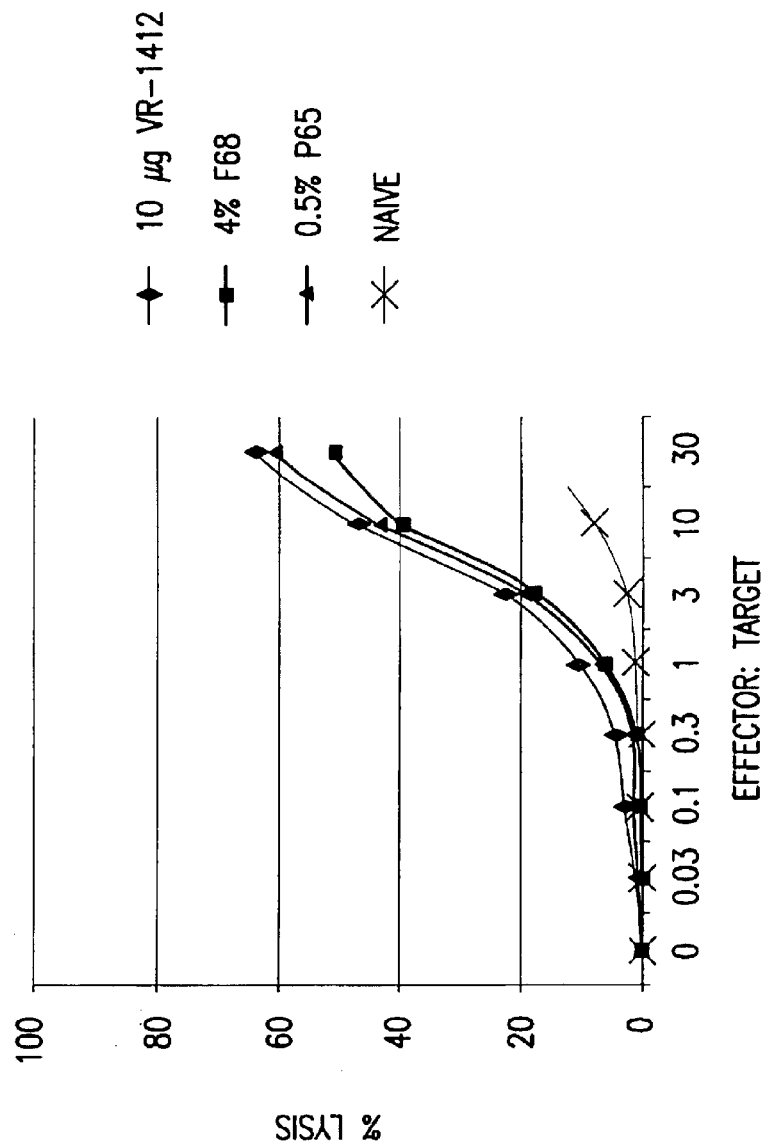

FIGS. 16A–D show the effects of a 150 mM sodium phosphate solution containing certain auxiliary agents on DNA vaccination. Mice were injected bilaterally in the quadriceps muscles with 5 µg of plasmid VR1412 (10 µg total DNA), encoding β-galactosidase, which was dissolved in 50 µl of 150 mM sodium phosphate with or without auxiliary agents on day 0. Serum was collected at 2 weeks (FIG. 16A), 4 weeks (FIG. 16B), and 10 weeks (FIG. 16C) after vaccination and assayed for anti-β-galactosidase antibody titer by ELISA. All groups treated with VR1412 in the sodium phosphate solution containing an auxiliary agent were positive for anti-β-galactosidase antibody whereas the groups treated with the same solution except for the absense of an auxiliary agent were negative (n=5 per group) (p<0.05). For CTL activity, mice were injected with 10 µg of VR1412 on day 0 then boosted on day 21. Spleens were harvested 7 weeks following initial immunizations and stimulated for 5–6 days with 1 µM β-galactosidase peptide and 0.5 U/ml of IL-2. Splenocytes were assayed for lysis by standard $^{51}$Cr release assay. FIG. 16D shows that addition of an auxiliary agent has no effect on the cytotoxic T cell lysis (CTL).

Figure 17A:
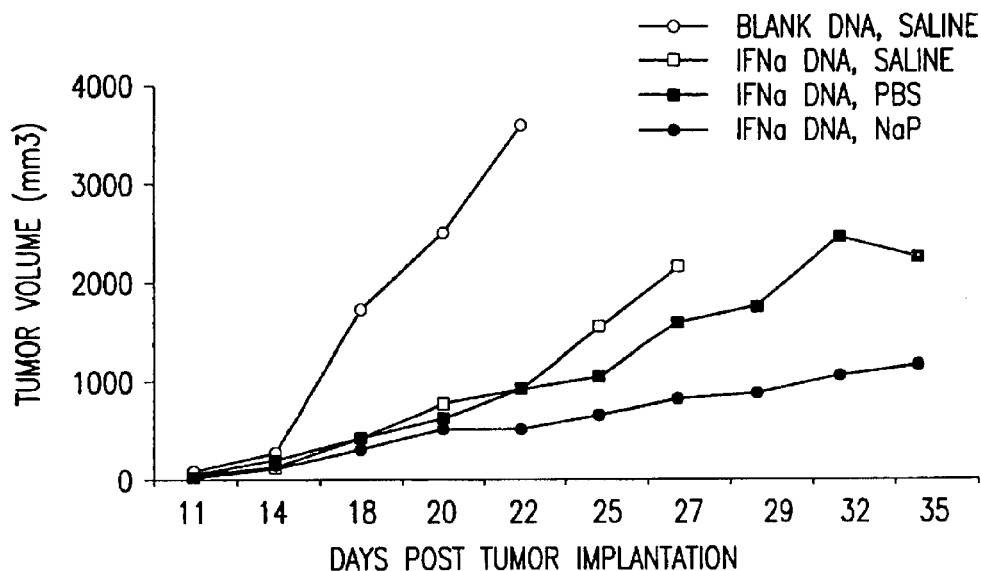
Figure 17B:
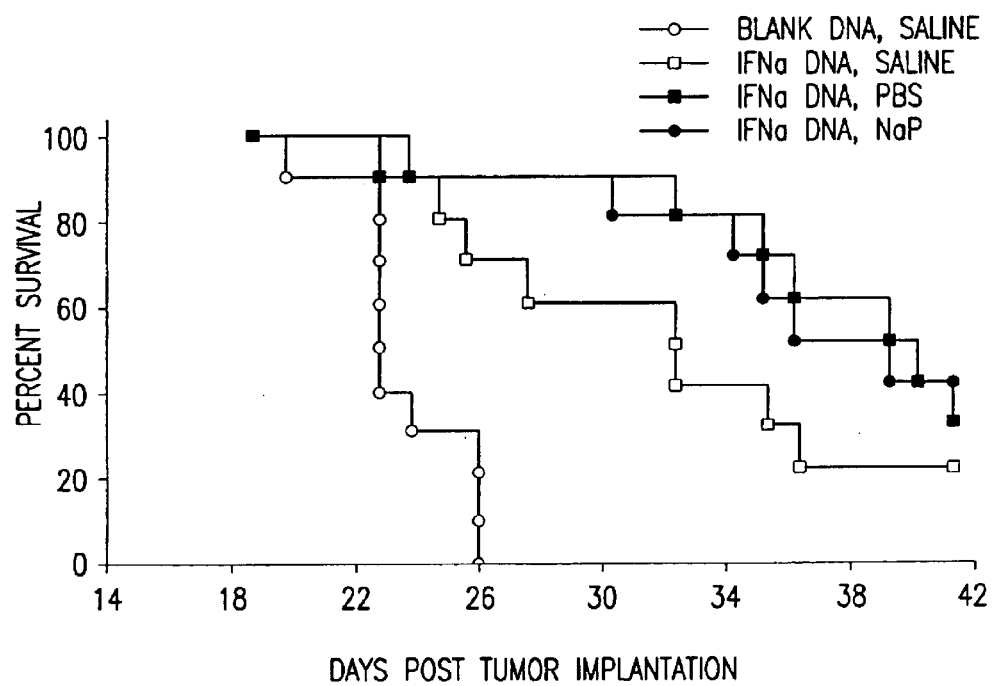

FIG. 17 shows that mice treated i.m. with 100 µg (50 µg/leg) of IFN-α plasmid DNA (VR4111) in the 150 mM sodium phosphate vehicle had a lower rate of tumor growth (FIG. 17A) and enhanced survival (FIG. 17B) compared with the groups treated with control DNA or VR4111 in saline or PBS.

Figure 18:
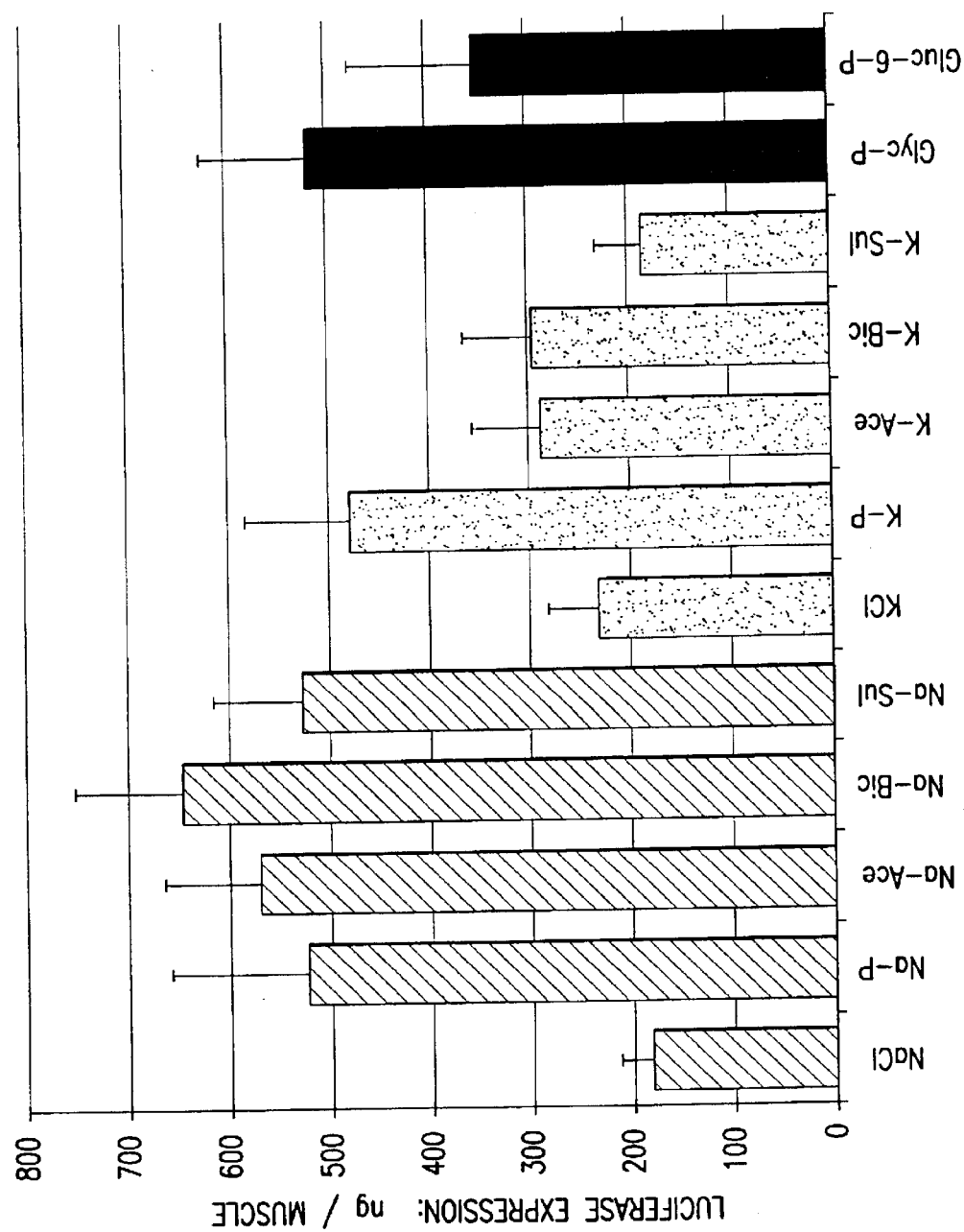

FIG. 18 is a bar graph showing the effect on luciferase expression in mouse muscle through the use of various sodium and potassium salt solutions. Fifty µg of plasmid VR1223 DNA per 50 µl of 150 mM solutions of the indicated sodium and potassium salts was injected into mouse quadriceps and the muscles were extracted and assayed for enzyme activity 7 days later. Bars represent Standard Error of the Mean (n=20 muscles per group). The various salts are as follows: 150 mM sodium chloride (NaCl); 150 mM sodium phosphate (Na—P); 150 mM sodium acetate (Na—Ace); 150 mM sodium bicarbonate (Na—Bic); 150 mM sodium sulfate (Na—Sul); 150 mM potassium chloride (KCl); 150 mM potassium phosphate (K—P); 150 mM potassium acetate (K—Ace); 150 mM potassium bicarbonate (K—Bic); 150 mM potassium sulfate (K—Sul); 150 mM glycero-phosphate, sodium salt (Glyc-P); and 150 mM glucose-6-phosphate, sodium salt (Gluc-6-).

Figure 19A:
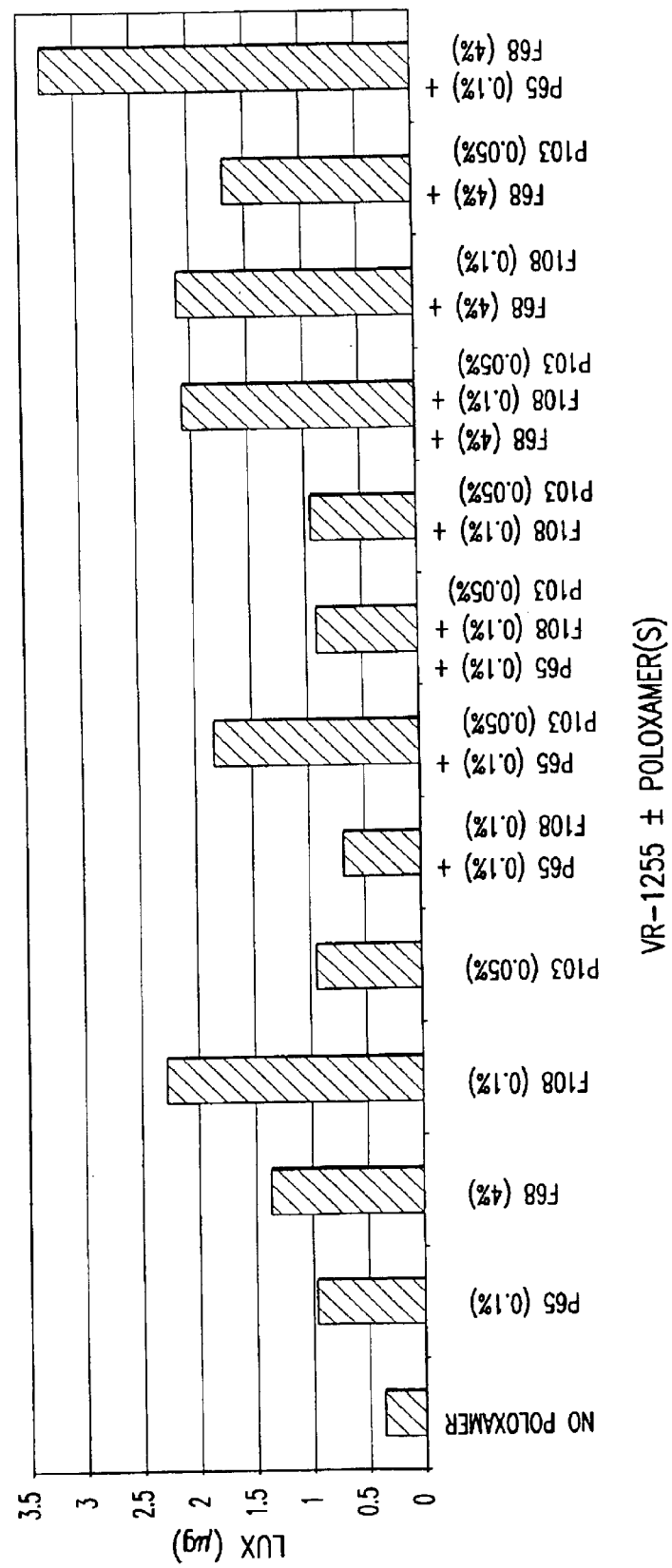

FIGS. 19A and B are bar graphs showing the effect of various combinations of auxiliary agents in a sodium phosphate solution on luciferase expression in mouse muscles. Fifty µg of plasmid VR1255 in 50 µl of 150 mM sodium phosphate either alone, containing a single auxiliary agent, or containing a combination of two or more auxiliary agents as indicated in the graph was injected into mouse quadriceps and the muscles were extracted and assayed for enzyme activity 7 days later. Certain auxiliary agent combinations enhanced luciferase expression by as much as 8.93 fold over that observed with 150 mM sodium phosphate solution alone (p=0.02).

Figure 20B:
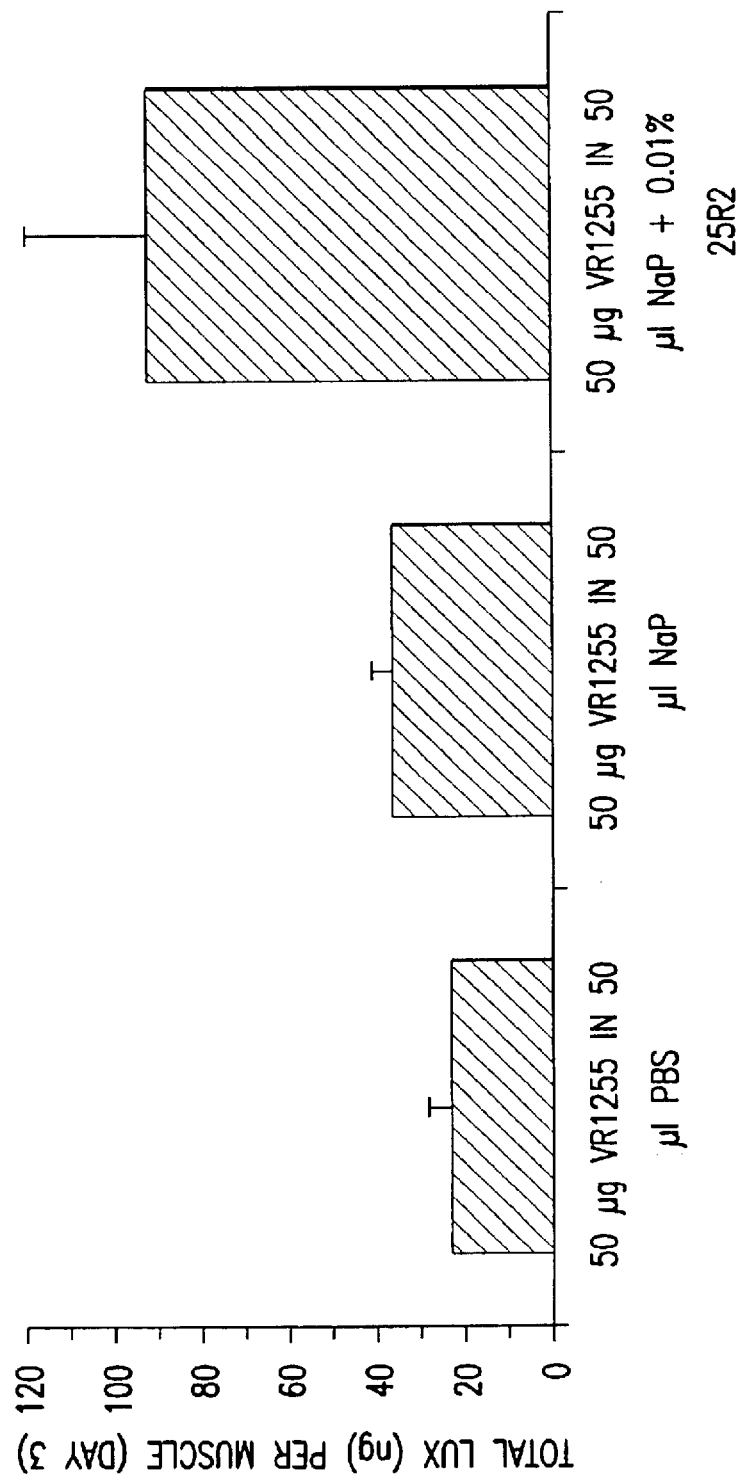

FIGS. 20A–B show the effect of adding an auxiliary agent into a sodium phosphate solution on luciferase expression in rat muscles. In FIG. 20A, ten µg of plasmid VR1255 in 10 µl of 150 mM sodium phosphate solution either alone (1 µg/µl DNA, n=8) or with added 4% (w/v) Pluronic® F68 (1 µg/µl DNA, n=8) was injected into rat quadriceps muscles. The muscles were collected 3 days later and assayed for enzyme activity. Compared to delivering the DNA in the sodium phoshate solution alone, DNA delivered in the sodium phosphate solution having the addedd Pluronic® F68 resulted in enhanced luciferase expression by 5-fold (p–0.003). In FIG. 20B, 50 µg of plasmid VR1255 in 50 µl of PBS, 150 mM sodium phosphate solution either alone (1 µg/µl DNA) or with added 0.01% (w/v) Pluronic® R 25R2 (1 µg/µl DNA) was injected into rat quadriceps muscles. The muscles were collected 3 days later and assayed for enzyme activity.

Figure 21:
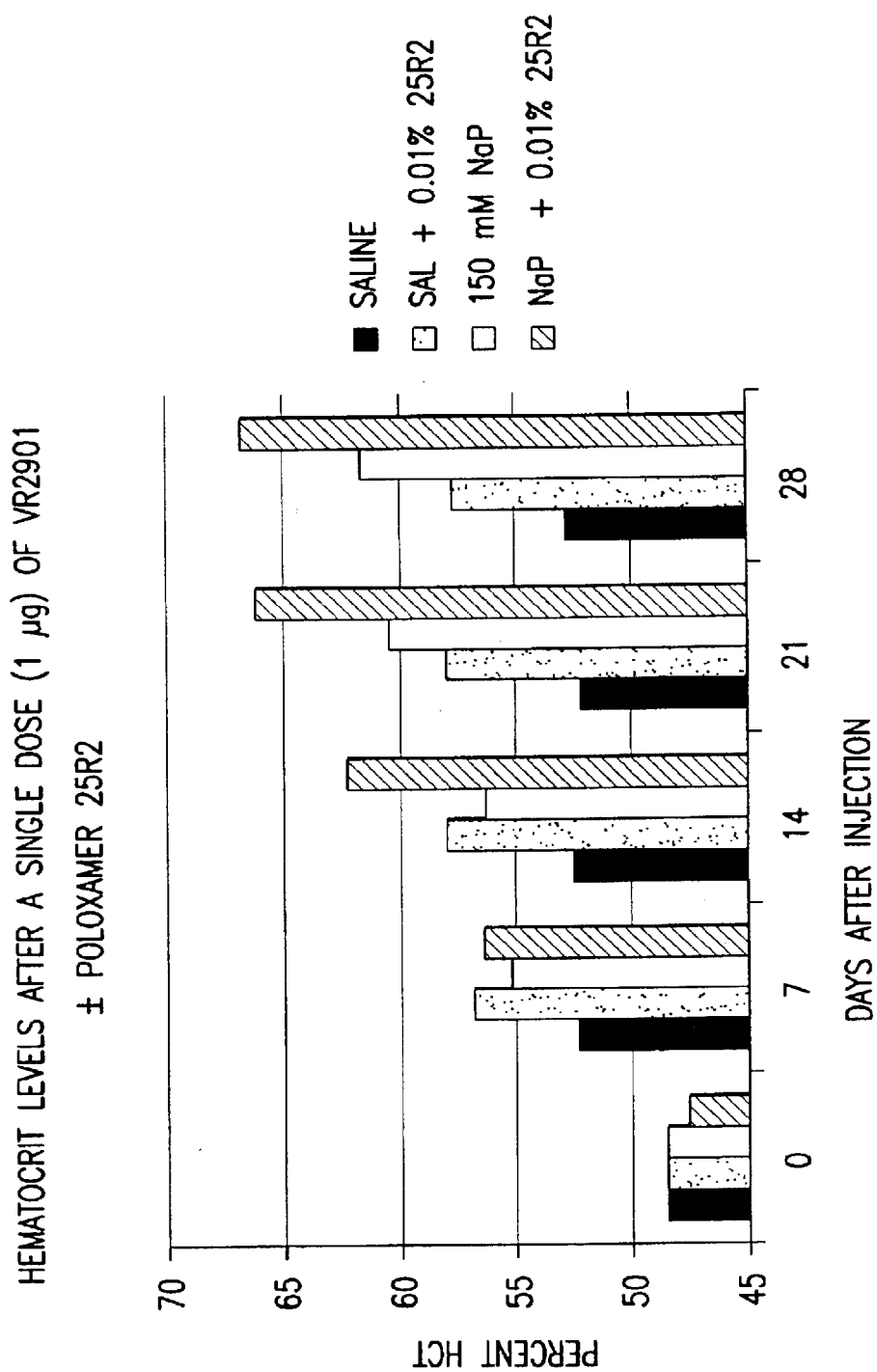

FIG. 21 illustrates the effect of an auxiliary agent on the biological activity of a therapeutic protein (erythropoietin). One µg of plasmid VR2901 DNA (or negative control VR1902 DNA) per 50 µl saline or 150 mM sodium phosphate solution alone, or containing 0.01% (w/v) Pluronic® R 25R2 was injected into BALB/c mouse quadriceps muscle (n=10 per group). At the indicated times after injection, serum was collected and hematocrits (HCT) measured as an indication of erythropoietin expression. There was a significant difference in hematocrit levels (p<0.05) on day 7 among mice injected with VR-2901 DNA in a vehicle of 150 mM sodium phosphate containing 0.01% Pluronic® R 25R2 compared to 150 mM sodium phosphate alone. There was a significant difference in hematocrit levels (p<0.05) in all time points assayed among mice injected with VR-2901 DNA in saline containing 0.01% Pluronic® R 25R2 compared to mice injected with saline alone.

Figure 22:
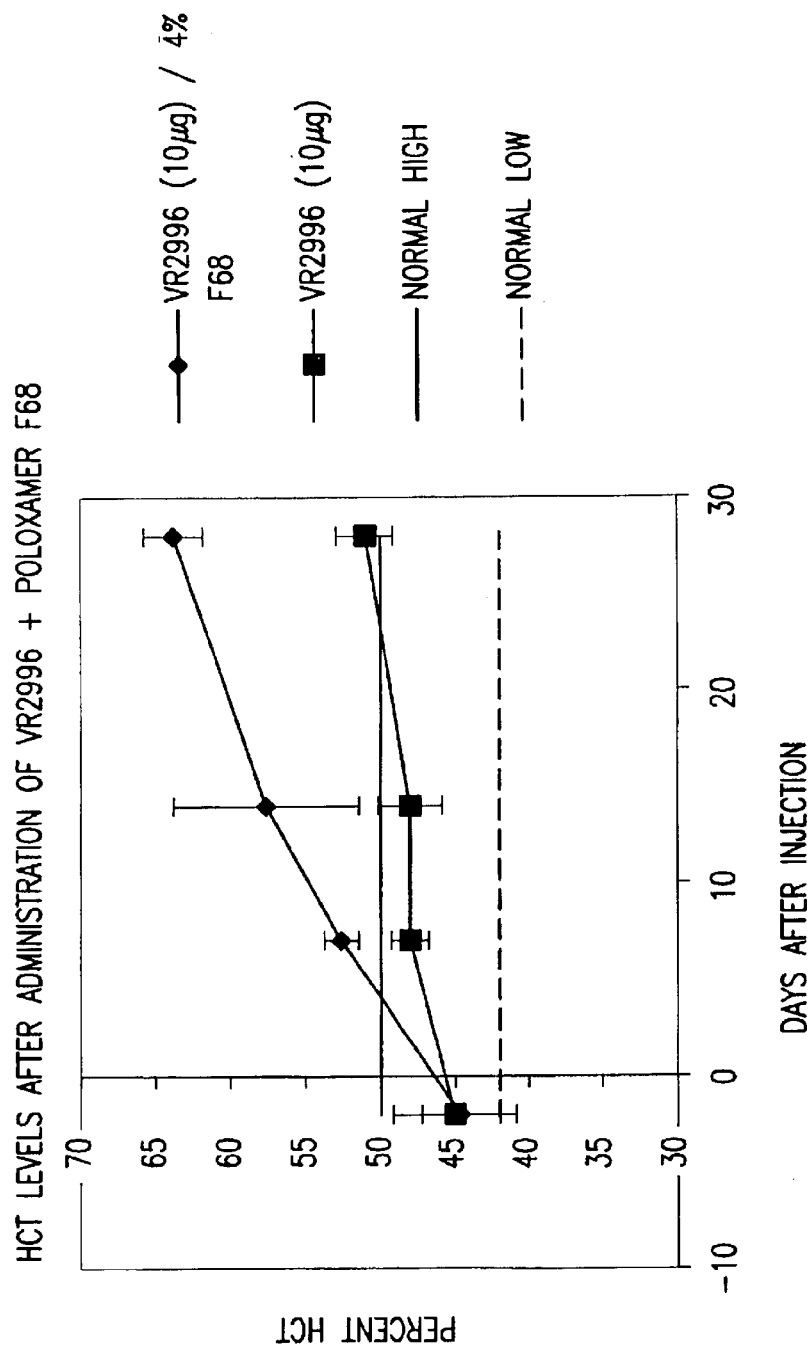

FIG. 22 illustrates the effect of another auxiliary agent on the biological activity of a therapeutic protein (erythropoietin). Ten µg of plasmid VR2996 DNA per 50 µl 150 mM sodium phosphate solution alone, or containing 4% (w/v) Pluronic® F68 was injected into BALB/c mouse quadriceps muscle. At the indicated times after injection, serum was collected and hematocrits (HCT) measured as an indication of erythropoietin expression.

Figure 23:
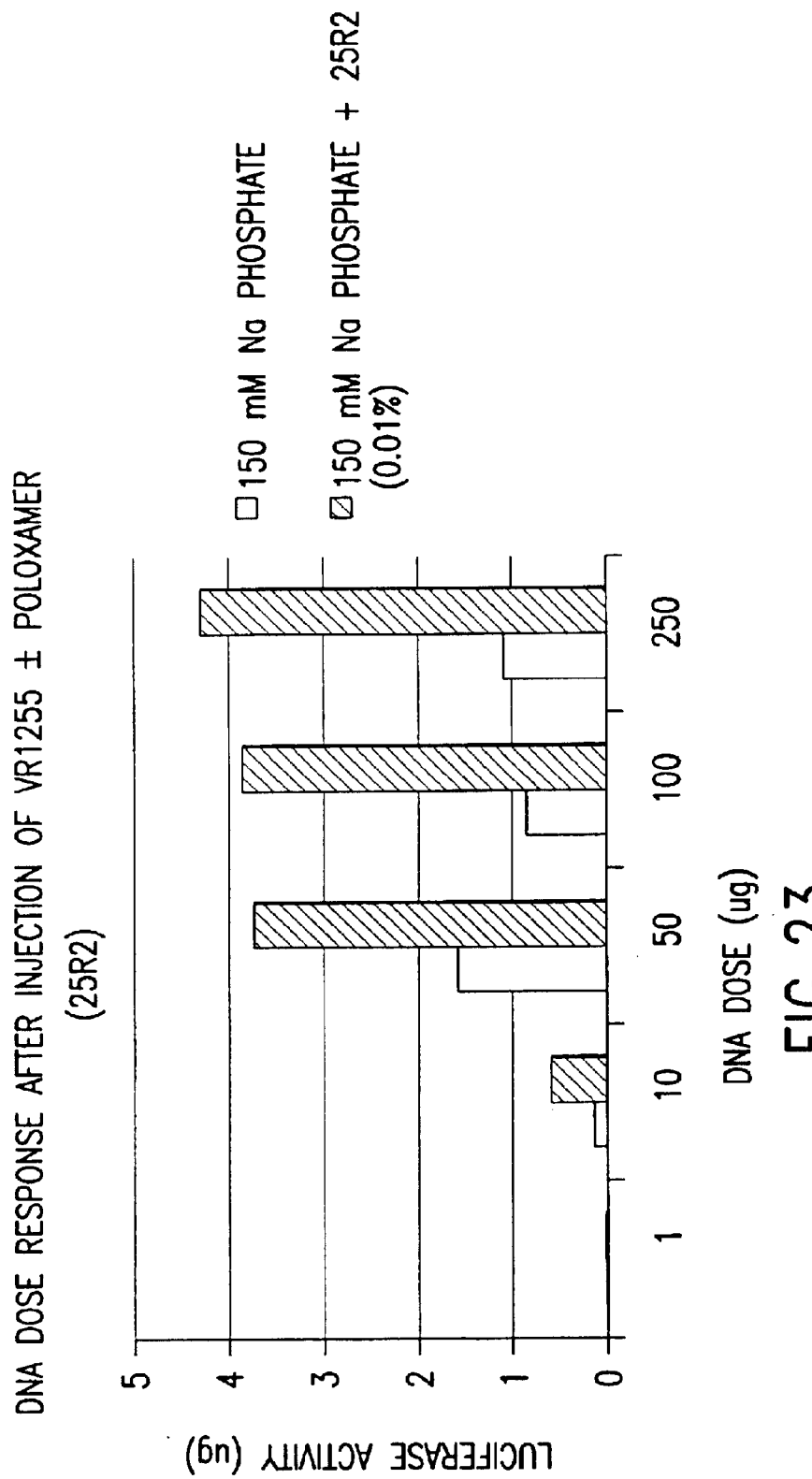

FIG. 23 is a bar graph showing a dose-response comparison of luciferase expression in mouse muscles plasmid DNA is injected in 150 mM sodium phosphate alone, or with 0.01% (w/v) of the auxiliary agent Pluronic® R25R2 added.

Figure 24:
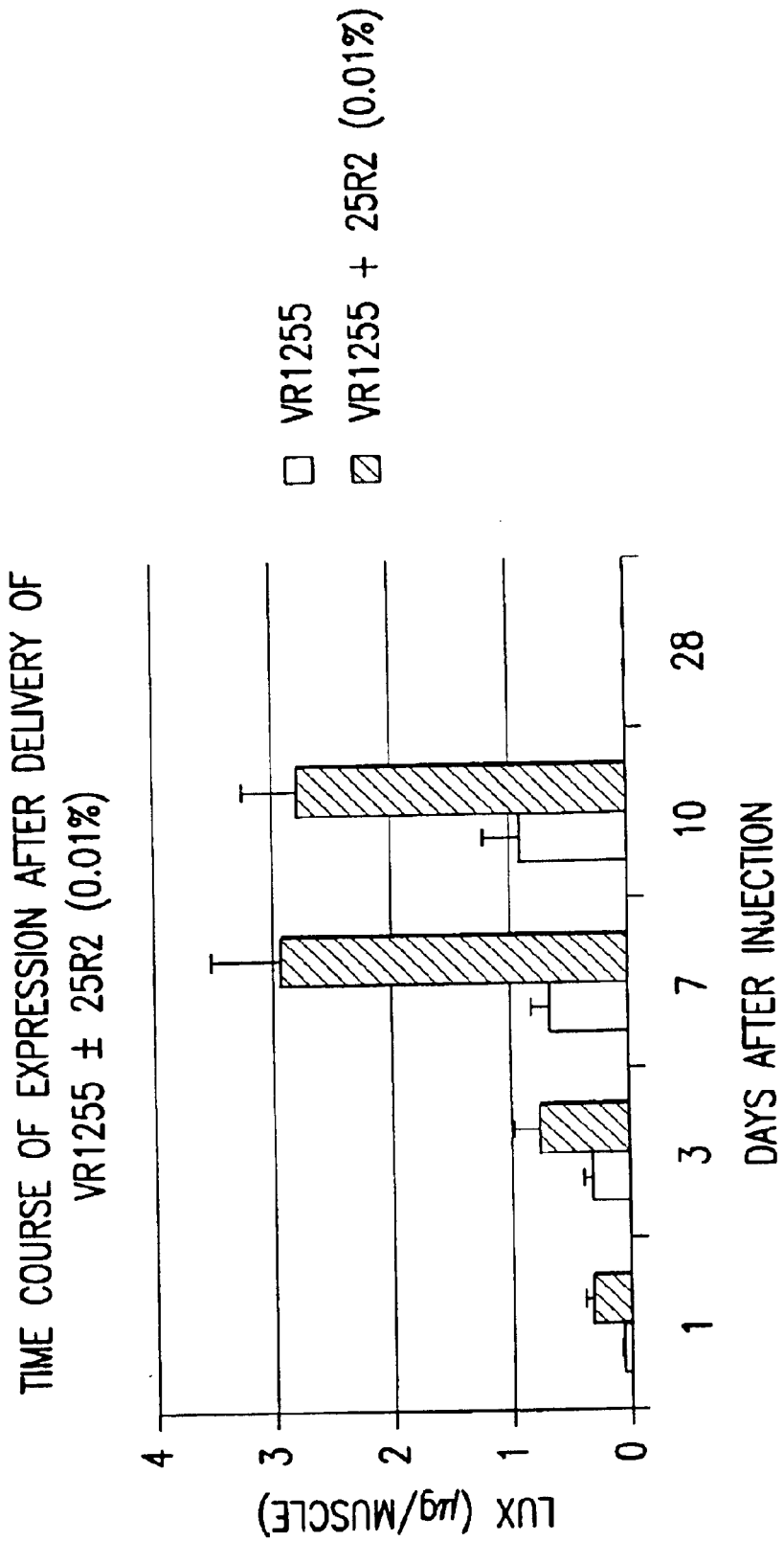

FIG. 24 is a bar graph showing a time course comparison of luciferase expression in mouse muscles when plasmid DNA is injected in 150 mM sodium phosphate alone, or with 0.01% (w/v) of the auxiliary agent Pluronic® R 25R2 added.

Figure 25:
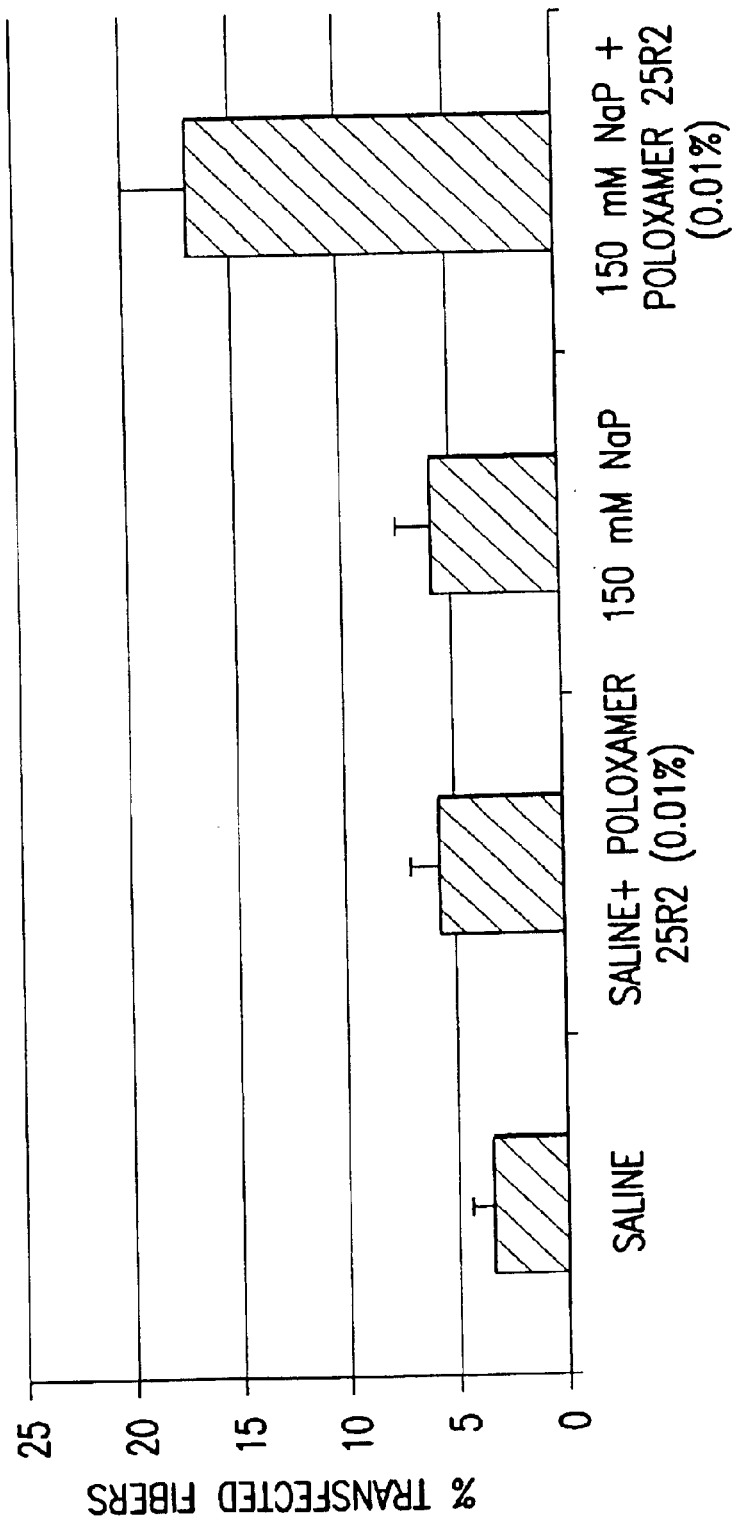

FIG. 25 is a bar graph showing the percentage of muscle fibers transfected with a beta-galactosidase-expressing plasmid DNA when the DNA is injected into mouse muscles either in saline or 150 mM sodium phosphate alone, or in saline or 150 mM sodium phosphate with 0.01% (w/v) of the auxiliary agent Pluronic® R 25R2 added.

Figure 26:
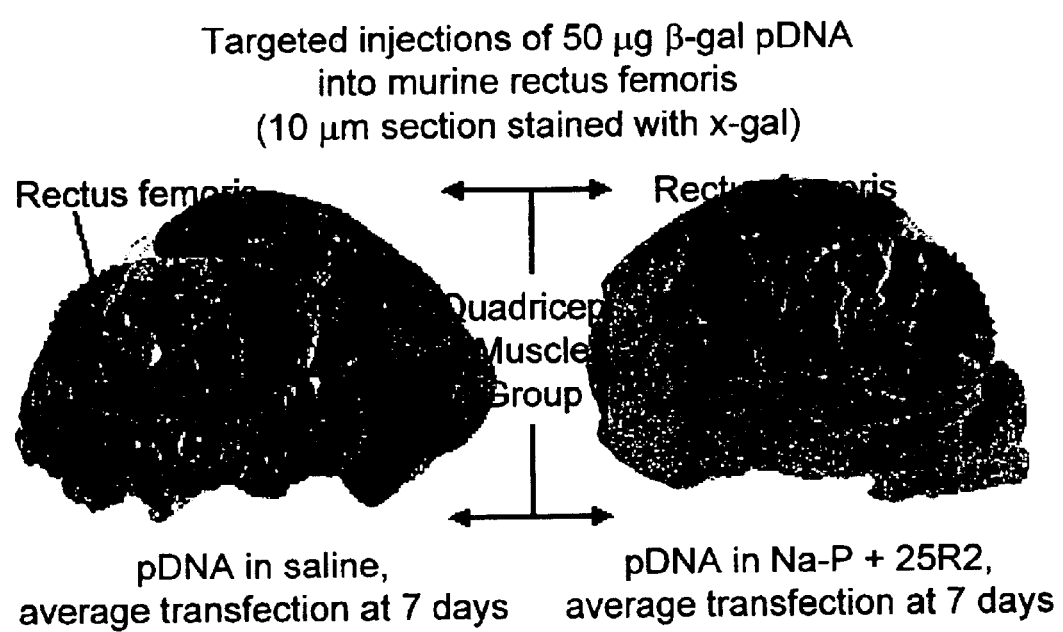

FIG. 26 shows micrographs of typical X-gal-stained muscle sections following plasmid DNA injection either in saline or in 150 mM sodium phosphate with 0.01% (w/v) of the auxiliary agent Pluronic® R 25R2 added.

DETAILED DESCRIPTION OF THE INVENTION

It will be apparent to one skilled in the art, in view of the following detailed description and the claims appended hereto, that various substitutions and modifications may be made to the present invention without departing from the scope of the invention as claimed.

The present invention is broadly directed to compositions and methods for improving the effectiveness of polypeptide delivery into a vertebrate by administering a polynucleotide encoding the polypeptide to the vertebrate's cells in vivo. Such compositions comprise a polypeptide-encoding polynucleotide, a salt, and/or an auxiliary agent, dissolved in an aqueous solution. In one preferred embodiment, about 1 ng to about 30 mg of a polynucleotide is dissolved in a solution of about 20 mM to about 300 mM sodium phosphate or about 20 mM to about 300 mM potassium phosphate. In another preferred embodiment, about 1 ng to about 30 mg of a polynucleotide is associated with a cationic lipid in an aqueous solution of about 0.1 to about 150 mM sodium phosphate or about 0.1 mM to about 150 mM potassium phosphate. In this embodiment, the aqueous solution is substantially free of chloride anion.

In other preferred embodiments, the polynucleotide is dissolved in any suitable aqueous solution, along with an auxiliary agent, preferably about 0.01 mM EDTA, about 0.01% (v/v) Triton X-114™, about 100 mM stachyose, about 0.1% (v/v) Tween 20®, about 0.001% (w/v) SDS, about 0.1% (v/v) Tween 80®, about 0.005% (v/v) IGEPAL CA 630®, about 0.01% (v/v) NONIDET NP-40®, about 0.01% (v/v) Triton X-100™, about 0.001% (v/v) DMSO, about 0.005% (v/v) Nonidet P40, about 0.5% (v/v) Pluronic® P65, about 1% (v/v) Pluronic® F77, about 4% (v/v) Pluronic® F68, about 0.01% (w/v) Pluronic® L64, about 0.01% (w/v) Pluronic® F108, or about 0.01% (w/v) Pluronic® R 25R2. In a more preferred embodiment, the polynucleotide is in an aqueous solution containing a salt, preferably a sodium phosphate or potassium phosphate and an auxiliary agent, preferably about 0.01 mM EDTA, about 0.01% (v/v) Triton X-114™, about 100 mM stachyose, about 0.1% (v/v) Tween 20®, about 0.001% (w/v) SDS, about 0.1% (v/v) Tween 80®, about 0.005% (v/v) IGEPAL CA 630®, about 0.01% (v/v) NONIDET NP-40®, about 0.01% (v/v) Triton X-100™M, about 0.001% (v/v) DMSO, about 0.005% (v/v) Nonidet P40, about 0.5% (v/v) Pluronic® P65, about 1% (v/v) Pluronic® F77, about 4% (v/v) Pluronic® F68, about 0.01% (w/v) Pluronic® L64, about 0.01% (w/v) Pluronic® F108, or about 0.01% (w/v) Pluronic® R 25R2.

In this manner, the present invention provides a method of enhancing the level of polypeptide expression from delivered polynucleotides in vivo and/or facilitating uptake of the polynucleotides by vertebrate cells. Delivery methods utilizing the compositions of the present invention significantly enhance the levels of in vivo transfection and in vivo polypeptide expression compared with traditional methods, i.e., delivery of a polypeptide-encoding polynucleotide in a solution of normal saline (about 154 mM NaCl) or phosphate buffered saline ("PBS": about 154 mM NaCl, about 10 mM sodium phosphate at pH 7.2).

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" may be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The term "vertebrate" is intended to encompass a singular "vertebrate" as well as plural "vertebrates," and comprises mammals and birds, as well as fish, reptiles, and amphibians.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; and bears. Preferably, the mammal is a domestic cat, a domestic dog, or a human subject. Most preferably, the mammal is a human subject.

As used herein, an "ion," an "ionic molecule," or an "ionic compound refers to an electrically charged atom, radical, molecule, or compound. By "radical" is meant a group of atoms that behaves as a single atom in a chemical reaction, for example, phosphate or ammonium. A "cation," a "cationic molecule", or a "cationic compound" refers to a positively charged molecule, radical, or compound, for example, $Na^+$ or $NH_4^+$. An "anion," an "anionic molecule," or an "anionic compound" refers to a negatively charged molecule, radical, or compound, for example, $Cl^-$, $PO_4^{3-}$ or $CH_3COO^-$. Cations and anions may have any number of positive or negative charges, respectively, i.e., they may be monovalent or multivalent, e.g., divalent or trivalent.

Anions can be either inorganic or organic, examples of the latter being pyruvate, citrate, or glycerophosphate anions. Cations of the present invention are limited to inorganic cations, with cationic molecules, radicals, or compounds comprising alkali metals (e.g., Li+, Na+, K+, Rb+) and alkaline earth metals (e.g., Mg++, Ca++, Sr++) being preferred.

As used herein a "salt" is a substance produced from the reaction between acids and bases which comprises a metal (cation) and a nonmetal (anion). For example, the base M-OH can be combined with the acid H-X to produce the salt M-X+$H_2O$. Salts can be "acid," i.e., having one or more unreplaced H atoms from the acid, e.g., $NaH_2PO_4$, "basic," i.e., containing unreplaced hydroxyl radicals of the base, e.g., $Bi(OH)Cl_2$, or mixed, i.e., containing two or more metals, e.g., $NaKHPO_4$. A net neutral valency is maintained between the cationic moiety and the anionic moiety. Salt crystals may be "hydrated" i.e., contain one or more water molecules. Such hydrated salts, when dissolved in an aqueous solution at a certain molar concentration, are equivalent to the corresponding anhydrous salt dissolved in an aqueous solution at the same molar concentration. For the present invention, salts which are readily soluble in an aqueous solution are preferred.

As used herein, a "salt" may be denoted as "M-X" regardless of the valency of the cations and anions making up the salt (as long as they balance), regardless of whether the salt is an acid salt, a basic salt, or a mixed salt, regardless of whether the anion is a radical, a molecule, or a compound, and regardless of whether the salt crystals are hydrated. For example, dibasic sodium phosphate ($Na_2HPO_4$), monobasic sodium phosphate ($NaH_2PO_4$), monobasic sodium potassium phosphate ($NaKHPO_4$), magnesium phosphate ($Mg_3(PO_4)_2 \cdot 4H_2O$), potassium acetate ($CH_3COOK$), and D(+)-α-sodium glycerophosphate ($HOCH_2CH(OH)CH_2OPO_3Na_2$) may all be denoted by the formula M-X. Alternatively, salts of the present invention may also be identified by the formula:

$$M^1{}_m M^2{}_n M^N{}_p H_q - X_r \cdot Y(H_2O)$$

Where $M^1$, $M^2$, and $M^N$ are one or more cationic molecules, radicals, or compounds, H is hydrogen, X is an anionic molecule, radical, or compound, and $H_2O$ is a water molecule, where m and r are integers greater than or equal to 1, and n, p, q, and Y are integers greater than or equal to 0. Applying this formula to the salt monobasic sodium potassium phosphate ($NaKHPO_4$), for example, $M^1$ is $Na^+$, $M^2$ is $K^+$, and X is $PO_4^{3-}$, m=1, n=1, p=0, q=1, r=1, and Y=0. The generic formulae "M-X" and "$M^1{}_m M^2{}_n M^N{}_p H_q - X_r \cdot Y(H_2O)$" may be used interchangeably herein.

The terms "saline" or "normal saline" as used herein refer to an aqueous solution of about 145 mM to about 155 mM sodium chloride, preferably about 154 mM sodium chloride. The terms "phosphate buffered saline" or "PBS" refer to an aqueous solution of about 145 mM to about 155 mM sodium chloride, preferably about 154 mM sodium chloride, and about 10 mM sodium phosphate, at a pH ranging from about 6.0 to 8.0, preferably at a pH ranging from about 6.5 to about 7.5, most preferably at pH 7.2.

Salts and Associated Formulations

Certain embodiments of the present invention comprise a salt of the formula M-X. As used herein, a "salt" of the present invention is a compound having a positively charged cation, M, and a negatively charged anion, X. Alternatively, the same salt may be designated by the formula $M^1{}_m M^2{}_n M^N{}_p H_q - X_r \cdot Y(H_2O)$, where $M^1$, $M^2$, and $M^N$ are one or more cationic molecules, radicals, or compounds, H is hydrogen, X is an anionic molecule, radical, or compound, and $H_2O$ is a water molecule, where m and r are integers greater than or equal to 1, and n, p, q, and Y are integers greater than or equal to 0. A salt may be in a solid crystalline form, but preferably for the present invention, is dissolved in an aqueous solution, i.e., liquid water. Accordingly, it is understood that salts which are readily soluble in water at the desired molar concentration are preferred.

The preferred cations for salts of the present invention include monovalent cations, and in particular the alkali metals, e.g, Li+, Na+, K+, Rb+. Most preferred cations are sodium, having the chemical symbol Na$^+$, and potassium, having the chemical symbol K$^+$. Anions of the salts of the present invention can be either inorganic anions or organic anions.

Preferred anions, designated herein by the symbol X, include phosphate, acetate, bicarbonate, sulfate and pyruvate, with phosphate being the most preferred. Other naturally occurring organic anions such as the intermediates in the Krebs Cycle (e.g., isocitrate, ketoglutarate, succinate, fumarate, malate, oxaloacetate) or the intermediates found in glycolysis (e.g., lactate, phosphoenolpyruvate) are also contemplated as the anions of the present invention.

An anion X can have an organic substituent attached thereto. Examples of organic anions include, but are not limited to, intermediates in the Krebs Cycle such as isocitrate, ketoglutarate, succinate, fumarate, malate, oxaloacetate, and other intermediates found in glycolysis such as lactate and phosphoenolpytruvate, as well as any other naturally occurring organic anion. For example, an organic monophosphate ester would be within the scope of this invention. By an "organic monophosphate ester" is meant an anion of the general formula R—PO$_4^2$, where R is any organic substituent. Examples of organic monophosphate esters include, but are not limited to β-D-glucose 1-phosphate glucose 6-phosphate, fructose 6-phosphate, fructose 1,6-diphosphate, β-D-galactose 1-phosphate, D-glyceraldeyde 3-phosphate, sn-glycerol 3-phosphate, glycerol 1-phosphate, α-glycerol phosphate, DL-α-glycerol phosphate, and dihydroxyacetone phosphate. Preferred phosphate esters include glucose-6-phosphate and DL-α-glycerol phosphate. Preferred organic monophosphate esters include sodium glucose 6-phosphate, and sodium DL-α-glycerol phosphate. Most preferred is the organic monophosphate ester DL-α-glycerol phosphate.

Preferred salts include sodium phosphate, sodium acetate, sodium bicarbonate, sodium sulfate, sodium pyruvate, potassium phosphate, potassium acetate, potassium bicarbonate, potassium sulfate, potassium pyruvate, disodium DL-α-glycero-phosphate, and disodium glucose-6-phosphate "Phosphate" salts of sodium or potassium can be either the monobasic form, e.g., NaHPO$_4$, or the dibasic form, e.g., Na$_2$HPO$_4$, but a mixture of the two, resulting in a desired pH, is most preferred. The most preferred salts are sodium phosphate or potassium phosphate. As used herein, the terms "sodium phosphate" or "potassium phosphate," refer to a mixture of the dibasic and monobasic forms of each salt to present at a given pH.

The pH values for salt solutions of the present invention can range from about pH 4 to about pH 10, depending on the properties of the particular salt solution. These pH values include about pH 4, about pH 4.5, about pH 5, about pH 5.5., about pH 6, about pH 6.5, about pH 7, about pH 7.5. about pH 8, about pH 8.5, about pH 9, about pH 9.5, and about pH 10. As used herein, the term "about" when referring to pH values indicates that the pH value may vary by as much as 0.4 pH units in either direction due to, for example, standard error or equipment error. Preferred pH values for a solution of sodium phosphate or potassium phosphate are from about pH 6 to about pH 8. More preferred pH values for a solution of sodium phosphate or potassium phosphate range from about pH 6.5 to about pH 7.5. Even more preferred pH values for a solution of sodium phosphate or potassium phosphate range from about 6.8 to about 7.4.

Salts of the present invention are preferably dissolved in aqueous solution at concentrations which enhance entry of a polypeptide-encoding polynucleotide into vertebrate cells in vivo, and/or enhance polypeptide expression, relative to saline, PBS, or water.

Certain embodiments of the present invention are drawn to compositions comprising about 1 ng to about 30 mg of a polynucleotide in aqueous solution, where the polynucleotide operably encodes a polypeptide within vertebrate cells in vivo; and a salt M-X dissolved in the aqueous solution at a molar concentration from about 20 mM to about 300 mM, and reaction, association, or dissociation products thereof, where M is an alkali metal (e.g., Li+, Na+, K+, Rb+), preferably sodium and potassium, and where X is an anion selected from the group consisting of phosphate, acetate, bicarbonate, sulfate, pyruvate, and an organic monophosphate ester, preferably glucose 6-phosphate or DL-α-glycerol phosphate. The present invention is further drawn to methods to use such a composition, methods to make such a composition, and pharmaceutical kits.

The term "a salt dissolved in aqueous solution at a given molar concentration" means that the molecular mass, e.g., in grams, of a crystallized form of that salt required to produce a given volume of a solution of a given molar concentration is calculated based on the molecular weight of the particular crystalline form. It should be noted that a hydrated crystalline form of a salt will have a larger molecular weight, i.e., grams per mole, than a corresponding anhydrous form of the same salt, so a greater amount, in grams, will be required to achieve an equivalent molar concentration in aqueous solution. The appropriate amount of crystals is weighed out using standard laboratory procedures, the crystals are added to a volume of water or other aqueous solution which is slightly less than the final desired volume, the liquid is mixed until the crystals are fully dissolved, and then the volume of the liquid is brought up to the final desired volume.

The term "reaction, association, or dissociation products thereof" refers to any ionic interactions which may be formed in the aqueous solution once the salt crystals are dissolved. For example, once a salt is dissolved in an aqueous solution, the cations and anions disassociate and are free in solution to interact with other cations or anions that may be present in the solution, including, for example, a negatively-charged polynucleotide molecule. The interactions taking place in a complex aqueous salt solution, except for the precipitation of insoluble salt complexes, are transient and reversible, and cannot be precisely predicted at any point in time. Therefore, once an aqueous solution comprising a salt at a certain molar concentration is prepared, the interactions in the solution may include reaction products other than the interaction of the cation and anion which composed the salt crystals that were added to the solution as described above.

Preferably in the present embodiment, the salt M-X is dissolved in aqueous solution at a molar concentration ranging from about 25 mM to about 290 mM, from about 30 mM to about 280 mM, from about 35 mM to about 270 mM, from about 40 mM to about 260 mM, from about 45 mM to about 255 mM, from about 50 mM to about 250 mM, from about 55 mM to about 245 mM, from about 60 mM to about 240 mM, from about 65 mM to about 235 mM, from about 70 mM to about 230 mM, from about 75 mM to about 225 mM, from about 80 mM to about 220 mM, from about 85 mM to about 215 mM, from about 90 mM to about 210 mM, from about 95 mM to about 205 mM, from about 100 mM to about 200 mM, from about 105 mM to about 195 mM, from about 110 mM to about 190 mM, from about 115 mM to about 185 mM, from about 120 mM to about 180 mM, from about 125 mM to about 175 mM, from about 130 mM to about 170 mM, from about 135 mM to about 165 mM, from about 140 mM to about 160 mM, and from about 145 mM to about 155 mM.

In other preferred compositions of the present embodiment, the salt M-X is dissolved in aqueous solution at a molar concentration ranging from about 20 mM to about 90 mM, from about 30 mM to about 90 mM, from about 40 mM to about 90 mM, from about 50 mM to about 90 mM, from about 60 mM to about 90 mM, from about 70 mM to about 90 mM, from about 80 mM to about 90 mM, from about 20 mM to about 95 mM, from about 30 mM to about 95 mM, from about 40 mM to about 95 mM, from about 50 mM to about 95 mM, from about 60 mM to about 95 mM, from about 70 mM to about 95 mM, from about 80 mM to about 95 mM, from about 105 mM to about 300 mM, from about 105 mM to about 200 mM, from about 105 mM to about 190 mM, from about 105 mM to about 180 mM, from about 105 mM to about 170 mM, from about 105 mM to about 160 mM, from about 105 mM to about 155 mM, from about 105 mM to about 150 mM, from about 110 mM to about 300 mM, from about 110 mM to about 200 mM, from about 110 mM to about 190 mM, from about 110 mM to about 180 mM, from about 110 mM to about 170 mM, from about 110 mM to about 160 mM, from about 110 mM to about 155 mM, from about 110 mM to about 150 mM, from about 155 mM to about 300 mM, from about 155 mM to about 200 mM, from about 155 mM to about 195 mM, from about 155 mM to about 190 mM, from about 155 mM to about 185 mM, from about 155 mM to about 180 mM, from about 155 mM to about 175 mM, from about 155 mM to about 170 mM, from about 155 mM to about 165 mM, from about 155 mM to about 160 mM, from about 160 mM to about 300 mM, from about 160 mM to about 200 mM, from about 160 mM to about 195 mM, from about 160 mM to about 190 mM, from about 160 mM to about 185 mM, from about 160 mM to about 180 mM, from about 160 mM to about 175 mM, from about 160 mM to about 170 mM, and from about 160 mM to about 165 mM.

More preferably in the present embodiment, the salt M-X is dissolved in aqueous solution at a molar concentration of about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130mM, about 135 mM, about 140 mM, about 145 mM, about 150 mM, about 155 mM, about 160 mM, about 165 mM, about 170 mM, about 175 mM, about 180 mM, about 185 mM, about 190 mM, about 200 mM, about 205 mM, about 210 mM, about 215 mM, about 220 mM, about 225 mM, about 230 mM, about 235 mM, about 240 mM, about 245 mM, about 250 mM, about 255 mM, about 260 mM, about 265 mM, about 270 mM, about 275 mM, about 280 mM, about 285 mM, about 290 mM, about 295 mM, and about 300 mM.

Even more preferably in the present embodiment, the salt M-X is dissolved in aqueous solution at a molar concentration of about 100 to about 200 mM. Most preferably, the salt M-X is dissolved in aqueous solution at a molar concentration of about 150 mM.

As used herein, a phrase such as "a molar concentration of about 150 mM" refers to the range of molar concentrations approaching 150 mM to the best approximation obtainable by one of ordinary skill in the art using standard laboratory equipment and methods. For example, "the salt sodium phosphate dissolved in aqueous solution of about 150 mM," prepared using ordinary laboratory balances and measuring glassware, and using generally accepted techniques, may range anywhere from approximately 145 mM to approximately 155 mM based on the standard error inherent in preparing chemical solutions. Such a standard error range would be well understood by one of ordinary skill in the art to be equivalent to "about 150 mM."

According to the present embodiment, compositions comprising about 1 ng to about 30 mg of a polynucleotide in aqueous solution and a salt M-X dissolved in the aqueous solution at a molar concentration from about 20 mM to about 300 mM as described above may further comprise chloride ion, represented by the symbol Cl$^-$, in the aqueous solution at a molar equivalent concentration of 0 (zero) mM to about 125 mM. By "molar equivalent" is meant the molar concentration of chloride ion in solution, as opposed to the molar concentration of the salt added to the aqueous solution. For example, chloride ion may be added to the aqueous solution as part of certain salt crystals dissolved in the solution, such as sodium chloride (NaCl) or calcium chloride ($CaCl_2$). Each mole of sodium chloride crystals added to an aqueous solution will add one mole equivalent of chloride ion to the solution, where each mole of calcium chloride crystals added to an aqueous solution will add two mole equivalents of chloride ion to the solution. Alternatively, chloride ion may be added to the aqueous solution as part of an acid or base such as hydrochloric acid or ammonium chloride.

Preferably, chloride ion is present in the aqueous solution at a molar equivalent concentration ranging from 0 mM to about 120 mM, from 0 mM to about 115 mM, from 0 mM to about 110 mM, from 0 mM to about 105 mM, from 0 mM to about 100 mM, from 0 mM to about 95 mM, from 0 mM to about 90 mM, from 0 mM to about 85 mM, from 0 mM to about 80 mM, from 0 mM to about 75 mM, from 0 mM to about 70 mM, from 0 mM to about 65 mM, from 0 mM to about 60 mM, from 0 mM to about 55 mM, from 0 mM to about 50 mM, from 0 mM to about 45 mM, from 0 mM to about 40 mM, from 0 mM to about 35 mM, from 0 mM to about 30 mM, from 0 mM to about 25 mM, from 0 mM to about 20 mM, from 0 mM to about 15 mM, from 0 mM to about 10 mM, or from 0 mM to about 5 mM.

More preferably, chloride ion is present in the aqueous solution at a molar concentration of about 120 mM, about 115 mM, about 110 mM, about 105 mM, about 100 mM, about 95 mM, about 90 mM, about 85 mM, about 80 mM, about 75 mM, about 70 mM, about 65 mM, about 60 mM, about 55 mM, about 50 mM, about 45 mM, about 40 mM, about 35 mM, about 30 mM, about 25 mM, about 20 mM, about 15 mM, about 10 mM, about 5 mM, or 0 mM.

Most preferably, the aqueous solution is substantially free of chloride ion. As used herein, the phrase "substantially free of chloride ion" indicates that the amount of chloride ion added into the composition is insubstantial and that the addition cannot alter the transcription- and/or expression-enhancing activity of the composition at a significant level. The phrase "essentially free of chloride ion" indicates that no source of chloride ion is intentionally added to the composition other than as an incidental but integral part of the another reagent being added to the solution. An example, without limiting the scope of the exclusion, would be addition of chloride present as the counterion to a propaniminum based cationic lipid. In addition, some chloride ion may be present due to, for example, impurities in other components of the composition.

In certain embodiments, described in more detail below, compositions of the present invention may further comprise one or more transfection facilitating materials including, but not limited to, materials such as cationic lipids, calcium phosphate, alum, gold, tungsten, or other metal particles, peptides, proteins, and polymers. However, compositions of the present embodiment, which comprise a polynucleotide in aqueous solution and a salt M-X dissolved in the aqueous solution at a molar concentration from about 20 mM to about 300 mM as described above, are preferably free of cationic lipids.

Accordingly a preferred embodiment of the present invention is a composition comprising: about 1 ng to about 30 mg of a polynucleotide in aqueous solution, where the polynucleotide operably encodes a polypeptide within vertebrate cells in vivo; a salt M-X dissolved in the aqueous solution at a molar concentration from about 20 mM to about 300 mM, and reaction, association, or dissociation products thereof, where M is an alkali metal (e.g., Li+, Na+, K+, Rb+), preferably sodium and potassium, and where X is an anion selected from the group consisting of phosphate, acetate, bicarbonate, sulfate, pyruvate, and an organic monophosphate ester, preferably glucose 6-phosphate or DL-α-glycerol phosphate; and where the composition is free of cationic lipids.

Further embodiments of the present invention are drawn to compositions comprising: about 1 ng to about 30 mg of a polynucleotide in aqueous solution, where the polynucleotide operably encodes a polypeptide within vertebrate cells in vivo; a salt M-X dissolved in the aqueous solution at a molar concentration from about 0.1 mM to about 150 mM, and reaction, association, or dissociation products thereof, where M is an alkali metal (e.g., Li+, Na+, K+, Rb+), preferably sodium and potassium, and where X is an anion selected from the group consisting of phosphate, acetate, bicarbonate, sulfate, pyruvate, and an organic monophosphate ester, preferably glucose 6-phosphate or DL-α-glycerol phosphate; a cationic lipid suspended in said aqueous solution; and where the aqueous solution is substantially free of chloride anion. The present invention is further drawn to methods to use such a composition, methods to make such a composition, and pharmaceutical kits.

Preferably, the salt M-X is dissolved in aqueous solution at a molar concentration ranging from about 0.1 mM to about 145 mM, from about 0.1 mM to about 140 mM, from about 0.1 mM to about 135 mM, from about 0.1 mM to about 130 mM, from about 0.1 mM to about 125 mM, from about 1 mM to about 120 mM, from about 1 mM to about 115 mM, from about 1 mM to about 110 mM, from about 1 mM to about 105 mM, from about 1 mM to about 100 mM, from about 1 mM to about 95 mM, from about 1 mM to about 90 mM, from about 1 mM to about 85 mM, from about 1 mM to about 80 mM, from about 1 mM to about 75 mM, from about 1 mM to about 70 mM, from about 1 mM to about 65 mM, from about 1 mM to about 60 mM, from about 1 mM to about 55 mM, from about 1 mM to about 50 mM, from about 1 mM to about 45 mM, from about 1 mM to about 40 mM, from about 1 mM to about 35 mM, from about 1 mM to about 30 mM, from about 1 mM to about 25 mM, from about 1 mM to about 20 mM, from about 1 mM to about 15 mM, from about 1 mM to about 10 mM, from about 1 mM to about 5 mM, from about 1 mM to about 4.0 mM, from about 1 mM to about 3.0 mM, or from about 1 mM to about 2.5 mM.

More preferably, the salt M-X is dissolved in aqueous solution at a molar concentration of about 145 mM, about 140 mM, about 135 mM, about 130 mM, about 125 mM, about 120 mM, about 115 mM, about 110 mM, about 105 mM, about 100 mM, about 95 mM, about 90 mM, about 85 mM, about 80 mM, about 75 mM, about 70 mM, about 65 mM, about 60 mM, about 55 mM, about 50 mM, about 45 mM, about 40 mM, about 35 mM, about 30 mM, about 25 mM, about 20 mM, about 15 mM, about 10 mM, about 5 mM, about 4.0 mM, about 3.0 mM, about 2.5 mM, about 2.0 mM, about 1.5 mM, about 1.0 mM, about 0.5 mM, or about 0.1 mM.

Even more preferably, the salt M-X is dissolved in aqueous solution at a molar concentration of about 1 mM to 10 mM, with about 2.5 mM being most preferred.

Those embodiments of the present invention comprising a salt M-X dissolved in the aqueous solution at a molar concentration from about 0.1 mM to about 150 mM, and which are substantially free of chloride ion also comprise a cationic lipid suspended in the aqueous solution. Cationic lipids are described in more detail in the section below on "transfection facilitating agents." While not being bound by theory, cationic lipids are thought to interact with anionic polynucleotide molecules in solution, and the complexes formed thereby are thought to have an improved ability to enter into vertebrate cells.

Certain preferred embodiments of the present invention include a composition comprising: about 1 ng to about 30 mg of a polynucleotide in aqueous solution, where the polynucleotide operably encodes a polypeptide within vertebrate cells in vivo, and where the polynucleotide is complexed with a cationic lipid; and a salt M-X dissolved in the aqueous solution at a molar concentration from about 0.1 mM to about 150 mM, and reaction, association, or dissociation products thereof, where M is an alkali metal (e.g., Li+, Na+, K+, Rb+), preferably sodium and potassium, where X is an anion selected from the group consisting of phosphate, acetate, sulfate, and pyruvate; and where the aqueous solution is substantially free of added chloride anion and bicarbonate ion, i.e. $HCO_3^{2-}$ and/or $H_2CO_{3-}$. The term "substantially free" is defined supra. For example, the presence of carbonate in the aqueous composition as a consequence of atmospheric equilibration would be considered insubstantial.

That certain of the salts and salt solutions disclosed herein were effective in increasing expression of polypeptides encoded by polynucleotides delivered to vertebrate cells in vivo relative to saline or PBS was unexpected in view of results showing that other salt solutions have no enhancing effect on expression of polypeptides encoded by polynucleotides delivered to vertebrate cells in vivo, or even hinder such expression. For example, the following salt solutions had no ability to enhance, relative to a salt solution consisting essentially of normal saline, the entry of polynucleotides into vertebrate cells in vivo, and/or the in vivo expression of polypeptides encoded by such polynucleotides: 150 mM potassium chloride, 150 mM magnesium chloride, 150 mM calcium chloride, 150 mM zinc chloride, 150 mM ferrous chloride, 150 mM magnesium phosphate, 150 mM calcium phosphate, 150 mM aluminum phosphate, 150 mM ferric phosphate, 150 mM sodium citrate, and 150 mM sodium oxalate. See Table II.

Auxiliary Agents

Additional embodiments of the present invention are drawn to compositions comprising an auxiliary agent. The present invention is further drawn to methods to use such compositions, methods to make such compositions, and pharmaceutical kits. As used herein, an "auxiliary agent" is a substance included in a composition for its ability to enhance, relative to a composition which is identical except for the inclusion of the auxiliary agent, the entry of polynucleotides into vertebrate cells in vivo, and/or the in vivo expression of polypeptides encoded by such polynucleotides. Auxiliary agents of the present invention include nonionic, anionic, cationic, or zwitterionic surfactants or detergents, with nonionic surfactants or detergents being preferred, chelators, DNase inhibitors, agents that aggregate or condense nucleic acids, emulsifying or solubilizing agents, wetting agents, gel-forming agents, and buffers.

While not being bound by theory, the inventors believe that surfactants, detergents and emulsifying or solubilizing agents may exert their effects by protecting the polynucleotide, or condensing the polynucleotide to reduce its size or volume, increasing membrane permeability through the plasma membrane or the nuclear membrane, or solubilizing the extracellular matrix or basal lamina. An emulsifying agent may form an emulsion with the polynucleotide to allow better penetration. Agents that condense or aggregate nucleic acids may exert their effects by decreasing the size (volume) of the DNA and increasing the amount of the polynucleotide that enters cells or may provide a carrier effect for the polynucleotide. DNase inhibitors may exert their effect by protecting DNA from degradation. Buffers or chelating agents may exert their effect by altering calcium levels affecting membrane resealing properties.

Auxiliary agents of the present invention include nonionic detergents and surfactants such as poloxamers. Poloxamers are a series of non-ionic surfactants that are block copolymers of ethylene oxide and propylene oxide. The poly(oxyethylene) segment is hydrophillic and the poly (oxypropylene) segment is hydrophobic. The physical forms are liquids, pastes or solids. The molecular weight ranges from 1000 to greater than 16000. The basic structure of a poloxamer is HO—$(CH_2CH_2O)_x$—$[CH_2CHO(CH_3)]_y$—$(CH_2CH_2O)_x$—H, where x and y represent repeating units of ethylene oxide and propylene oxide respectively. Thus, the propylene oxide (PO) segment is sandwiched between two ethylene oxide (EO) segments, (EO—PO—EO). The number of x's and y's distinguishes individual poloxamers. If the ethylene oxide segment is sandwiched between two propylene oxide segments, (PO—EO—PO), then the resulting structure is a reverse poloxamer. The basic structure of a reverse poloxamer is HO—$[CH(CH_3)CH_2O)_x]$—$(CH_2CH_2O)_y$—$[CH_2CHO(CH_3)]_x$—H.

Poloxamers of the present invention include, but are not limited to commercially available poloxamers such as Pluronic® L121 (ave. MW: 4400; approx. MW of hydrophobe, 3600; approx. wt. % of hydrophile, 10%), Pluronic® L101 (ave. MW: 3800; approx. MW of hydrophobe, 3000; approx. wt. % of hydrophile, 10%), Pluronic® L8 1 (ave. MW: 2750; approx. MW of hydrophobe, 2400; approx. wt. % of hydrophile, 10%), Pluronic® L61 (ave. MW: 2000; approx. MW of hydrophobe, 1800; approx. wt. % of hydrophile, 10%), Pluronic® L31 (ave. MW: 1100; approx. MW of hydrophobe, 900; approx. wt. % of hydrophile, 10%), Pluronic® L122 (ave. MW: 5000; approx. MW of hydrophobe, 3600; approx. wt. % of hydrophile, 20%), Pluronic® L92 (ave. MW: 3650; approx. MW of hydrophobe, 2700; approx. wt. % of hydrophile, 20%), Pluronic® L72 (ave. MW: 2750; approx. MW of hydrophobe, 2100; approx. wt. % of hydrophile, 20%), Pluronic® L62 (ave. MW: 2500; approx. MW of hydrophobe, 1800; approx. wt. % of hydrophile, 20%), Pluronic® L42 (ave. MW: 1630; approx. MW of hydrophobe, 1200; approx. wt. % of hydrophile, 20%), Pluronic® L63 (ave. MW: 2650; approx. MW of hydrophobe, 1800; approx. wt. % of hydrophile, 30%), Pluronic® L43 (ave. MW: 1850; approx. MW of hydrophobe, 1200; approx. wt. % of hydrophile, 30%), Pluronic® L64 (ave. MW: 2900; approx. MW of hydrophobe, 1800; approx. wt. % of hydrophile, 40%), Pluronic® L44 (ave. MW: 2200; approx. MW of hydrophobe, 1200; approx. wt. % of hydrophile, 40%), Pluronic® L35 (ave. MW: 1900; approx. MW of hydrophobe, 900; approx. wt. % of hydrophile, 50%), Pluronic® P123 (ave. MW: 5750; approx. MW of hydrophobe, 3600; approx. wt. % of hydrophile, 30%), Pluronic® P103 (ave. MW: 4950; approx. MW of hydrophobe, 3000; approx. wt. % of hydrophile, 30%), Pluronic® P104 (ave. MW: 5900; approx. MW of hydrophobe, 3000; approx. wt. % of hydrophile, 40%), Pluronic® P84 (ave. MW: 4200; approx. MW of hydrophobe, 2400; approx. wt. % of hydrophile, 40%), Pluronic® P105 (ave. MW: 6500; approx. MW of hydrophobe, 3000; approx. wt. % of hydrophile, 50%), Pluronic® P85 (ave. MW: 4600; approx. MW of hydrophobe, 2400; approx. wt. % of hydrophile, 50%), Pluronic® P75 (ave. MW: 4150; approx. MW of hydrophobe, 2100; approx. wt. % of hydrophile, 50%), Pluronic® P65 (ave. MW: 3400; approx. MW of hydrophobe, 1800; approx. wt. % of hydrophile, 50%), Pluronic® F127 (ave. MW: 12600; approx. MW of hydrophobe, 3600; approx. wt. % of hydrophile, 70%), Pluronic® F98 (ave. MW: 13000; approx. MW of hydrophobe, 2700; approx. wt. % of hydrophile, 80%), Pluronic® F87 (ave. MW: 7700; approx. MW of hydrophobe, 2400; approx. wt. % of hydrophile, 70%), Pluronic® F77 (ave. MW: 6600; approx. MW of hydrophobe, 2100; approx. wt. % of hydrophile, 70%), Pluronic® F108 (ave. MW: 14600; approx. MW of hydrophobe, 3000; approx. wt. % of hydrophile, 80%), Pluronic® F98 (ave. MW: 13000; approx. MW of hydrophobe, 2700; approx. wt. % of hydrophile, 80%), Pluronic® F88 (ave. MW: 11400; approx. MW of hydrophobe, 2400; approx. wt. % of hydrophile, 80%), Pluronic® F68 (ave. MW: 8400; approx. MW of hydrophobe, 1800; approx. wt. % of hydrophile, 80%), Pluronic® F38 (ave. MW: 4700; approx. MW of hydrophobe, 900; approx. wt. % of hydrophile, 80%).

Reverse poloxamers of the present invention include, but are not limited to Pluronic® R 31R1 (ave. MW: 3250; approx. MW of hydrophobe, 3100; approx. wt. % of hydrophile, 10%), Pluronic® R 25R1 (ave. MW: 2700; approx. MW of hydrophobe, 2500; approx. wt. % of hydrophile, 10%), Pluronic® R 17R1 (ave. MW: 1900; approx. MW of hydrophobe, 1700; approx. wt. % of hydrophile, 10%), Pluronic® R 31 R2 (ave. MW: 3300; approx. MW of hydrophobe, 3100; approx. wt. % of hydrophile, 20%), Pluronic® R 25R2 (ave. MW: 3100; approx. MW of hydrophobe, 2500; approx. wt. % of hydrophile, 20%), Pluronic® R 17R2 (ave. MW: 2150; approx. MW of hydrophobe, 1700; approx. wt. % of hydrophile, 20%), Pluromе® R 12R3 (ave. MW: 1800; approx. MW of hydrophobe, 1200; approx. wt. % of hydrophile, 30%), Pluronic® R 31R4 (ave. MW: 4150; approx. MW of hydrophobe, 3100; approx. wt. % of hydrophile, 40%), Pluronic® R 25R4 (ave. MW: 3600; approx. MW of hydrophobe, 2500; approx. wt. % of hydrophile, 40%), Pluronic® R 22R4 (ave. MW: 3350; approx. MW of hydrophobe, 2200; approx. wt. % of hydrophile, 40%), Pluronic® R 17R4 (ave. MW: 3650; approx. MW of hydrophobe, 1700; approx. wt. % of hydrophile, 40%), Pluronic® R 25R5 (ave. MW: 4320; approx. MW of hydrophobe, 2500; approx. wt. % of hydrophile, 50%), Pluronic® R 10R5 (ave. MW: 1950; approx. MW of hydrophobe, 1000; approx. wt. % of hydrophile, 50%), Pluronic® R 25R8 (ave. MW: 8550; approx. MW of hydrophobe, 2500; approx. wt. % of hydrophile, 80%), Pluronic® R 17R8 (ave. MW: 7000;

approx. MW of hydrophobe, 1700; approx. wt. % of hydrophile, 80%), and Pluronic® R 10R8 (ave. MW: 4550; approx. MW of hydrophobe, 1000; approx. wt. % of hydrophile, 80%).

Other commercially available poloxamers include compounds that are block copolymer of polyethylene and polypropylene glycol such as Synperonic® L121, Synperonic® L122, Synperonic® P104, Synperonic® P105, Synperonic® P123, Synperonic® P85 and Synperonic® P94; and compounds that are nonylphenyl polyethylene glycol such as Synperonic® NP10, Synperonic® NP30 and Synperonic® NP5.

Other poloxamers of the present invention include a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—$R^0$, wherein $R^0$ is a straight chain aliphatic group of 2 to 6 carbon atoms, which may be substituted, wherein said polyether segments comprise at least one of an A-type of B-type segment. See U.S. Pat. No. 5,656,611, by Kabonov, et al., which is incorporated herein by reference in its entirety.

Other auxiliary agents of the present invention include, but are not limited to Acacia (gum arabic); the poloxyethylene ether R—O—$(C_2H_4O)_x$—H (BRIJ®), e.g, polyethylene glycol dodecyl ether (BRIJ® 35, x=23), polyethylene glycol dodecyl ether (BRIJ® 30, x=4), polyethylene glycol hexadecyl ether (BRIJ® 52 x=2), polyethylene glycol hexadecyl ether (BRIJ® 56, x=10), polyethylene glycol hexadecyl ether (BRIJ® 58P, x=20), polyethylene glycol octadecyl ether (BRIJ® 72, x=2), polyethylene glycol octadecyl ether (BRIJ® 76, x=10), polyethylene glycol octadecyl ether (BRIJ® 78P, x=20), polyethylene glycol oleyl ether (BRIJ® 92V, x=2), and polyoxyl 10 oleyl ether (BRIJ® 97, x=10); poly-D-glucosamine (chitosan); chlorobutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40®); octylphenoxypolyethoxyethanol (NONIDET NP-40 from Amresco); ethyl phenol poly (ethylene glycol ether)$^n$, n=11 (Nonidet® P40 from Roche); octyl phenol ethylene oxide condensate with about 9 ethylene oxide units (nonidet P40); IGEPAL CA 630® ((octyl phenoxy) polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20®; polyoxyethylene sorbitan monooleate (polysorbate 80, or TWEEN-80®); propylene glycol diacetate; propylene glycol monstearate; protamine sulfate; proteolytic enzymes; sodium dodecyl sulfate (SDS); sodium monolaurate; sodium stearate; sorbitan derivatives (SPAN®), e.g., sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85); 2,6,10,15, 19,23-hexamethyl-2,6,10,14,18,22-tetracosahexaene (squalene); stachyose; stearic acid; sucrose; surfactin (lipopeptide antibiotic from *Bacillus subtilis*); dodecylpoly (ethyleneglycolether)$_9$ (Thesit®) MW 582.9; octyl phenol ethylene oxide condensate with about 9–10 ethylene oxide units (Triton X-100™); octyl phenol ethylene oxide condensate with about 7–8 ethylene oxide units (Triton X-114™); tris(2-hydroxyethyl)amine (trolamine); and emulsifying wax.

Preferred auxiliary agents include non-ionic detergents and surfactants such as Pluronic® F68, Pluronic® F77, Pluronic® F108, Pluronic® F127, Pluronic® P65, Pluronic® P85, Pluronic® P103, Pluronic® P104, Pluronic® P105, Pluronic® P123, Pluronic® L31, Pluronic® L43, Pluronic® L44, Pluronic® L61, Pluronic® L62, Pluronic® L64, Pluronic® L81, Pluronic® L92, Pluronic® L101, Pluronic® L121, Pluronic®g R17R4, Pluronic® R 25R4, Pluronic® R 25R2, IGEPAL CA 630®), NONIDET NP-40, Nonidet® P40, Tween-20®, Tween-80®, Triton X-100®, Triton X-114®, Thesit®; the anionic detergent sodium dodecyl sulfate (SDS); the sugar stachyose; the condensing agent DMSO; and the chelator/DNAse inhibitor EDTA. Even more preferred are the auxiliary agents Nonidet® P40, Triton X-100®, Pluronic® F68, Pluronic® F77, Pluronic® F108, Pluronic® P65, Pluronic® P103, Pluronic® L31, Pluronic® L44, Pluronic® L61, Pluronic® L64, Pluronic® L92, Pluronic® R 17R4, Pluronic® R 25R4 and Pluronic® R 25R2. Most preferred auxiliary agent is Pluronic® R 25R2.

In certain embodiments, compositions of the present invention comprise a combination of two or more auxiliary agents. Preferred combinations of auxiliary agents include, but are not limited to: Pluronic® P65+F68, Pluronic® P65+P103, Pluronic® F68+F108, and Pluronic® F68+P103, Pluronic® R 25R2+Pluronic® F68, Pluronic® R 25R2+ F65, Pluronic® R 25R2+L31, and Pluronic® 25R2+Triton-X-100®.

That certain of the auxiliary agents disclosed herein were effective in increasing expression of polypeptides encoded by polynucleotides delivered to vertebrate cells in vivo was unexpected in view of results showing that other, similar compounds have no effect on expression of polypeptides encoded by polynucleotides delivered to vertebrate cells in vivo, or even hinder such expression. For example, the following compounds had no ability to enhance, relative to a composition which is identical except for the inclusion of the compounds, the entry of polynucleotides into vertebrate cells in vivo, and/or the in vivo expression of polypeptides encoded by such polynucleotides: actin, benzyl alcohol, 3[(3-Cholamidopropyl)dimethylammonio]-1-propanesulfonate (CHAPS®), deoxycholic acid, EGTA, lechitin, PEG-40 Stearate (MYRJ 52®) Macrogol-50 stearate (MYRJ 53®), n-dodecylmaltoside, block copolymers of poly(ethyleneoxide)-poly(propyleneoxide)-poly (ethyleneoxide) (ave. MW 12,600 Pluronic® F127), polysorbate 40 (Tween-40®), saponin, sorbitan monolaurate (SPAN® 20), n-octylglucoside, Triton X-N60, polyoxyethylene 10 cetyl ether, polyoxyethylene 20 stearyl ether, heptanoyl-N-methyl-glucamide (MEGA-7), octanyol-N-methyl-glucamide (MEGA-8), nonanoyl-N-methylglucamide (MEGA-9); and n-hexadecyl-N,N-dimethyl-3-ammonio-1-propanesulfonate (Zwittergent®). Accordingly, these compounds are not considered to be auxiliary agents of the present invention.

Preferably, compositions of the present invention comprise an auxiliary agent mixed in an aqueous solution. Suitable aqueous solutions include, but are not limited to, distilled water, normal saline, PBS, as well as the various aqueous salt solutions disclosed herein, e.g.: an aqueous solution with a salt M-X dissolved therein at a molar concentration from about 20 mM to about 300 mM, and reaction, association, or dissociation products thereof, where M is an alkali metal (e.g., Li+, Na+, K+, Rb+), preferably of sodium and potassium, and where X is an anion selected from the group consisting of phosphate, acetate, bicarbonate, sulfate, pyruvate, and an organic monophosphate ester, preferably glucose 6-phosphate or DL-α-glycerol phosphate; and an aqueous solution/cationic lipid suspension with a salt M-X dissolved therein at a molar concentration from about 0.1 mM to about 150 mM, and reaction, association, or dissociation products thereof, where M is an alkali metal (e.g., Li+, Na+, K+, Rb+), preferably sodium and potassium, and where X is an anion selected from the group consisting of phosphate, acetate, bicarbonate, sulfate, pyruvate, and an organic monophosphate ester, preferably glucose 6-phosphate or DL-α-glycerol phosphate. Preferred aqueous solutions in which to dissolve, suspend or emulsify an auxiliary agent of the present invention include aqueous solutions comprising about 100 mM to about 200 mM sodium phosphate, more preferably 150 mM sodium phosphate; about 100 mM to about 200 mM potassium phosphate, more preferably about 150 mM potassium phosphate; about 1 mM to about 3 mM sodium phosphate plus a cationic lipid, more preferably about 2.5 mM sodium phosphate plus a cationic lipid; or about 1 mM to about 3 mM potassium phosphate plus a cationic lipid, more preferably about 2.5 mM potassium phosphate plus a cationic lipid.

Methods to determine the optimal concentration of an auxiliary agent for any given composition are disclosed herein. Some examples of preferred auxiliary agent amounts are as follows. About 0.0001% (v/v) to about 0.5% (v/v) Tween-80®, preferably about 0.001% (v/v) to about 0.2% (v/v) of Tween-80®, more preferably about 0.01% (v/v) to about 0.1% (v/v) of Tween-80®, with about 0.1% (v/v) Tween-80® being the most preferred; about 0.001% (v/v) to about 0.5% (v/v) of Tween-20®, preferably about 0.01% (v/v) to about 0.2% (v/v) of Tween-20®, more preferably about 0.05% (v/v) to about 0.1% (v/v) of Tween-20®, with about 0.1% (v/v) Tween-20® being the most preferred; about 0.001% (v/v) to about 2% (v/v) of Triton X-100™, preferably about 0.003% (v/v) to about 1% (v/v) of Triton X-100™, more preferably about 0.006% (v/v) to about 0.1% (v/v) of Triton X-100™, even more preferably about 0.01% (v/v) to about 0.03% (v/v) of Triton X-100™, with about 0.01% (v/v) Triton X-100™ being the most preferred; about 0.001% (v/v) to about 1% (v/v) of Triton X-114™, preferably about 0.005% (v/v) to about 0.1% (v/v) of Triton X-114™, more preferably about 0.005% (v/v) to about 0.01% (v/v) of Triton X-114™, with about 0.01% Triton X-114™ being the most preferred; about 0.001% (v/v) to about 1% (v/v) of NONIDET NP-40®, preferably about 0.01% (v/v) to about 0.1% (v/v) of NONIDET NP-40®, more preferably about 0.01% (v/v) to about 0.05% (v/v) of NONIDET N-P 40®, with about 0.01% NONIDET NP-40® being the most preferred; about 0.001% (w/v) to about 10.0% (w/v) of Pluronic® F68, preferably about 0.001% (w/v) to about 8.0% (w/v) of Pluronic F68, preferably about 0.01% (w/v) to about 8.0% (w/v) of Pluronic® F68, more preferably about 0.1% (w/v) to about 6.0% (w/v) of Pluronic® F68, even more preferably about 0.5% (w/v) to about 4.0% (w/v) of Pluronic® F68, with about 1.0% (w/v) to about 4.0% (w/v) Pluronic® F68 being the most preferred; about 0.001% (w/v) to about 4.0% (w/v) of Pluronic® P65, preferably about 0.001% (w/v) to about 2.0% (w/v) of Pluronic® P65, preferably about 0.01% (w/v) to about 1% (w/v) Pluronic® P65, more preferably about 0.1% (w/v) to about 1% (w/v) of Pluronic® P65, with 0.5% (w/v) of Pluronic® P65 being the most preferred; about 0.001% (w/v) to about 8.0% (w/v) of Pluronic® F77, preferably about 0.001% (w/v) to about 2.0% (w/v) of Pluronic® F77, preferably about 0.1% (w/v) to about 1.7% (w/v) of Pluronic® F77, with about 1.0% (w/v) Pluronic® F77 being the most preferred; about 0.001% (w/v) to about 2.0% (w/v) of Pluronic® L64, preferably about 0.001% (w/v) to about 1.0% (w/v) of Pluronic® L64, preferably about 0.01% (w/v) to about 1.0% (w/v) of Pluronic® L64, preferably about 0.01% (w/v) to about 0.5% (w/v) of Pluronic® L64, with about 0.01% (w/v) to about 0.1% (w/v) of Pluronic® L64 being the most preferred; about 0.001% (v/v) to about 0.05% (v/v) of Nonidet P40, preferably about 0.005% (v/v) to about 0.01% (v/v) of Nonidet P40, with about 0.01% Nonidet P40 being the most preferred; about 0.0001% (w/v) to about 0.1% (w/v) of SDS, preferably about 0.001% (w/v) to about 0.01% (w/v) of SDS, with about 0.001% (w/v) of SDS being the most preferred; about 0.0001% (v/v) to about 1% (v/v) of DMSO, preferably about 0.001% (v/v) to about 0.1% (v/v) of DMSO, with about 0.001% (v/v) of DMSO being the most preferred; about 0.0001% (v/v) to about 0.1% (v/v) of IGEPAL CA 630®, preferably about 0.0001% (v/v) to about 0.05% (v/v) of IGEPAL CA 630®, with about 0.0005% (v/v) of IGEPAL CA 630® being the most preferred; about 10 mM to about 600 mM of stachyose, preferably about 50 mM to about 300 mM of stachyose, more preferably about 100 mM to about 200 mM of stachyose, with about 100 mM stachyose being the most preferred; and about 0.001 mM to about 5.0 mM of EDTA, preferably about 0.005 mM to about 0.5 mM of EDTA, more preferably about 0.01 mM to about 0.1 mM EDTA, with about 0.01 mM EDTA being the most preferred.

Additional preferred auxiliary agent amounts include about 0.01% (w/v) to about 1.0% (w/v) of Pluronic® F108, preferably about 0.05% (w/v) to about 0.5% (w/v) of Pluronic® F108, with about 0.1% (w/v) of Pluronic® F108 being the most preferred; about 0.1% (w/v) to about 3.0% (w/v) of Pluronic® F127, preferably about 0.5% (w/v) to about 2.0% (w/v) of Pluronic® F127, with 0.5% (w/v) of Pluronic® F127 being the most preferred; about 0.005% (w/v) to about 2.0% (w/v) of Pluronic® F103, preferably about 0.01% (w/v) to about 1.0% (w/v) of Pluronic® F103, more preferably about 0.05% (w/v) to about 0.10% (w/v) of Pluronic® F103, with about 0.05% (w/v) of Pluronic® F103 being the most preferred; about 0.005% (w/v) to about 2.0% (w/v) of Pluronic® P104, preferably about 0.01% (w/v) to about 1.0% (w/v) of Pluronic® P104, with about 0.10% (w/v) of Pluronic® P104 being the most preferred; about 0.005% (w/v) to about 2.0% (w/v) of Pluronic® P105, preferably about 0.005% (w/v) to about 1.0% (w/v) of Pluronic® P105, more preferably about 0.01% (w/v) to about 0.10% (w/v) of Pluronic® P105, with about 0.01% (w/v) of Pluronic® P105 being the most preferred; about 0.0001% (w/v) to about 2.0% (w/v) of Pluronic® L44, preferably about 0.0005% (w/v) to about 1.0% (w/v) of Pluronic® L44, more preferably about 0.001% (w/v) to about 0.01% (w/v) or 0.10% (w/v) of Pluronic® L44, with about 0.001% (w/v) of Pluronic® L44 being the most preferred; about 0.0005% (w/v) to about 2.0% (w/v) of Pluronic® L62, preferably about 0.001% (w/v) to about 1.0% (w/v) of Pluronic® L62, more preferably about 0.001% (w/v) to about 0.10% (w/v) of Pluronic® L62, even more preferably about 0.001% (w/v) to about 0.01% (w/v) of Pluronic® L62, with about 0.01% (w/v) of Pluronic® L62 being the most preferred; about 0.001% (w/v) to about 2.0% (w/v) of Pluronic® R 17R4, preferably about 0.002% (w/v) to about 1.0% (w/v) of Pluronic® R 17R4, more preferably about 0.01% (w/v) to about 0.10% (w/v) of Pluronic® R 17R4, with about 0.10% (w/v) of Pluronic® R 17R4 being the most preferred; about 0.001% (w/v) to about 2.0% (w/v) of Pluronic® R 25R4, preferably about 0.002% (w/v) to about 1.0% (w/v) of Pluronic® R 25R4, more preferably about 0.01% (w/v) to about 0.10% (w/v) of Pluronic® R 25R4, with about 0.01% (w/v) of Pluronic® R 25R4 being the most preferred; about 0.001% (w/v) to about 2.0% (w/v) of Pluronic® R 25R4, preferably about 0.001% (w/v) to about 1.0% (w/v) of Pluronic® R 25R2, more preferably about 0.001% (w/v) to about 0.1% (w/v) of Pluronic® R 25R42, with about 0.01% (w/v) of Pluronic® R25R2 being the most preferred; and about 0.001% (w/v) to about 1.0% (w/v) of Thesit®, preferably about 0.005% (w/v) to about 0.10% (w/v) of Thesit®, more preferably about 0.005% (w/v) to about 0.05% (w/v) or 0.01% (w/v) of Thesit® with about 0.005% (w/v) of Thesit® being the most preferred.

Preferred auxiliary agent amounts in combination include, but are not limited to about 0.10% (w/v) of Pluronic® P65 combined with about 4.0% (w/v) of Pluronic® F68; about 0.10% (w/v) of Pluronic® P65 combined with about 0.05% (w/v) of Pluronic® P103; about 4.0% (w/v) of Pluronic® F68 combined with about 0.10% (w/v) of Pluronic® F108; and about 4.0% (w/v) of Pluronic® F68 combined with about 0.05% (w/v) of Pluronic® F103, about 4.0% (w/v) of Pluronic® F68 combined with about 0.01% (w/v) of Pluronic® R25R2, about 0.01% Pluronic® R 25R2 combined with about 0.1% P65, about 0.01% Pluronic® R 25R2 combined with about 0.05% Pluronic® L31 and about 0.01% Pluronic® R 25R2 combined with 0.1% Triton-X-100.

Polynucleotides

The present invention covers the delivery to a vertebrate of a polypeptide-encoding polynucleotide in a detectable amount. By "detectable" is meant the polynucleotide, or a polypeptide product thereof, can be identified following delivery to a vertebrate. Methods of detection include, but are not limited to tissue immunohistochemistry, in situ hybridization, various assays for detecting enzymatic activities or ligand/receptor binding, northern assays, and PCR. Methods of detection can also include methods of measuring biological response (e.g., hematocrit level, tumor rejection, survival after challenge with a pathogen, and alleviation of disease symptoms) without directly quantitating the expression level. Preferably, the encoded polypeptide is expressed in vivo in the vertebrate in an amount sufficient to provide an immunogenic, immunomodulatory, therapeutic, or corrective effect to a vertebrate in need of such treatment.

The term "nucleic acid" is intended to encompass a singular "nucleic acid" as well as plural "nucleic acids," and refers to an isolated molecule or construct, e.g., virus genomes (preferably non-infectious), messenger RNA (mRNA), plasmid DNA (pDNA), or derivatives of pDNA (e.g., minicircles as described in (Darquet, A-M et al., *Gene Therapy* 4:1341–1349 (1997)) comprising a polynucleotide. A nucleic acid may be provided in linear (e.g., mRNA), circular (e.g., plasmid), or branched form as well as double-stranded or single-stranded forms. A nucleic acid may comprise a conventional phosphodiester bond or a non-conventional bond (e.g., an amide bond, such as found in peptide nucleic acids (PNA)).

The term "polynucleotide" refers to any one or more nucleic acid segments, e.g., DNA or RNA fragments, present in a nucleic acid or construct. Two or more polynucleotides of the present invention can be present in a single nucleic acid construct, e.g., on a single plasmid, or in separate nucleic acid constructs, e.g., on separate plasmids. Furthermore, any polynucleotide may encode a single polypeptide, e.g., a single antigen, cytokine, or regulatory polypeptide, or may encode more than one polypeptide, e.g., a polynucleotide may encode two or more polypeptides. In addition, a polynucleotide may encode a regulatory element such as a promoter or a transcription terminator, or may encode a specific element of a polypeptide or protein, such as a secretory signal peptide or a functional domain.

Nucleic acids and/or polynucleotides of the present invention, e.g., plasmid DNA, derivatives of plasmid DNA, mRNA, linear DNA, viral genomes, or polynucleotide fragments contained therein may be formulated into any of the various compositions and may be used in any of the methods disclosed herein. For aqueous compositions used in vivo, use of sterile pyrogen-free water is preferred. Such formulations will contain an effective amount of a polynucleotide together with a suitable salt and/or auxiliary agent as disclosed herein, in order to prepare pharmaceutically acceptable compositions suitable for optimal administration to a vertebrate. Insoluble polynucleotides may be solubilized in a weak acid or weak base, and then diluted to the desired volume, for example, with an aqueous solution of the present invention. The pH of the solution may be adjusted as appropriate. In addition, a pharmaceutically acceptable additive can be used to provide an appropriate osmolarity. Such additives are within the purview of one skilled in the art.

The amount of a polynucleotide included in a composition of the present invention depends on many factors, including the age and weight of the subject, the delivery method and route, the type of treatment desired, and the type of polynucleotide being administered. In general, a composition of the present invention includes from about 1 ng to about 30 mg of a polynucleotide, more preferably, from about 100 ng to about 10 mg of a polynucleotide.

Certain preferred compositions of the present invention may include about 1 ng of a polynucleotide, about 5 ng of a polynucleotide, about 10 ng of a polynucleotide, about 50 ng of a polynucleotide, about 100 ng of a polynucleotide, about 500 ng of a polynucleotide, about 1 $\mu$g of a polynucleotide, about 5 $\mu$g of a polynucleotide, about 10 $\mu$g of a polynucleotide, about 50 $\mu$g of a polynucleotide, about 100 $\mu$g of a polynucleotide, about 150 $\mu$g of a polynucleotide, about 200 $\mu$g of a polynucleotide, about 250 $\mu$g of a polynucleotide, about 300 $\mu$g of a polynucleotide, about 350 $\mu$g of a polynucleotide, about 400 $\mu$g of a polynucleotide, about 450 $\mu$g of a polynucleotide, about 500 $\mu$g of a polynucleotide, about 550 $\mu$g of a polynucleotide, about 600 $\mu$g of a polynucleotide, about 650 $\mu$g of a polynucleotide, about 700 $\mu$g of a polynucleotide, about 750 $\mu$g of a polynucleotide, about 800 $\mu$g of a polynucleotide, about 850 $\mu$g of a polynucleotide, about 900 $\mu$g of a polynucleotide, about 950 $\mu$g of a polynucleotide, about 1 mg of a polynucleotide, about 5 mg of a polynucleotide, about 10 mg of a polynucleotide, about 15 mg of a polynucleotide, about 20 mg of a polynucleotide, about 25 mg of a polynucleotide, and about 30 mg of a polynucleotide.

The choice of polynucleotide form depends in part on the desired kinetics and duration of expression. When long-term expression of the polypeptide encoded by the polynucleotide is desired, the preferred form is DNA, preferably plasmid DNA. Alternatively, when short-term expression of the polypeptide encoded by the polynucleotide is desired, the preferred form is RNA, preferably messenger RNA, since RNA is rapidly translated into polypeptide, but is degraded more quickly than DNA.

In one embodiment, a polynucleotide of the present invention is RNA. Preferably in this embodiment, the RNA is in the form of messenger RNA (mRNA). Methods for introducing RNA sequences into vertebrate cells is described in U.S. Pat. No. 5,580,859, the disclosure of which is incorporated herein by reference in its entirety.

Alternatively, the RNA is in the form of an RNA virus genome. Preferably an RNA virus genome of the present invention is noninfectious, (i.e., does not result in the production of infectious virus particles in vertebrate cells). Suitable RNA virus genomes include, but are not limited to, alphavirus genomes, picornavirus genomes, and retrovirus genomes. Methods for the in vivo introduction of non-infectious viral genomes to vertebrate tissues are well known to those of ordinary skill in the art and are described, e.g, in Altman-Hamamdzic, S., et al., *Gene Therapy* 4, 815–822 (1997), in U.S. Pat. No. 4,980,289, Dec. 25, 1990, and in Miller, A. D., et al., *Meth. Enzymol.* 217:581–599 (1993), the disclosures of which are incorporated herein by reference in their entireties. Viral replicons, i.e., non-infectious RNA virus genomes packaged in a viral coat, e.g., a picornavirus coat or an alphavirus coat, are also useful for efficient administration of RNA. See, e.g., U.S. Pat. Nos. 5,766,602, 5,614,413, and PCT Publication No. WO 95/07994, the disclosures of which are incorporated herein by reference in their entireties.

Preferably, the polynucleotide is DNA. In the case of DNA, a polynucleotide encoding a polypeptide is normally operably associated with a promoter. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

An operable association is when a polynucleotide encoding a gene product, e.g., a polypeptide, is associated with one or more regulatory sequences in such a way as to place expression of the molecule under the influence or control of the regulatory sequence(s). Two DNA fragments (such as a polypeptide-coding polynucleotide and a promoter associated with the 5' end of the polynucleotide) are "operably associated" if induction of promoter function results in the transcription of mRNA encoding the desired gene product and if the nature of the linkage between the two DNA fragments does not (1) result in the introduction of a frame-shift mutation, (2) interfere with the ability of the expression regulatory sequences to direct the expression of the gene product, or (3) interfere with the ability of the DNA template to be transcribed. Thus, a promoter region would be operably associated with a polynucleotide encoding a polypeptide if the promoter was capable of effecting transcription of that polynucleotide.

A variety of transcription control regions are known to those skilled in the art. Preferred transcription control regions include those which function in vertebrate cells, such as, but not limited to, promoter and enhancer segments from cytomegaloviruses (preferably the immediate early promoter, preferably in conjunction with intron-A), simian virus 40 (preferably the early promoter), retroviruses (such as Rous sarcoma virus), and picornaviruses (particularly an internal ribosome entry site, or IRES, also referred to as a CITE sequence). Other preferred transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Preferably, a DNA polynucleotide of the present invention is part of a circular or linearized plasmid which is preferably non-infectious (i.e., does not result in the production of infectious virus particles in vertebrate cells), and nonintegrating (i.e., does not integrate into the genome of vertebrate cells). A linearized plasmid is a plasmid that was previously circular but has been linearized, for example, by digestion with a restriction endonuclease.

Alternatively, DNA virus genomes may be used to administer DNA polynucleotides into vertebrate cells. Preferably a DNA virus genome of the present invention is noninfectious, (i.e., does not result in the production of infectious virus particles in vertebrate cells), and nonintegrating (i.e., does not integrate into the genome of vertebrate cells). Suitable DNA virus genomes include herpesvirus genomes, adenovirus genomes, adeno-associated virus genomes, and poxvirus genomes. References citing methods for the in vivo introduction of non-infectious virus genomes to vertebrate tissues are well known to those of ordinary skill in the art, and are cited supra.

Polynucleotides of the present invention may be associated with additional polynucleotides which encode secretory or signal peptides, which direct the secretion of the polypeptide encoded by the polynucleotide of the present invention. Those of ordinary skill in the art are aware that polypeptides secreted by vertebrate cells normally have a signal peptide which is cleaved from the complete polypeptide to produce a secreted "mature" form of the polypeptide.

Polypeptides

Compositions of the present invention may be used to deliver a wide variety of polypeptides to a vertebrate in need of any given polypeptide. Suitable polypeptides include, but are not limited to: therapeutic polypeptides, antigenic polypeptides, immunogenic polypeptides, immunomodulatory polypeptides, functional self polypeptides, and other functional polypeptides.

As used herein, a "therapeutic polypeptide" is a polypeptide which when delivered to a vertebrate, treats, i.e., cures, ameliorates, or lessens the symptoms of, a given disease in that vertebrate, or alternatively, prolongs the life of the vertebrate by slowing the progress of a terminal disease. As used herein, an "immunomodulatory polypeptide" is a polypeptide which, when delivered to a vertebrate, can alter, enhance, suppress, or regulate an immune response in a vertebrate. Immunomodulatory polypeptides are a subset of therapeutic polypeptides. Therapeutic and immunomodulatory polypeptides of the present invention include, but are not limited to, cytokines, chemokines, lymphokines, ligands, receptors, hormones, apoptosis-inducing polypeptides, enzymes, antibodies, and growth factors. Examples include, but are not limited to granulocyte macrophage colony stimulating factor (GM-CSF), granulocyte colony stimulating factor (G-CSF), macrophage colony stimulating factor (M-CSF), colony stimulating factor (CSF), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNω), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), Leishmania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), erythropoietin (EPO), and insulin.

Therapeutic polypeptides of the present invention may be used to treat diseases such as Parkinson's disease, cancer, and heart disease. In addition, therapeutic polypeptides may be used to treat autoimmune disorders such as multiple sclerosis; Sjogren's syndrome; sarcoidosis; insulin dependent diabetes mellitus; autoimmune thyroiditis; arthritis (e.g.), osteoarthritis, rheumatoid arthritis, reactive arthritis, and psoriatic arthritis; ankylosing spondylitis; and scleroderma. Also, therapeutic polypeptides of the present invention can be used to treat acute and chronic inflammatory disorders, to promote wound healing, and to prevent rejection after transplantation of cells, tissues, or organs.

Therapeutic polypeptides of the present invention, for example, neurotrophic factors (NTFs), may be used to promote the survival, maintenance, differentiation, repair, regeneration, and growth of cells in the brain, spinal cord, and peripheral nerves. Suitable NTFs include, but are not limited to, NGF, BDNF, the Neurotrophins or NTs such as NT-2, NT-3, NT-4, NT-5, GDNF, CNTF, as well as others. The administration of purified recombinant NTFs represents a clinical strategy for treatment of such acute and chronic nervous system disorders. Such disorders include, but are not limited to mechanical or chemical brain or spinal cord injury, Parkinson's Disease, Alzheimer's Disease and other dementias, Amyotrophic Lateral Sclerosis and Multiple Sclerosis.

Therapeutic polypeptides of the present invention, for example, growth factors, may be used to promote wound healing. Useful growth factors include, but are not limited to FGF, and EGF.

Therapeutic polypeptides of the present invention may be used to promote cell suicide (termed "apoptosis"). Suitable apoptotic polypeptides include the BAX protein. Alternatively, therapeutic polypeptides of the present invention may be used to prevent apoptosis. Suitable apoptosis antagonists include the BAX antagonist Bcl-2. A disease which may be treated with apoptosis-inhibiting polypeptides is Muscular Dystrophy (MD), where patients have a defective protein called Dystrophin. Dystrophin is required for proper muscle function. The non-defective, normal Dystrophin may act as an antigen if delivered via plasmid DNA to patients with MD. In this case, muscle cells transduced with DNA encoding normal Dystrophin would be recognized by the immune system and killed by Dystrophin-specific T cell based responses. Such T cell based killing is known to kill cells by inducing apoptosis. If the normal, and potentially immunogenic, Dystrophin could be delivered into muscle cells along with Bcl-2 or other apoptosis-preventing protein, one would expect that CTL would be unable to kill the muscle cells. This reasoning applies to many genetic diseases where treatment involves delivery of a "normal", and therefore potentially immunogenic, copy of a protein.

As used herein, a "functional self polypeptide" is a polypeptide which is required for normal functioning of a vertebrate, but because of, e.g., genetic disease, cancer, environmental damage, or other cause, is missing, defective, or non-functional in a given individual. A composition of the present invention is used to restore the individual to a normal state by supplying the necessary polypeptide. Examples of functional self polypeptides include insulin, dystrophin, cystic fibrosis transmembrane conductance regulator, granulocyte macrophage colony stimulating factor, granulocyte colony stimulating factor, macrophage colony stimulating factor colony stimulating factor, interleukin 2, interleukin-3, interleukin 4, interleukin 5, interleukin 6, interleukin 7, interleukin 8, interleukin 10, interleukin 12, interleukin 15, interleukin 18, interferon alpha, interferon beta, interferon gamma, interferon omega, interferon tau, interferon gamma inducing factor I, transforming growth factor beta, RANTES, Flt-3 ligand, macrophage inflammatory proteins, platelet derived growth factor, tumor necrosis factor, epidermal growth factor, vascular epithelial growth factor, fibroblast growth factor, insulin-like growth factors I and II, insulin-like growth factor binding proteins, nerve growth factor, brain derived neurotrophic factor, neurotrophin-2, neurotrophin-3, neurotrophin-4, neurotrophin-5, glial cell line-derived neurotrophic factor, ciliary neurotrophic factor, and erythropoietin. Examples of diseases or disorders that may be treated with functional self polypeptides include, but are not limited to: diabetes, muscular dystrophy, multiple sclerosis, Parkinson's disease, Alzheimer's disease, arthritis, sickle cell anemia, and hemophilia.

As used herein, an antigenic polypeptide or an immunogenic polypeptide is a polypeptide which, when introduced into a vertebrate, reacts with the immune system molecules of the vertebrate, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides include, but are not limited to, polypeptides from infectious agents such as bacteria, viruses, parasites, or fungi, allergens such as those from pet dander, plants, dust, and other environmental sources, as well as certain self polypeptides, for example, tumor-associated antigens.

Antigenic and immunogenic polypeptides of the present invention can be used to prevent or treat, i.e., cure, ameliorate, lessen the severity of, or prevent or reduce contagion of viral, bacterial, fungal, and parasitic infectious diseases, as well as to treat allergies.

In addition, antigenic and immunogenic polypeptides of the present invention can be used to prevent or treat, i.e., cure, ameliorate, or lessen the severity of cancer including, but not limited to, cancers of oral cavity and pharynx (i.e., tongue, mouth, pharynx), digestive system (i.e., esophagus, stomach, small intestine, colon, rectum, anus, anal canal, anorectum, liver, gallbladder, pancreas), respiratory system (i.e., larynx, lung), bones, joints, soft tissues (including heart), skin, melanoma, breast, reproductive organs (i.e., cervix, endometirum, ovary, vulva, vagina, prostate, testis, penis), urinary system (i.e., urinary bladder, kidney, ureter, and other urinary organs), eye, brain, endocrine system (i.e., thyroid and other endocrine), lymphoma (i.e., hodgkin's disease, non-hodgkin's lymphoma), multiple myeloma, leukemia (i.e., acute lymphocytic leukemia, chronic lymphocytic leukemia, acute myeloid leukemia, chronic myeloid leukemia).

Examples of viral antigenic and immunogenic polypeptides include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigenic and immunogenic polypeptides include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of fungal immunogenic and antigenic polypeptides include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite immunogenic and antigenic polypeptides include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite immunogenic and antigenic polypeptides include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite immunogenic and antigenic polypeptides include, but are not limited to, polypeptides (including protective antigens as well as allergens) from fleas; ticks, including hard ticks and soft ticks; flies, such as midges, mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs.

Examples of tumor-associated antigenic and immunogenic polypeptides include, but are not limited to, tumor-specific immunoglobulin variable regions (e.g., B cell lymphoma idiotypes), GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), HER2/neu, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Also included as polypeptides of the present invention are fragments, derivatives, analogs, or variants of the foregoing polypeptides, and any combination of the foregoing polypeptides. Additional polypeptides may be found, for example in "Foundations in Microbiology," Talaro, et al., eds., McGraw-Hill Companies (October, 1998), Fields, et al., "Virology," 3d ed., Lippincott-Raven (1996), "Biochemistry and Molecular Biology of Parasites," Marr, et al., eds., Academic Press (1995), and Deacon, J., "Modern Mycology," Blackwell Science Inc (1997), which are incorporated herein by reference.

Transfection Facilitating Materials

Compositions of the present invention can also include one or more transfection facilitating materials that facilitate delivery of polynucleotides to the interior of a cell, and/or to a desired location within a cell. Examples of the transfection facilitating materials include, but are not limited to, lipids, preferably cationic lipids; inorganic materials such as calcium phosphate, and metal (e.g., gold or tungsten) particles (e.g., "powder" type delivery solutions); peptides, including cationic peptides, targeting peptides for selective delivery to certain cells or intracellular organelles such as the nucleus or nucleolus, and amphipathic peptides, i.e. helix forming or pore forming peptides; basic proteins, such as histones; asialoproteins; viral proteins (e.g., Sendai virus coat protein); pore-forming proteins; and polymers, including dendrimers, star-polymers, "homogenous" poly-amino acids (e.g., poly-lysine, poly-arginine), "heterogenous" poly-amino acids (e.g., mixtures of lysine & glycine), co-polymers, polyvinylpyrrolidinone (PVP), and polyethylene glycol (PEG). Furthermore, those auxiliary agents of the present invention which facilitate and enhance the entry of a polynucleotide into vertebrate cells in vivo, may also be considered "transfection facilitating materials."

Certain embodiments of the present invention may include lipids as a transfection facilitating material, including cationic lipids (e.g., DMRIE, DOSPA, DC-Chol, GAP-DLRIE), basic lipids (e.g., steryl amine), neutral lipids (e.g., cholesterol), anionic lipids (e.g., phosphatidyl serine), and zwitterionic lipids (e.g., DOPE, DOPC). However, certain compositions and methods of the present invention, e.g., those including or utilizing compositions comprising a salt M-X dissolved in an aqueous solution at a molar concentration from about 20 mM to about 300 mM, where M is either sodium or potassium, and where X is either phosphate, acetate, bicarbonate, sulfate, pyruvate, and an organic monophosphate ester, preferably glucose 6-phosphate or DL-α-glycerol phosphate, are preferably substantially free of cationic lipids.

Certain other compositions and methods of the present invention, e.g., those including or utilizing compositions comprising a salt M-X dissolved in aqeuous solution at a molar concentration from about 0.1 mM to about 150 mM, where M is either sodium and potassium, and where X is either phosphate, acetate, bicarbonate, sulfate, pyruvate, and an organic monophosphate ester, preferably glucose 6-phosphate or DL-α-glycerol phosphate, and where the aqueous solution is substantially free of chloride anion, always include cationic lipids as transfection facilitating agents. While not being bound by theory, cationic lipids are believed to bind effectively to negatively charged polynucleotides, thereby facilitating entry of the polynucleotide into cells. The use of cationic lipids is especially effective in the delivery of polynucleotides to non-muscle tissues, e.g., pulmonary tissues, tumor tissues, skin, peritoneum, tissues of digestive system, or vascular tissues.

Examples of cationic lipids are 5-carboxyspermylglycine dioctadecylamide (DOGS) and dipalmitoyl-phophatidylethanolamine-5-carboxyspermylamide (DPPES). Cationic cholesterol derivatives are also useful, including {3β-[N-N',N'-dimethylamino)ethane]-carbomoyl}-cholesterol (DC-Chol). Dimethyldioctdecyl-ammonium bromide (DDAB), N-(3-aminopropyl)-N,N-(bis-(2-tetradecyloxyethyl))-N-methyl-ammonium bromide (PADEMO), N-(3-aminopropyl)-N,N-(bis-(2-dodecyloxyethyl))-N-methyl-ammonium bromide (PADELO), N,N,N-tris-(2-dodecyloxy)ethyl-N-(3-amino) propyl-ammonium bromide (PATELO), and $N^1$-(3-aminopropyl)((2-dodecyloxy)ethyl)-$N^2$-(2-dodecyloxy) ethyl-1-piperazinaminium bromide (GALOE-BP) can also be employed in the present invention.

Non-diether cationic lipids, such as DL-1,2-dioleoyl-3-dimethylaminopropyl-β-hydroxyethylammonium (DORI diester), 1-O-oleyl-2-oleoyl-3-dimethylaminopropyl-β-hydroxyethylammonium (DORI ester/ether), and their salts promote in vivo gene delivery. Preferred cationic lipids comprise groups attached via a heteroatom attached to the quaternary ammonium moiety in the head group. A glycyl spacer can connect the linker to the hydroxyl group.

Preferred cationic lipids for use in certain embodiments of the present invention include DMRIE ((±)-N-(2-hydroxyethyl)-N,N-dimethyl-2,3-bis(tetradecyloxy)-1-propanaminium bromide), and GAP-DMORIE ((±)-N-(3-aminopropyl)-N,N-dimethyl-2,3-bis(syn-9-tetradeceneyloxy)-1-propanaminium bromide).

Also preferred are (±)-N,N-dimethyl-N-[2-(sperminecarboxamido)ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide (β-aminoethyl-DMRIE or βAE-DMRIE) (Wheeler, et al., *Biochim. Biophys. Acta* 1280:1–11 (1996)), and (±)-N-(3-aminopropyl)-N,N-dimethyl-2,3-bis (dodecyloxy)-1-propaniminium bromide (GAP-DLRIE) (Wheeler, et al., *Proc. Natl. Acad. Sci. USA* 93:11454–11459 (1996)), which have been developed from DMRIE.

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAP-DMRIE), (±)-N-((N"-methyl)-N'-ureyl) propyl-N,N-dimethyl-2,3-bis(tetradecyloxy)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1-propaniminium bromide (HP-DORIE).

A preferred cationic lipid of the present invention is a "cytofectin." As used herein, a "cytofectin" refers to a subset of cationic lipids which incorporate certain structural features including, but not limited to, a quaternary ammonium group and/or a hydrophobic region (usually with two or more alkyl chains), but which do not require amine protonation to develop a positive charge. Examples of cytofectins may be found, for example, in U.S. Pat. No. 5,861,397, which is incorporated herein by reference in its entirety.

Preferred cytofectins for use in the present invention, include DMRIE ((±)-N-(2-hydroxyethyl)-N,N-dimethyl-2, 3-bis(tetradecyloxy)-1-propanaminium bromide), GAP-DMORIE ((±)-N-(3-aminopropyl)-N,N-dimethyl-2,3-bis (syn-9-tetradeceneyloxy)-1-propanaminium bromide), and GAP-DLRIE ((±)-N-(3-aminopropyl)-N,N-dimethyl-2,3-(bis-dodecyloxy)-1-propanaminium bromide).

Preferably, the cationic lipid is mixed with one or more co-lipids. For purposes of definition, the term "co-lipid"

refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. A preferred class of co-lipids are the zwitterionic phospholipids, which include the phosphatidylethanolamines and the phosphatidylcholines. Most preferably, the co-lipids are phosphatidylethanolamines, such as, for example, DOPE, DMPE and DPyPE. DOPE and DPyPE are particularly preferred. For immunization, the most preferred co-lipid is DPyPE, which comprises two phytanoyl substituents incorporated into the diacylphosphatidylethanolamine skeleton.

The preferred cationic lipid:co-lipid molar ratio of the present invention is from about 9:1 to about 1:9. More preferably, the cationic lipid:co-lipid molar ratio is from about 4:1 to about 1:4 and, still more preferably, is from about 2:1 to about 1:2. A most preferred cationic lipid:co-lipid molar ratio is about 1:1.

In order to maximize homogeneity, the cationic lipid and co-lipid components of the present invention are preferably dissolved in a solvent such as chloroform, followed by evaporation of the cationic lipid/co-lipid solution under vacuum to dryness as a film on the inner surface of a glass vessel (e.g., a Rotovap round-bottomed flask). Upon suspension in an aqueous solvent, the amphipathic lipid component molecules self-assemble into homogenous lipid vesicles. These lipid vesicles may subsequently be processed to have a selected mean diameter of uniform size prior to complexing with, for example, plasmid DNA according to methods known to those skilled in the art. For example, the sonication of a lipid solution is described in Felgner, P. L., et al., *Proc. Natl. Acad. Sci. USA* 84:7413–7417 (1987) and in U.S. Pat. No. 5,264,618, the disclosures of which are incorporated herein by reference in their entireties.

In the embodiments including cationic lipids, the polynucleotide construct(s) are combined with lipids by mixing, for example, a plasmid DNA solution and a solution of cationic lipid:co-lipid liposomes. Preferably, the concentration of each of the constituent solutions is adjusted prior to mixing such that the desired final plasmid DNA/cationic lipid:co-lipid ratio and the desired plasmid DNA final concentration will be obtained upon mixing the two solutions. For example, if the desired final solution is to be 2.5 mM sodium phosphate, the various components of the composition, e.g., plasmid DNA, cationic lipid:co-lipid liposomes, and any other desired auxiliary agents, transfection facilitating materials, or additives are each prepared in 2.5 mM sodium phosphate and then simply mixed to afford the desired complex.

Alternatively, if the desired final solution is to be, e.g. 2.5 mM sodium phosphate, certain components of the composition, e.g., the auxiliary agent and/or cationic lipid:co-lipid liposomes, is prepared in a volume of water which is less than that of the final volume of the composition, and certain other components of the composition, e.g., the plasmid DNA, is prepared in a solution of sodium phosphate at a higher concentration than 2.5 mM, in a volume such that when the components in water are added to the components in the sodium phosphate solution, the final composition is in an aqueous solution of 2.5 mM sodium phosphate. For example, the plasmid DNA could be prepared in 5.0 mM sodium phosphate at one half the final volume, the auxiliary agent and/or cationic lipid:co-lipid liposome is prepared in water at one half the final volume, and then these two elements are mixed together to produce the final composition.

The cationic lipid:co-lipid liposomes are preferably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g. argon) followed by high vacuum treatment.

A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, V., et al., *Biochim. Biophys. Acta* 1380(3) :354–368 (1998)), mechanical mixing (e.g., free moving materials in liquid or solid phase such as "polylysine+ cationic lipids") (Gao, X., and Huang, L., *Biochemistry* 35:1027–1036 (1996); Trubetskoy, V. S., et al., *Biochem. Biophys. Acta* 1131:311–313 (1992)), and aggregation (e.g., co-precipitation, gel forming such as in cationic lipids+polylactide co-galactide, and polylysine+gelatin).

Other Additives

Other hydrophobic and amphiphilic additives, such as, for example, sterols, fatty acids, gangliosides, glycolipids, lipopeptides, liposaccharides, neobees, niosomes, prostaglandins and sphingolipids, may also be included in the compositions of the present invention. In such compositions, these additives may be included in an amount between about 0.1 mol % and about 99.9 mol % (relative to total lipid). Preferably, these additives comprise about 1–50 mol % and, most preferably, about 2–25 mol %. Preferred additives include lipopeptides, liposaccharides and steroids.

Methods and Administration

The present invention further provides methods for delivering a polypeptide into a vertebrate, which comprise administering to the vertebrate one or more of the compositions described herein; such that upon administration of the composition, the polypeptide is expressed in the vertebrate, in an amount sufficient to be detectable. Methods to detect polypeptides expressed in a vertebrate are well known to those of ordinary skill in the art and include, but are not limited to, serological methods to detect the polypeptide in serum, e.g., western blotting, staining tissue sections by immunohistochemical methods, measuring an immune response generated by the vertebrate against the polypeptide, and measuring the activity of the polypeptide. Certain of these methods are disclosed in the Examples, below.

The present invention further provides a method for delivering a therapeutic polypeptide into a vertebrate, comprising administering to a vertebrate in need of the therapeutic polypeptide one or more of the compositions described herein. In this method, the composition comprises a polynucleotide encoding a therapeutic polypeptide. Upon administration of the composition according to this method, the needed therapeutic polypeptide is expressed in the vertebrate in a therapeutically effective amount.

Similarly, the present invention provides a method of enhancing or modulating an immune response in a vertebrate in need of such an enhanced or modulated immune response, comprising administering to the vertebrate one or more of the compositions described herein. In this method, the composition contains a polynucleotide encoding an immunogenic and/or immunomodulatory polypeptide. Upon administration of the composition according to this method, the needed immunogenic and/or immunomodulatory polypeptide is expressed in the vertebrate, in a sufficient amount to induce and/or modify a desired immune response in the vertebrate to prevent disease, cure disease, reduce the severity of disease symptoms, or prolong the life of the vertebrate.

Also, the present invention provides a method of enhancing or modulating an immune response in a healthy vertebrate for large-scale antibody production, comprising administering to the vertebrate one or more of the compositions described herein. In this method, the composition contains a polynucleotide encoding an immunogenic and/or immunomodulatory polypeptide. Upon administration of the composition according to this method, the immunogenic and/or immunomodulatory polypeptide is expressed in the vertebrate, in a sufficient amount to produce a vigorous antibody response in the vertebrate. The antibodies thus produced are then recovered from the vertebrate by, for example, the collection of serum, milk, or saliva. Such antibodies may be useful for research or diagnostic purposes, or for additional therapies in vertebrates in need of such therapies. For example, passive antibody treatment using antibodies produced by this method may prevent disease, cure disease, reduce the severity of disease symptoms, or prolong the life of a vertebrate.

Moreover, the present invention further provides a method of delivering a physiologically or metabolically necessary polypeptide to a vertebrate incapable of making a sufficient amount of a functional form of the polypeptide, comprising administering to the vertebrate one or more of the compositions disclosed herein. According to this method, the composition contains a polynucleotide encoding a functional self polypeptide. Upon administration of the composition according to this method, the needed functional self polypeptide is expressed in the vertebrate, in a sufficient amount to supply the vertebrate's requirements for the polypeptide.

An important aspect of the present invention is that use of the claimed compositions in any of the above methods allows the skilled artisan to reduce the amount of polynucleotide included in the composition relative to methods utilizing existing compositions, e.g., those which formulate the polynucleotide in saline or water, and those which do not use auxiliary agents. Even though the amount of polynucleotide is reduced, sufficient protein expression occurs in the treated vertebrate. Such a reduction in polynucleotide will significantly reduce the cost of producing compositions of the present invention. Accordingly, one embodiment of the present invention is a method to reduce the amount of polynucleotide required to obtain a desired clinical response in a vertebrate, comprising administering to the vertebrate one or more of the compositions disclosed herein.

In any of the methods disclosed herein, it is preferred that the composition be delivered to a mammal. More preferably, the mammal is a human.

Administration of the compositions of the present invention according to any of the above methods can be accomplished according to any of various methods known in the art. For example, U.S. Pat. No. 5,676,954, incorporated herein by reference in its entirety, reports on the injection of genetic material, complexed with cationic lipid carriers, into mice. Also, U.S. Pat. Nos. 5,589,466, 5,693,622, 5,580,859, 5,703,055, and PCT international patent application PCT/US94/06069 (WO 94/29469), the disclosures of which are incorporated herein by reference in their entireties, provide methods for delivering compositions comprising naked DNA, or DNA cationic lipid complexes to vertebrates.

More specifically, the compositions of the present invention may be administered to any tissue of a vertebrate, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

Furthermore, the compositions of the present invention may be administered to any internal cavity of a vertebrate, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention is administered to the luman of a duct of a salivary gland or a liver, the desired polypeptide is encoded in each of the salivary gland and the liver such that the polypeptide is delivered into the blood stream of the vertebrate from each of the salivary gland and the liver. Preferred modes for administration to secretory organs of a gastrointestinal system using the salivery gland, liver and pancreas to release a desired polypeptide into the bloodstream is disclosed in U.S. Pat. Nos. 5,837,693 and 6,004,944, both of which are incorporated herein by reference in their entireties.

Preferably, the compositions are administered to muscle, either skeletal muscle or cardiac muscle, or lung tissue. Most preferably, those embodiments comprising a salt M-X dissolved in aqueous solution at a molar concentration from about 20 mM to about 300 mM are delivered to muscle, and those embodiments comprising a salt M-X dissolved in aqueous solution at a molar concentration from about 0.1 mM to about 150 mM and a cationic lipid are administered to lung tissue. Preferred modes for administration to lung tissue are disclosed in Wheeler, C. J., et al., *Proc. Natl. Acad. Sci. USA* 93:11454–11459 (1996), which is incorporated herein by reference in its entirety.

According to the disclosed methods, compositions of the present invention are preferably administered by intramuscular (i.m.), subcutaneous (s.c.), or intrapulmonary routes. Other suitable routes of administration include, but not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e, into or through skin or mucosal tissue). Intracavity administration includes, but not limited to adminitration into oral, vaginal, rectal, nasal, peritoneal, or intestinal cavities as well as, intrathecal (i.e., into spinal canal), intraventricular (i.e., into the brain ventricles or the heart ventricles), inraatrial (i.e., into the heart atrium) and sub arachnoid (i.e., into the sub arachnoid spaces of the brain) administration.

Any mode of administration can be used so long as the mode results in the expression of the desired peptide or protein, in the desired tissue, in an amount sufficient to be detectable, and/or prophylactically or therapeutically effective. Administration means of the present invention include needle injection, catheter infusion, biolistic injectors, particle accelerators (e.g., "gene guns" or pneumatic "needleless" injectors) Med-E-Jet (Vahlsing, H., et al., *J. Immunol. Methods* 171,11–22 (1994)), Pigjet (Schrijver, R., et al., *Vaccine* 15, 1908–1916 (1997)), Biojector (Davis, H., et al., *Vaccine* 12, 1503–1509 (1994); Gramzinski, R., et al., *Mol. Med*4, 109–118 (1998)), AdvantaJet (Linmayer, I., et al., *Diabetes Care* 9:294–297 (1986)), Medi-jector (Martins, J., and Roedl, E. *J. Occup. Med.* 21:821–824 (1979)), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, Y., et al., *Life Sciences* 65, 2193–2203 (1999)) or topical applications during surgery. The preferred modes of administration are intramuscular needle-based injection and pulmonary application via catheter infusion. Each of the references cited in this paragraph is incorporated herein by reference in its entirety.

Determining an effective amount of a composition depends upon a number of factors including, for example, the chemical structure and biological activity of the substance, the age and weight of the subject, the precise condition requiring treatment and its severity, and the route of administration. Based on the above factors, determining the precise amount, number of doses, and timing of doses are within the ordinary skill in the art and will be readily determined by the attending physician or veterinarian.

Compositions of the present invention can be formulated according to known methods. Suitable preparation methods are described, for example, in *Remington's Pharmaceutical Sciences*, 16$^{th}$ Edition, A. Osol, ed., Mack Publishing Co., Easton, Pa. (1980), and *Remington's Pharmaceutical Sciences*, 19$^{th}$ Edition, A. R. Gennaro, ed., Mack Publishing Co., Easton, Pa. (1995), both of which are incorporated herein by reference in their entireties. Although the composition is preferably administered as an aqueous solution, it can be formulated as an emulsion, gel, solution, suspension, lyophilized form, or any other form known in the art. According to the present invention, if the composition is formulated other than as an aqueous solution, it will require resuspension in an aqueous solution prior to administration. In addition, the composition may contain pharmaceutically acceptable additives including, for example, diluents, binders, stabilizers, and preservatives.

For aqueous compositions used in vivo, the use of sterile pyrogen-free water is preferred. Such formulations will contain an effective amount of a polynucleotide together with a suitable amount of an aqueous solution in order to prepare pharmaceutically acceptable compositions suitable for administration to a vertebrate.

Pharmaceutical Kits

The present invention also provides kits for use in delivering a polypeptide to a vertebrate. Each kit includes a container holding about 1 ng to about 30 mg of a polynucleotide which operably encodes a polypeptide within vertebrate cells in vivo. Furthermore, each kit includes either (a) an amount of a salt M-X which, when dissolved in a prescribed volume of distilled water, results in an aqueous solution with a molar concentration of said salt from about 20 mM to about 300 mM, and reaction, association, or dissociation products thereof, where M is an alkali metal (e.g., Li+, Na+, K+, Rb+), preferably sodium or potassium, and where X is an anion selected from the group consisting of phosphate, acetate, bicarbonate, sulfate, pyruvate, and an organic monophosphate ester, preferably glucose 6-phosphate or DL-α-glycerol phosphate; and optionally, an administration means; whereby the polynucleotide is provided in a prophylactically or therapeutically effective amount to treat a vertebrate; (b) an auxiliary agent such as, but not limited to DMSO, n-octylglucoside, IGEPAL CA 630®, NP-40®, Nonidet P40, Triton X100™, Triton X-114™, sodium dodecyl sulfate, Pluronic® F68, Pluronic® F77, Pluronic® P65, Pluronic(® L64, Pluronic® F108, Pluronic(® R 25R2, Tween-20®, Tween-80®, stachyose, and EDTA; and optionally, an administration means; whereby the polynucleotide is provided in a prophylactically or therapeutically effective amount to treat a vertebrate; or (c) an amount of a salt M-X which, when dissolved in an prescribed volume of distilled water, results in an aqueous solution with a molar concentration of said salt from about 0.1 mM to about 150 mM, and reaction, association, or dissociation products thereof, where M is an alkali metal (e.g., Li+, Na+, K+, Rb), preferably sodium or potassium, and where X is an anion selected from the group consisting of phosphate, acetate, bicarbonate, sulfate, pyruvate, and an organic monophosphate ester, preferably glucose 6-phosphate or DL-α-glycerol phosphate, and where the aqueous solution formed thereby is essentially free of chloride anion; a cationic lipid; and optionally, an administration means; whereby the polynucleotide is provided in a prophylactically or therapeutically effective amoun. Any of the components of the pharmaceutical kits (a) through (c) can be provided in a single container or in multiple containers. The aqueous solutions of (a) and (c) may further include an auxiliary agent as described in kit (b). Preferably, the kit includes from about 1 ng to about 30 mg of a polynucleotide, more preferably, the kit includes from about 100 ng to about 10 mg of a polynucleotide.

Any suitable container or containers may be used with pharmaceutical kits. Examples of containers include, but are not limited to, glass containers, plastic containers, or strips of plastic or paper.

Each of the pharmaceutical kits may further comprise an administration means. Means for administration include, but are not limited to syringes and needles, catheters, biolistic injectors, particle accelerators, i.e., "gene guns," pneumatic "needleless" injectors, gelfoam sponge depots, other commercially available depot materials, e.g., hydrogels, osmotic pumps, and decanting, polynucleotide coated sutures, skin patches, or topical applications during surgery.

Each of the pharmaceutical kits can further comprise an instruction sheet for administration of the composition to a vertebrate. The polynucleotide components of the composition are preferably provided as a liquid solution or they may be provided in lyophilized form as a dried powder or a cake. If the polynucleotide is provided in lyophilized form, the dried powder or cake may also include any salts, auxiliary agents, transfection facilitating agents, and additives of the composition in dried form. Such a kit may further comprise a container with an exact amount of sterile pyrogen-free water, for precise reconstitution of the lyophilized components of the composition.

The container in which the composition is packaged prior to use can comprise a hermetically sealed container enclosing an amount of the lyophilized formulation or a solution containing the formulation suitable for a pharmaceutically effective dose thereof, or multiples of an effective dose. The composition is packaged in a sterile container, and the hermetically sealed container is designed to preserve sterility of the pharmaceutical formulation until use. Optionally, the container can be associated with administration means and/or instruction for use.

The following examples are included for purposes of illustration only and are not intended to limit the scope of the present invention, which is defined by the appended claims. All references cited in the Examples are incorporated herein by reference in their entireties.

EXAMPLES

The following examples demonstrate the surprising finding that compositions comprising polypeptide-encoding polynucleotides and certain salts and/or auxiliary agents can enhance subsequent gene expression when administered into murine tissues.

Materials and Methods

The following materials and methods apply generally to all the examples disclosed herein. Specific materials and methods are disclosed in each example, as necessary.

Preparation of the Pharmaceutical Compositions

All salts used in the following examples are available from Sigma Chemical Corporation (Sigma, St. Louis, Mo.). Detergents used in the following examples are available from Sigma, Roche Molecular Biochemicals (Indianapolis, Ind.), BASF (Mount Olive, N.J.), and Amresco (Solon, Ohio). Purified plasmid DNA was ethanol precipitated and resuspended in water. Salt solutions were prepared as 200 mM to 300 mM stock solutions and dilutions were made using sterile USP water (Baxter, Deerfield, Ill.).

Preparation of Plasmid DNAs

FIG. 1 depicts the major structural and regulatory elements contained in each plasmid. The gene for *Photinus pyralis* (firefly) luciferase was subcloned from the pSP-LuC vector (available from Promega, Madison, Wis.) into the VR1012 vector (Hartikka, J., et al., *Hum. Gene Ther.* 7:1205–1217 (1996)) to make VR1223 or VR1255 (Hartikka, J., et al., *Hum. Gene Ther.* 7:1205–1217 (1996)). The RSV promoter-regulated VR1418 LacZ vector was made by subcloning the LacZ gene from the VR1412 vector (Doh, S. G., et al., *Gene Ther.* 4:648–663 (1997)) into VR1043, itself derived by replacing the CMV control elements of VR1012 with RSV control elements. The mouse erythropoietin (EPO) was obtained by PCR as described (Tripathy, S. K., et al., *Proc. Natl. Acad. Sci. USA* 93:10876–10880 (1996)) and subcloned into the VR1012 vector to produce VR2901. The secreted form of the human placental alkaline phosphatase (SEAP) gene was subcloned from pSEAP2-Basic (available from Clonetech, Palo Alto, Calif.) into the VR1012 backbone vector to make VR3301. The rat preproinsulin coding sequence was obtained from reverse transcription of rat pancreatic preproinsulin poly(A) mRNA as described (Abai, A. M., et al., *Hum. Gene Ther.* 10:2637–2649 (1999)) and subcloned into the VR1012 backbone vector to produce VR3502. The human IFN-ω coding sequence was obtained by amplifying the coding sequence from human genomic DNA prepared from DNA of fresh human blood. The mouse IFN-α gene was a generous gift from Paula Pitha-Rowe (Johns Hopkins University). The IFN-ω and IFN-α genes were subcloned into the VR1055 vector to produce, respectively VR4151 and VR4111 as described (Horton, H. M., et al., *Proc. Natl. Acad. Sci. USA* 96:1553–1558 (1999)). The luciferase gene in VR1255 was replaced with the influenza A/PR/8/34 nucleoprotein gene as described (Ulmer, J. B., et al., *Ann. N.Y. Acad. Sci.* 772:117–125 (1995)) to yield VR4700.

Plasmid DNA Purification

Plasmid DNA was transformed into *Escherichia coli* DH5α competent cells and highly purified covalently closed circular plasmid DNA was isolated by a modified lysis procedure (Horn, N. A., et al., *Hum. Gene Ther.* 6:565–573 (1995)) followed by standard double CsCl-ethidium bromide gradient ultracentrifugation (Sambrook, J., et al., *Molecular Cloning: A Laboratory Manual*, 2nd Ed., Cold Spring Harbor Laboratory Press, Plainview, N.Y. (1989)). Alternatively, SEAP and preproinsulin encoding plasmid DNAs were purified using Giga columns from Qiagen (Valencia, Calif.) according to the kit instructions. All plasmid preparations were free of detectable chromosomal DNA, RNA and protein impurities based on gel analysis and the bicinchoninic protein assay (Pierce Chem. Co., Rockford Ill.). Endotoxin levels were measured using Limulus Amebocyte Lysate assay (LAL, Associates of Cape Cod, Falmouth, Mass.) and were less than 0.6 Endotoxin Units/mg of plasmid DNA. The spectrophotometric $A_{260}/A_{280}$ ratios of the DNA solutions were typically above 1.8. Plasmids were ethanol precipitated and resuspended in water at 4° C. until completely dissolved. DNA was stored at −20° C. until use. DNA was diluted by mixing it with 300 mM salt solutions and by adding appropriate amount of USP water to obtain 1 mg/ml plasmid DNA in the desired salt at the desired molar concentration.

Injections of Plasmid DNA

The quadriceps muscles (or tibialis anterior muscles for SEAP plasmids) of restrained awake mice (female 6–12 week old BALB/c or Nude, nu/nu, from Harlan Sprague Dawley, Indianapolis, Ind.) were injected with 50 µg of DNA in 50 µl solution using a disposable sterile, plastic insulin syringe and 28G ½ needle (Becton-Dickinson, Franklin Lakes, N.J., Cat. No. 329430) fitted with a plastic collar cut from a micropipette tip, all as previously described (Hartikka, J., et al., *Hum. Gene Ther.* 7:1205–1217 (1996)). The tissues were extracted and assayed as described in Manthorpe, M., et al., "Quantification of plasmid DNA expression in vivo," in *Gene Quantification*, Ferre, F., ed., F. Birkhäuser, Boston, Mass. (1998), pp. 343–368. Briefly, tissues were rapidly collected and frozen, they were combined with and frozen into a lysis buffer, the tissue was then pulverized with a drill bit run in reverse direction, the resulting powder was thawed, and was extracted two times with extraction buffer. Nude mice were injected with VR3301 DNA bilaterally on three consecutive days for a total of 300 µg DNA per mouse. Lungs were instilled with 132 µg plasmid DNA complexed with GAP-DLRIE/DOPE in solution and extracted all as described (Wheeler, C. J., et al., *Proc Natl Acad Sci USA* 93:11454–11459 (1996)).

Animal care throughout the study was in compliance with the "Guide for the Use and Care of Laboratory Animals", Institute of Laboratory Animal Resources, Commission on Life Sciences, National Research Council, National Academy Press, Washington, D.C., 1996 as well as with Vical's Institutional Animal Care and Use Committee.

Enzyme Assays

Luciferase activity was assayed using a Dynatech model ML2250 microplate luminometer (Chantilly, Va.) as previously described (Hartikka, J., et al., *Hum. Gene Ther.* 7:1205–1217 (1996)). The luciferase content of the samples was calculated from Relative Light Units using a standard curve of purified firefly luciferase (Analytical Luminescence Laboratory, San Diego, Calif.; Cat. No. 2400), which was diluted in pooled extract from uninjected muscles to control for quenching. Luciferase values were expressed as ng luciferase per muscle. The level of β-galactosidase expression in muscle extracts was quantified using a chemiluminescent assay according to the manufacturer's instructions (Roche Molecular Biochemicals, Indianapolis, Ind., Cat.

No. 1758241). A standard curve, prepared in pooled extract from uninjected muscles, was included on each plate using the β-galactosidase enzyme standard included in the kit.

Sera from nude mice injected with VR3301 were collected at various times post-injection. Five μl of serum was mixed with 15 μl distilled H$_2$O and placed into individual wells of a 96 well plate (e.g., Costar EIA/RIA A/2 #3690, available from Corning, Inc). A serial dilution of ETA grade calf intestinal alkaline phosphatase (CIP, available from Roche Molecular Biochemicals, cat. #567 744) in PBS containing 0.05% Bovine Serum Albumin (BSA) was used to produce a standard curve. Samples were assayed in duplicate. Plates were sealed, incubated at 65° C. for 30 min and spun for 5 min at 4000 rpm at room temperature. Each well received 100 μl substrate solution containing 1 mg/ml para-nitrophenyl phosphate (PNPP, available from Roche Molecular Biochemicals, cat. #107 905) and 1 mM MgCl$_2$ in 1M diethanolamine, pH 9.8. The samples were analyzed using a Molecular Devices Opti Max plate reader (Sunnyvale, Calif.). The plate reader was pre-warmed to 37° C. and a standard kinetic program was used to assay the samples at a wavelength of 405 nm for 30 min.

NP, Proinsulin, and β-galactosidase ELISA

Sera were collected at different times before and after plasmid DNA injections. Ninety-six well plates (available from Corning Incorporated, Acton, Mass., Cat. No. 3690) were coated with 36 ng/50 μl of Borate Buffered Saline (BBS)/well of NP purified from recombinant baculoviral extracts (available from Imgenix Corporation), commercial rat proinsulin (available from Crystal Chem, Chicago, Ill.) or 5 μl/50 μl of β-galactosidase protein (available from Sigma). The plates were stored overnight at +4° C. and the wells washed twice with Borate Buffered Saline Tween (BBST) (89 mM Boric Acid+90 mM NaCl, pH 8.3+234 mM NaOH supplemented with 0.05% Tween 20® (v/v)). The wells were then incubated 90 minutes with BB (BBST in which the Tween was replaced with 5% non-fat milk in 1×BBS) and washed twice with BBST again. Two-fold serial dilutions of mouse serum in BB starting at 1:20 were made in successive wells and the solutions were incubated for 2 hours at room temperature. Wells were then rinsed four times with BBST. Sera from mice hyperimmunized with VR4700 NP, VR3502, or VR1412 plasmid DNA were used as a positive control and pre-immune sera were used as negative controls.

To detect specific antibodies, alkaline phosphatase conjugated goat anti-mouse IgG-Fc (e.g., from Jackson Immunoresearch Laboratories, Inc. West Grove, Pa., Cat. No. 115-055-008) diluted 1:5000 in BBS were added at 100 μg/well and the plates were incubated at room temperature for 2 hours. After 4 washings in BBST, the substrate (1 mg/ml p-nitrophenyl phosphate, e.g., from Calbiochem-Novabiochem Corp., San Diego, Calif., Cat. No. 4876 in 50 mM sodium bicarbonate buffer, pH 9.8 and 1 mM MgCl$_2$) was incubated for 90 min at room temperature and absorbance readings were performed at 405 nm. The titer of the sera was determined by using the reciprocal of the last dilution still giving a signal two times above background. Background was established using pre-immune serum diluted 1:20. Serum concentrations of human IFN-ω were measured using a commercially available kit with a detection limit of 2 pg/ml (available from Alexis Corp., San Diego, Calif.).

Hematocrit Measurements

Hematocrits were measured by centrifugation of blood obtained from the retro-orbital cavity of mice. Blood samples were collected in 75 μl heparinized capillary tubes and analyzed using HemaSTAT II microhematocrit centrifuge (Separation Technology, Inc., Altamonte Springs, Fla.).

Histology

For whole muscle staining, quadriceps were fixed for 3 hours at room temperature in 2% paraformaldehyde in PBS, washed 3 times for 20 min each in PBS and incubated for 18 hours at 37° C. in a solution containing 2 mM MgCl$_2$, 5 mM potassium ferricferrocyanide and 1 mg/ml 5-bromo-4-chloro-3-indoyl-β-D-galactosidase (available from Life Technologies, Inc. (LTI), Gaithersberg, Md.) in PBS. After incubation, the muscles were washed 3 times for 10 min each in 3% dimethyl sulfoxide in PBS and stored in PBS at 4° C. until analysis. To prepare stained tissue cross sections, quadriceps were snap-frozen in liquid nitrogen-cooled isopentane, cut in half, embedded in OCT medium (available from VWR, McGraw Park, Ill.) and 10 μm sections were cut using a Jung Frigocut Model 2800E cryostat (Leica, Foster City, Calif.). Sections were collected on 1% gelatin coated glass slides, brought to room temperature and stained for 2 hours at 37° C. in the same reagent as for whole mounts above except that the beta-galactosidase reagent concentration was 200 μg/ml. The sections were then counterstained with Harris hematoxylin in acetic acid, rinsed in tap water, dehydrated and mounted in Permount (Fisher, Fair Lawn, N.J.). The number of β-galactosidase positive cells per muscle was determined by light microscopy in muscle cross-sections as described (Doh, S. G., et al., Gene Ther. 4:648–663 (1997)).

Splenocyte CTL Stimulation Cultures

To generate CTL effector cells from BALB/c mice immunized with plasmid DNA encoding influenza A/PR/8/34 nucleoprotein, splenocytes were stimulated in culture for 5 days with $NP_{147-155}$ peptide (TYQRTRALV) pulsed, irradiated splenocytes from naive BALB/c mice. For the stimulation cultures, splenocytes from naïve mice were γ-irradiated with 3200 Rads and pulsed with 10 μM of the H-2K$^d$ restricted $NP_{147-155}$ peptide for 40 min at 37° C. Then, 2.5×10$^7$ test splenocytes from DNA immunized mice were incubated at 37° C. in 5.5% CO$_2$ with an equal number of irradiated, pulsed splenocytes from naive mice in 25 cm$^2$ flasks containing 25 ml RPMI 1640 media with L-glutamine and 25 mM HEPES supplemented with 10% fetal bovine serum, penicillin (100 U/ml), streptomycin (100 μg/ml) and 5.5×10$^{-5}$ M β-mercaptoethanol). Tissue culture reagents are all available from LTI. After 24 hours of culture, recombinant murine IL-2 was added to a final concentration of 1 U/ml.

$^{51}$Cr Release Assay

To measure specific lysis of $NP_{147-155}$ peptide pulsed target cells by CTL effector cells, P815 cells (available from the American Type Culture Collection, Manassas, Va.) were labeled with Na$_2$$^{51}$CrO$_4$ (NEN Life Scientific Products, Inc., Boston, Mass.). Aliquots of $^{51}$Cr labeled cells were either pulsed with 10 μM $NP_{47-155}$ or were used unpulsed. For the CTL assay, stimulated splenocytes were serially diluted in 96 well round bottom microtiter plates (available from ICN Biomedicals, Inc., Aurora, Ohio). Target cells were added in a final volume of 100 μl/well. After incubation for 5 hours at 37° C. in 5.5% CO$_2$, 100 μl of RPMI 1640 complete media was added to each well, the plates were centrifuged and 100 μl/well was removed for analysis in a Cobra II gamma counter (Packard Instruments Co., Downers Grove, Ill.). The percentage of specific lysis was calculated as % specific lysis=(a−b/c−b)100 where a is the average cpm released in the presence of effectors, b is the average spontaneous cpm released from target cells incubated in media only and c is the maximum cpm released from target cells in the presence of 1% Triton X-100™.

Statistical Evaluations

All statistical comparisons from tissue expression data were performed using the non-parametric Mann-Whitney rank sum test (SigmaStat version 2.03, Jandel Scientific Software, San Rafael, Calif.) and where indicated by the standard Student T-Test. Differences by all statistical methods were considered statistically significant when the p value was less than 0.05.

Example 1

Effect of Various Solutions Containing Sodium Chloride and Sodium Phosphate on Luciferase Plasmid DNA Expression in Murine Muscles The purpose of the present example is to demonstrate the ability of certain salt solutions to increase the levels of plasmid DNA expression when injected into muscle compared with plasmid DNAs formulated in normal saline.

Mouse quadriceps muscles were injected with 50 µg of plasmid VR1223, encoding luciferase, dissolved in 50 µl of either water, saline, PBS, saline plus 100 mM sodium phosphate, 100 mM NaCl, or 100 mM NaCl plus 50 mM sodium phosphate. The muscles were extracted and assayed for luciferase activity 7 days later. The results are shown in Table I. When the plasmid was dissolved in distilled water, luciferase expression was 25-times lower than when the plasmid was dissolved in saline (4 vs. 119 ng lux/muscle). Injection of the plasmid dissolved in PBS (i.e., saline plus 10 mM sodium phosphate) elicited a marginal, but statistically higher 1.6-fold expression level than saline (186 vs. 119 ng luciferase per muscle, p=0.02). Delivery of the plasmid in a hypertonic solution containing saline plus 100 mM sodium phosphate reduced expression to the level obtained using saline alone (117 vs. 119 ng lux/muscle). A hypoosmotic 100 mM NaCl solution yielded the same expression as isoosmotic saline (112 vs 119 ng lux/muscle), but restoration of osmolarity by the addition of 50 mM sodium phosphate to the 100 mM NaCl increased expression by 1.8 fold (112 vs 203 ng lux/muscle, p=0.03). Thus, sodium phosphate increased luciferase expression.

Example 2

Effect of the Molar Concentration of Sodium Phosphate and pH on Luciferase Plasmid DNA Expression in Murine Muscles The effect of sodium phosphate concentration and pH on the level of luciferase expression from injected plasmid DNA in murine muscles was tested as follows. Plasmid VR1223 DNA was dissolved in solutions containing different concentrations of sodium phosphate in the absence of NaCl, and these were tested for day 7 luciferase expression in quadriceps muscle as described in Example 1 above. The molar concentrations of sodium phosphate tested ranged from 2.5 mM to 300 mM. The averaged data from 5 separate experiments are shown in FIG. 2A. Peak expression occurred when the plasmid DNA was dissolved in 150 mM sodium phosphate, which yielded 386 ng luciferase per muscle which is 4.3-fold higher than the average expression level observed when the DNA is dissolved in saline (indicated by the dashed line at 89 ng luciferase per muscle, p<0.001). The expression levels observed when the DNA was dissolved in 80 mM, 100 mM, 150 mM, and 200 mM sodium phosphate solutions were significantly higher than saline by Mann-Whitney rank sum test (p<0.05). Injection of plasmid DNA dissolved in solutions having sodium phosphate concentrations below 40 mM (in the absence of added chloride ion) or above 300 mM resulted in luciferase expression levels equal to or lower than those seen with saline.

Figure 2B:
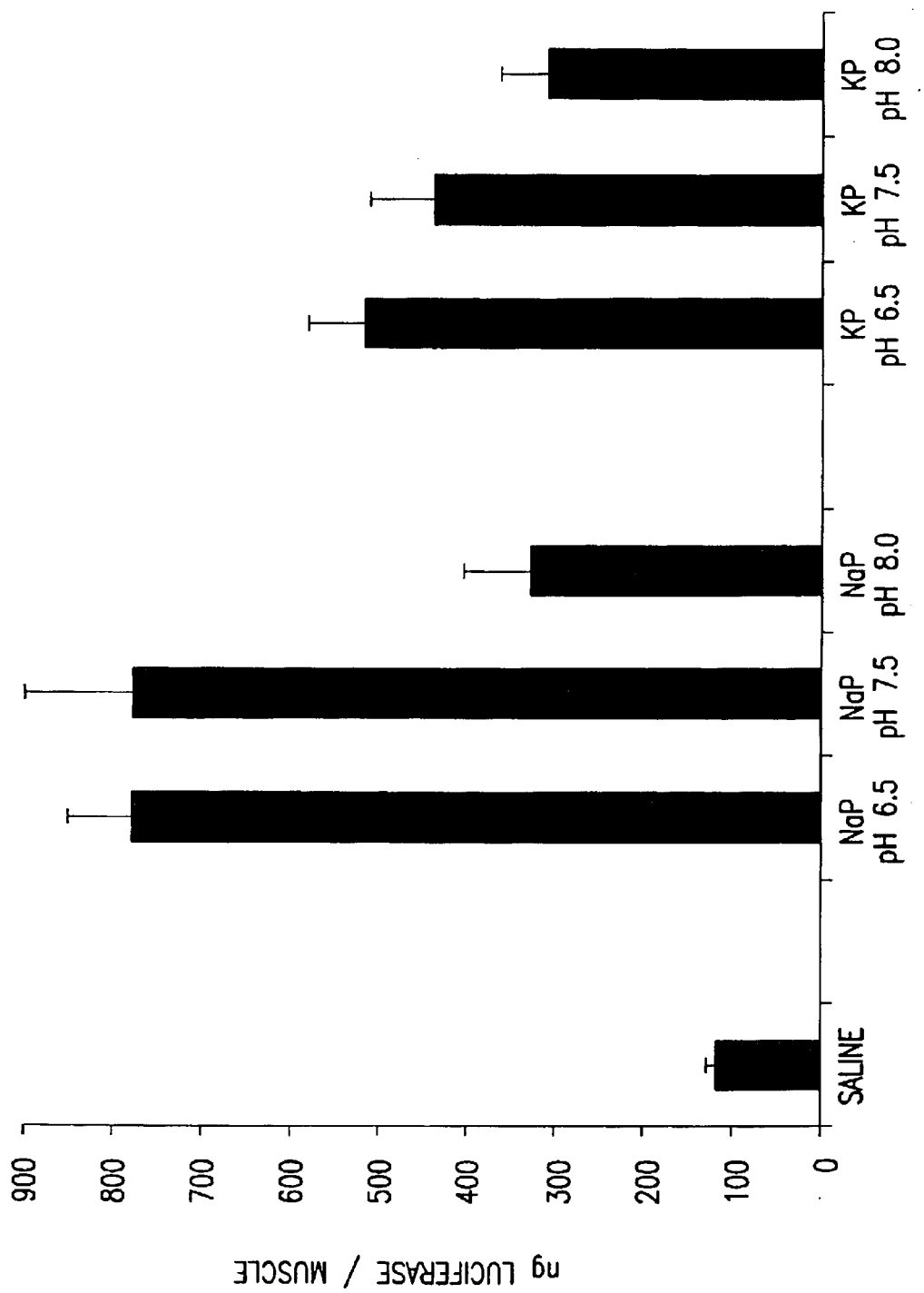
FIG. 2C is a graph plotting the effect of pH of the various salt solutions listed in Table III on luciferase expression in mouse muscle.
FIG. 2D is a graph plotting the effect of osmolarity of the various salt solutions listed in Table III on luciferase expression in mouse muscle.

To examine the effect of pH, plasmid VR1223 was dissolved in 150 mM sodium phosphate or potassium phosphate at pHs of 6.5, 7.5 or 8.0 and was tested for day 7 expression in quadriceps muscle as described in Example 1 above. The results indicated that the optimal pH is about 6.5 to 7.5, with pH 8.0 being suboptimal (FIG. 2B).

Example 3

Effect of Alternate Salt Solutions on Luciferase Plasmid DNA Expression in Murine Muscles In this example, injection of plasmid DNA encoding luciferase dissolved in 150 mM solutions of various salts which vary either the cation or the anion of normal saline were compared with saline for their ability to stimulate luciferase expression in murine muscle. The results are shown in Table II.

Table IIA shows the effect on luciferase expression when the plasmid DNA is dissolved in a solution of a salt where the sodium cation in saline is replaced with other cations. Plasmid VR1223 dissolved in the various solutions was tested for day 7 expression in quadriceps muscle as described in Example 1 above. Two salts, $ZnCl_2$ and $FeCl_2$, were only tested in 2 or 3 mice since these salts appeared to cause pain. Solutions containing divalent cations, e.g., magnesium ($Mg^{2+}$), calcium ($Ca^{2+}$), zinc ($Zn^{2+}$) and ferrous iron ($Fe^{2+}$), greatly decreased expression while the solution containing the monovalent cation potassium ($K^+$) elicited the same expression as the monovalent sodium cation ($Na^+$).

Table IIB shows the effect on luciferase expression when the plasmid DNA is dissolved in a solution of a salt where the sodium cation in sodium phosphate was replaced with various other cations. Plasmid VR1223 dissolved in the various solutions was tested for day 7 expression in quadriceps muscle as described in Example 1 above. Just as replacing the sodium cation in saline with potassium cation did not affect luciferase expression, replacing the sodium cation in sodium phosphate with potassium cation also had no effect. Thus, a solution of 150 mM potassium phosphate stimulated expression just as well as solution of 150 mM sodium phosphate when both were compared with saline. When plasmid DNA was dissolved in 150 mM solutions of dibasic or monobasic sodium phosphate (not adjusted for pH), luciferase expression was only slightly stimulated over saline. The best stimulation of expression occurred when the plasmid DNA was dissolved in a 150 mM solution of sodium or potassium phosphates which is a mixture of the dibasic and monobasic forms balanced to achieve the desired pH (in this case, pH 7.0). Other phosphate salts tested (i.e., when the cation was $Mg^{2+}$, $Ca^{2+}$, $Al^{3+}$ or $Fe^{3+}$) resulted in inhibited expression relative to saline.

Table IIC shows the effect on luciferase expression when the plasmid DNA is dissolved in a solution of a salt where the phosphate anion in 150 mM sodium phosphate was replaced with various other anions. Plasmid VR1223 dissolved in the various solutions was tested for day 7 expression in quadriceps muscle as described in Example 1 above. Injection of the plasmid DNA in solutions of the sodium salts of acetate, pyruvate, bicarbonate and sulfate all increased luciferase expression compared with saline. Sodium citrate yielded the same luciferase expression as saline but sodium oxalate inhibited luciferase expression. Thus, according to Table IIC, stimulatory effects of various 150 mM salt solutions can be ranked in order of their relative enhancement of luciferase expression as follows: sodium phosphate=potassium phosphate=sodium acetate>sodium pyruvate=sodium bicarbonate=sodium sulfate>saline= potassium chloride=sodium citrate. The rest of the solutions tested inhibited expression compared with saline.

Figure 2D:
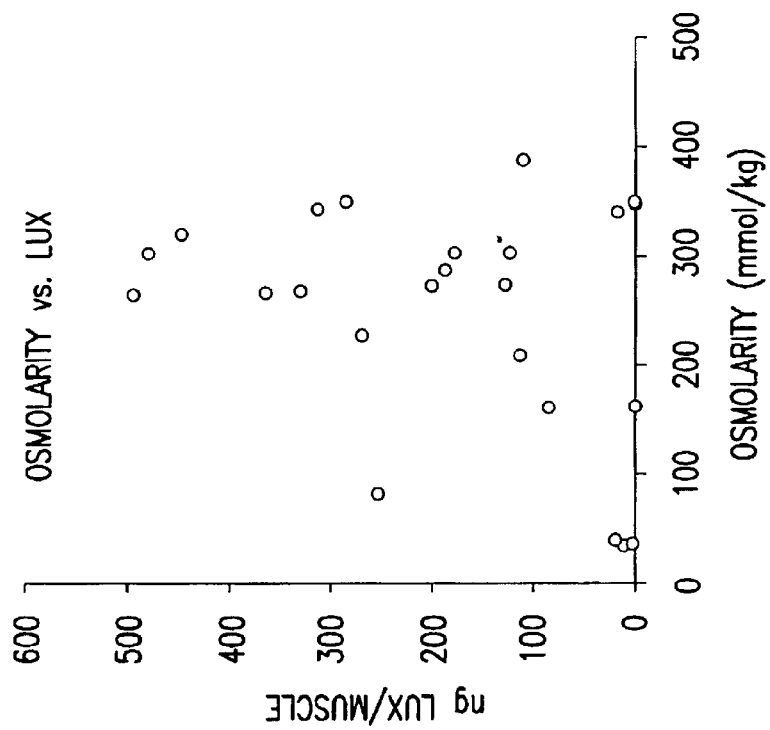
Figure 2C:
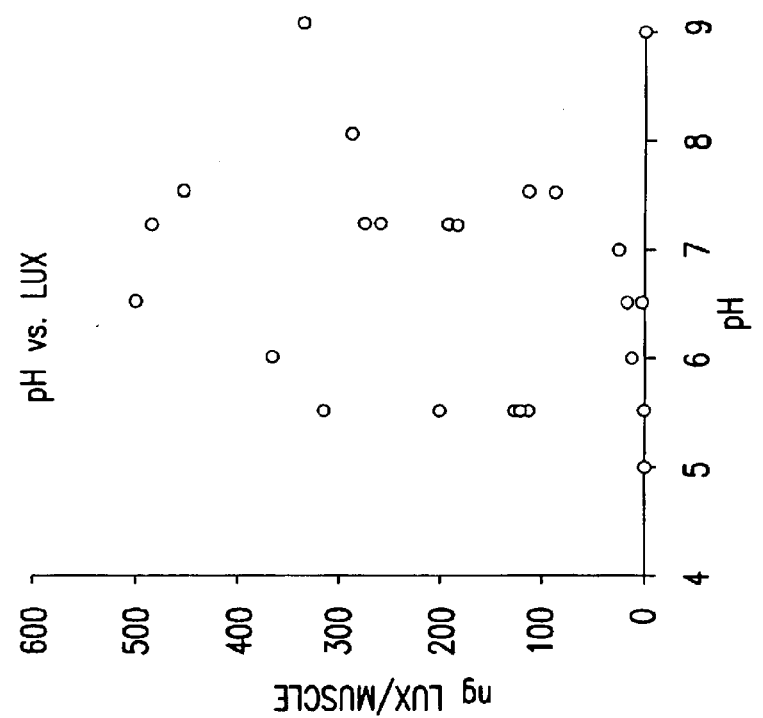

The effects of osmolarity and pH on the ability of certain salt solutions to enhance luciferase expression in murine muscle was tested as follows. The osmolarity and pH of each salt solution (150 mM concentration unless otherwise indicated) shown in Table III was measured and plotted vs. the 7-day luciferase expression level obtained with that solution (FIGS. 2C and 2D). The pH values and osmolarities of the various salt solutions, as well as the relative 7-day luciferase expression observed when plasmid VR1223 was dissolved in each solution and injected into murine muscle, are shown in Table III. The osmolarity graph (FIG. 2D) revealed that solutions with osmolarities between 271 and 349 mmol/kg generally yielded the highest expression levels but exceptions included 50 mM and 100 mM sodium phosphate at 83 and 270 mmol/kg (respective expression levels 2.1 and 2.3 fold those of saline at 310 mmol/kg) and sodium citrate at 394 mmol/kg (expression level was the same as with saline). The 150 mM sodium phosphate solution yielded an expression level that was 4-fold higher than that of saline, yet both solutions had the same osmolarity (310 vs. 308 mmol/kg, respectively). The pH graph (FIG. 2C) revealed that the highest expression levels were generally obtained with solutions at pH 6.0 to 7.5. However, some exceptions were sodium sulfate, pH=5.5, and sodium bicarbonate, pH 9.0, which yielded expression levels that were 2.6 and 2.8-fold, respectively, over saline at pH 5.5. Furthermore, the magnesium phosphate solution had a pH=7.0 but yielded an expression level lower than saline.

The reproducibility of enhanced luciferase DNA expression when the plasmid DNA is dissolved in a solution of 150 mM sodium phosphate was tested as follows. Nine different experiments were carried out to test luciferase expression levels when plasmid VR1223 was dissolved in 150 mM sodium phosphate for injection into mouse skeletal muscle. In each of the experiments, 10 quadriceps muscles were injected with 50 $\mu$g of plasmid VR1223 in 50 $\mu$l of either saline or 150 mM sodium phosphate. Muscles were collected and assayed for luciferase expression at 7 days. The averaged results for each experiment are shown in FIG. 3. Compared with saline, sodium phosphate enhanced luciferase expression in all 9 experiments, with the enhancement ranging from 2.5-fold (156 vs. 384 ng lux/muscle for Exp. #9) to 7.3-fold (49 vs. 362 ng lux/muscle in Exp. #1). In these replicate experiments, the average enhancement by sodium phosphate for all 9 experiments was 4.1-fold (120 vs. 490 ng luciferase/muscle).

Example 4

Expression of β-galactosidase and Human Interferon-omega Following Intramuscular Injection of Plasmid DNA is Enhanced when the Plasmid is Injected in a Sodium Phosphate Solution The effect of a sodium phosphate solution on the expression of polypeptides other than luciferase following intramuscular injection of plasmid DNAs encoding the polypeptides was examined as follows. Plasmids encoding non-secreted β-galactosidase (VR1418) and secreted human interferon-omega (IFN-ω; VR4151) in saline or 150 mM sodium phosphate were injected into mouse quadriceps as described in the materials and methods and Example 1. Muscle extracts were assayed for β-galactosidase and the serum was assayed for circulating levels of IFN-ω. The 7 day post-DNA injection protein expression data, including luciferase plasmid DNA run in parallel for comparison, are shown in FIG. 4. Injection of the plasmid DNAs dissolved in 150 mM sodium phosphate enhanced expression of all three proteins over saline. Compared with saline, injection of plasmid DNA in 150 mM sodium phosphate enhanced expression of luciferase in muscle by 4.8-fold (769 vs. 159 ng/muscle; p<0.001), β-galactosidase in muscle by 3.3-fold (9.8 vs. 3.0 ng/muscle; p=0.001) and serum IFN-ω) levels by 2.5-fold (0.35 vs. 0.14 ng ml serum; p=0.020).

Plasmid DNA dissolved in PBS, run in parallel, elicited statistically equivalent expression as saline for the plasmids encoding β-galactosidase and IFN plasmids (data not shown).

Plasmid DNA VR1418 encoding β-galactosidase was dissolved in sodium phosphate solutions at the various molar concentrations tested in Example 2. Quadriceps muscles were injected with 50 $\mu$l of each solution containing 10 $\mu$g of plasmid VR1418, and the muscles were tested for 7-day expression levels. As with luciferase expression, as shown in Example 2, 150 mM sodium phosphate was the optimal molar concentration for β-galactosidase expression (data not shown). This similar effect occurred despite the fact that the β-galactosidase gene on VR1418 is driven by an RSV promoter, rather than the CMV promoter which drives expression of luciferase on plasmid VR1223 and IFN-ω on plasmid VR4151, and despite the fact that 10 $\mu$g of plasmid DNA was injected per muscle rather than 50 $\mu$g.

Example 5

Expression of Human Placental Alkaline Phosphatase, Rat Proinsulin and Mouse Erythropoietin Following Intramuscular Injection of Plasmid DNA is Enhanced when the Plasmid is Injected in a Sodium Phosphate Solution Three different plasmid DNAs encoding a secreted form of human placental alkaline phosphatase (SEAP; VR3301), rat preproinsulin (VR3502) or mouse erythropoietin (EPO; VR2901) were injected into mouse skeletal muscle in saline or 150 mM sodium phosphate solutions as described in the Materials and Methods and in Example 1. The mice were monitored over time for blood levels of SEAP or proinsulin or for hematocrits. The results are shown in FIG. 5. In the case of SEAP, plasmid DNA was injected into the tibialis anterior muscles, and nude mice were used to prevent an immune response to the foreign transgene product. The kinetics of blood SEAP levels from mice injected with DNA dissolved in both saline and 150 mM sodium phosphate were similar. SEAP protein expression rose to a peak level at 7 days, then declined to 40–45% of the maximum expression level where it remained for two months. The Sodium phosphate solution significantly enhanced SEAP expression by 1.4 to 1.8-fold compared with saline (n=15; p 0.002 to 0.037) over the time course. A parallel experiment using PBS showed expression to be statistically equivalent to that obtained with saline (data not shown). Thus, injection of plasmid DNA dissolved in a 150 mM sodium phosphate solution resulted in a higher level of sustained expression than when dissolved in saline.

Plasmid DNA encoding rat preproinsulin, dissolved in either 150 mM sodium phosphate or saline, was injected into the muscles of immunocompetent mice. Injection of the plasmid DNA in the sodium phosphate solution enhanced expression over a 2 week period by 1.9 to 3.8-fold compared with saline (n=10; p<0.01). Proinsulin expression eventually declined to very low levels in both groups, possibly due to the generation of measurable anti-proinsulin antibodies (data not shown).

Plasmid DNA encoding mouse EPO, dissolved in either 150 mM sodium phosphate or saline, was injected into the muscles of immunocompetent mice. Hematocrit levels, which correlate with the expression of erythropoeitin, rose steadily over 4 weeks. Control mice injected with 20 μg of DNA encoding canine Factor IX exhibited a constant hematocrit averaging 48. Injection of plasmid DNA dissolved in 150 mM sodium phosphate solution resulted in higher hematocrit levels than the injection of plasmid DNA dissolved in saline at all the time points tested. This enhancement ranged from 1.4 to 2.1-fold (n=10; p=0.02–0.001).

Example 6

Histological Analysis of Muscle Tissues Injected with Plasmid DNA Encoding β-galactosidase Dissolved in Either Sodium Phosphate or Saline Individual muscle cells were examined for β-galactosidase expression as follows. Twenty-six BALB/c quadriceps muscles each were injected with 50 μg of plasmid VR1412 DNA (expressing β-galactosidase) in 50 μl of either saline or 150 mM sodium phosphate, according to the methods disclosed in the Materials and Methods and in Example 1. FIGS. 6A to 6F show the muscles collected 7 days later and stained for β-galactosidase. A quantitative analysis of β-galactosidase-stained fibers using previously detailed methods (Doh, S. G., et al., Gene Ther. 4:648–663 (1997)) revealed a significantly greater number of β-galactosidase-stained myofiber cells in the sodium phosphate group than in the saline group. Cell counts of sections taken from the midline of 20 muscles (10 muscles for each group) revealed that the sodium phosphate group contained more β-galactosidase-positive myofiber cells than did the saline group (average of 108+/−21 vs. 186+/−43 myofiber cells/muscle section; p=0.02; n=10). Thus, plasmid DNA dissolved in 150 mM sodium phosphate apparently has an enhanced ability to transduce muscle cells relative to plasmid DNA dissolved in saline.

Example 7

Plasmid DNA Immunization Utilizing a Sodium Phosphate Solution

Figure 7B:
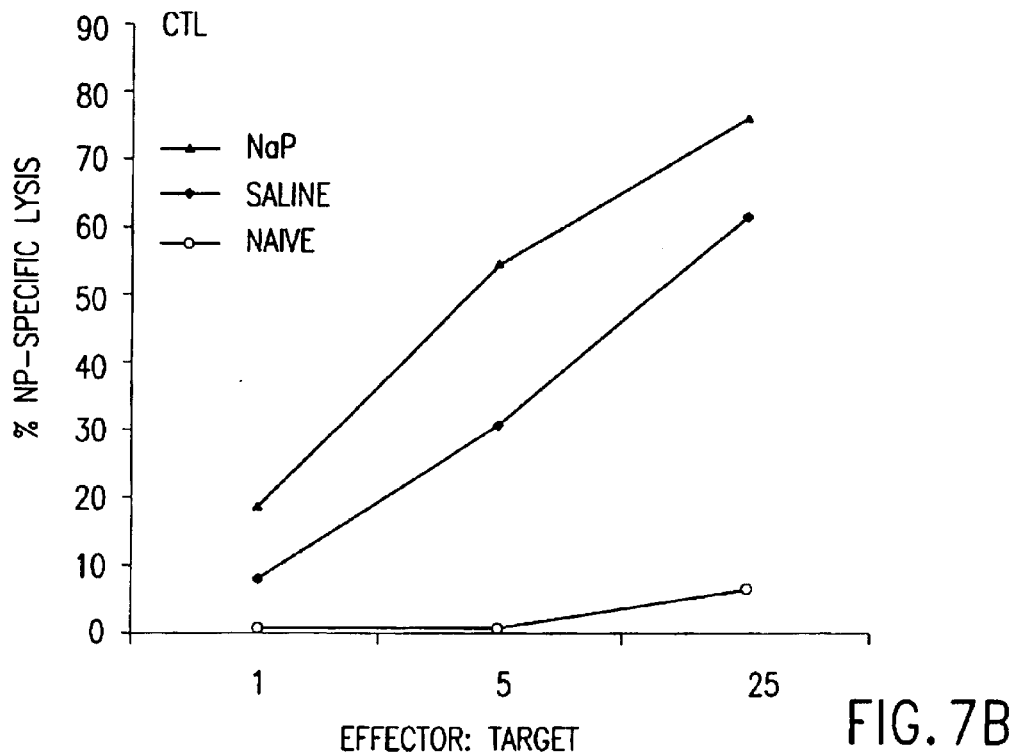

The effect of sodium phosphate on the elicitation of an immune response upon injection of plasmid DNA encoding an immunogen was examined as follows. Mice were vaccinated intramuscularly with plasmid VR4700, encoding the influenza nucleoprotein. The DNA was dissolved in either saline or 150 mM sodium phosphate. The mice were monitored for the presence of circulating anti-NP antibodies and for an NP-specific cytotoxic T lymphocyte response (CTL). The antibody data at 6 weeks and CTL data at 9 weeks post-vaccination are shown in FIG. 7. FIG. 7A shows that in three replicate experiments (labeled 1–3, n=9–10 mice per group per experiment), the sodium phosphate solution enhanced serum anti-NP antibody titers compared with saline solution. The enhancement by sodium phosphate was significant in all 3 experiments (p<0.04) as well as in the average of all three experiments (p<0.001). Plasmid VR VR4700, injected in PBS, was run in parallel and the antibody titers were not statistically different from the plasmid injected in saline (data not shown). FIG. 7B shows that anti-NP specific CTL activity was statistically similar (p>0.05) in the saline and 150 mM sodium phosphate group. A repeat set of CTL experiments showed the same result (data not shown).

Example 8

Polypeptide Expression in a Non-Muscle Tissue is Enhanced by Use of a Sodium Phosphate Solution and a Cationic Lipid for Delivery of Plasmid DNA The effect of a sodium phosphate solution on the enhancement of polypeptide expression from plasmid DNA delivered to a non-muscle tissue using a cationic lipid was evaluated as follows. Mouse lungs were instilled with plasmid VR1223 encoding luciferase combined with the cationic lipid GAP-DLRIE and co-lipid DOPE in water or selected concentrations of sodium phosphate as described in the Materials and Methods above. The use of DNA lipid complexes in water and collection at day 3 were previously found to yield peak lung transfection (Wheeler, C. J., et al., Proc Natl Acad Sci USA 93:11454–11459 (1996); Sawa, T., et al., Hum. Gene Ther. 7:933–941 (1996)). The results are shown in FIG. 8. The level of luciferase expression in lung when the plasmid/lipid mixture was delivered to the lung in water (0.94 ng lux/lung) is comparable with published reports (Wheeler, C. J., et al., Proc Natl Acad Sci USA 93:11454–11459 (1996)) and is considerably below the level of expression obtained in muscle tissue using the same vectors without lipid. Unlike with muscle, when the plasmid/lipid mixture was delivered to the lung in a 150 mM sodium phosphate solution, luciferase expression was inhibited compared with water (0.22 vs. 0.94 ng lux/lung; p<0.001). However, when the plasmid/lipid mixture was delivered to the lung in a 2.5 mM sodium phosphate solution, luciferase expression was enhanced by 5.5-fold compared with water (5.2 vs. 0.94 ng lux/lung; p<0.001). Intermediate to these values, when the plasmid/lipid mixture was delivered to the lung in a 10 mM sodium phosphate solution, luciferase expression was enhanced compared with water, but not as much as with 2.5 mM sodium phosphate. When the plasmid/lipid mixture was delivered to the lung in saline, luciferase expression was inhibited compared with water (0.14 ng lux/lung, FIG. 8). Thus, sodium phosphate enhances luciferase expression upon delivery of a plasmid DNA/lipid mixture in lung, but does so at a much lower sodium phosphate molar concentration than is effective in muscle.

Example 9

Expression of Firefly Luciferase Following Intramuscular Injection of Plasmid DNA is Enhanced when the Plasmid is Injected in a Saline Solution with an Auxiliary Agent The effect of selected auxiliary agents on the level of luciferase expression from injected plasmid DNA in murine muscles was tested as follows. Plasmid DNA encoding firefly luciferase (VR1255) was injected into mouse quadriceps muscle as 50 μg DNA dissolved in 50 μl of saline (154 mM sodium chloride) alone or 150 mM sodium phosphate solution alone, or either one of the aqueous solutions containing 0.01% (v/v) NONIDET NP-40 (Ameresco) or 0.01% (v/v) Triton X-100™. Muscles (n=10 per group) were collected 7 days later and extracted and assayed for luciferase enzyme activity. The averaged data are shown in FIG. 9. Luciferase expression was increased when an auxiliary agent was added to either aqueous solution. The addition of 0.01% NONIDET NP-40 or 0.01% Triton X-100™ in 154 mM sodium chloride increased luciferase expression up to three-fold and six-fold respectively. Similarly, luciferase expression was significantly enhanced three-fold when DNA encoding luciferase plus either the auxiliary agent 0.01% NONIDET NP-40 or 0.01% Triton X-100™ was added in 150 mM sodium phosphate. Most importantly, the combination of changing the aqueous solution from 154 mM sodium chloride to 150 mM sodium phosphate plus an auxiliary agent (Triton X-100™) led to a 10 fold increase in luciferase expression.

Example 10

Expression of Firefly Luciferase Following Intramuscular Injection of Plasmid DNA is Enhanced when the Plasmid is Injected in a Sodium Phosphate Solution with an Auxiliary Agent The effect of selected auxiliary agents on the level of luciferase expression from injected plasmid DNA in murine muscles was tested as follows. Plasmid DNA encoding firefly luciferase (VR1255) was injected into mouse quadriceps muscle as 50 $\mu$g DNA dissolved in 50 $\mu$l of 150 mM sodium phosphate either alone, or with one of the auxiliary agents listed in Table V and VI, at various concentrations. Muscles (n=10 per group, total 560 muscles) were collected 7 days later and extracted and assayed for luciferase enzyme activity. The results are shown in FIG. 10 and Table V and VI.

Adding certain auxiliary agents into the 150 mM sodium phosphate solution enhanced luciferase expression, compared to expression obtained with 150 mM sodium phosphate alone. The averaged data are shown in Table V and VI. In most instances, luciferase expression was increased at least two-fold when an auxiliary agent was added to the 150 mM sodium phosphate solution.

For example, adding 0.01% (v/v) NP-40® or TritonX-100™ (0.01%) in the 150 mM sodium phosphate solution increased expression approximately 3-fold over expression in 150 mM sodium phosphate solution alone (p<0.05). Adding the Pluronic® F68, F108, P65, P103, P104, P105, L31, L44, L61, L62, L64, L81, L92, L101, L121, R 17R4, R 25R4 or R 25R2 into the sodium phosphate solution all significantly increased luciferase expression greater than 3-fold over expression in the sodium phosphate solution alone (p<0.05). It is worth noting that adding Pluronic® R 25R2 increased the expression by as much as 7-fold. Various other auxiliary agents such as DMSO, EDTA, IGEPAL CA 630®, Nonidet P40, SDS, Stachyose, Triton X-114®, Tween-20® and Tween-80® also significantly increased expression.

Example 11

Expression of Human Placental Alkaline Phosphatase Following Intramuscular Injection of Plasmid DNA is Enhanced when the Plasmid is Injected in a Sodium Phosphate Solution with an Auxiliary Agent Plasmid DNA (50 $\mu$g of DNA given in three doses on 3 consecutive days) encoding a secreted form of human placental alkaline phosphatase (SEAP; VR3301) was injected into mouse muscle in 50 $\mu$l 150 mM sodium phosphate solution either alone or with added 2% (w/v) Pluronic® F68 or 0.01% (v/v) Triton X-100™. The mice were monitored for blood levels of SEAP at day 7 post-injection. The results are shown in FIG. 11. Plasmid DNA was injected into the tibialis anterior muscles, and nude mice were used to prevent an immune response to the foreign transgene product. The addition of auxiliary agents to the 150 mM sodium phosphate solution significantly enhanced SEAP expression by 2-fold for Pluronic® F68 and 1.7-fold for Triton X-100™ compared with sodium phosphate alone (n=5; p<0.01 for Pluronic® F68 and p<0.02 for Triton X-100™). Thus, injection of plasmid DNA dissolved in a 150 mM sodium phosphate solution with certain auxiliary agents resulted in significantly higher levels of expression of SEAP than when dissolved in sodium phosphate alone.

The mice were also monitored over time for long-term expression of SEAP. The results are shown in FIG. 12. The kinetics of blood SEAP levels from mice injected with DNA dissolved in both 150 mM sodium phosphate alone and with the added auxiliary agents were similar. SEAP protein expression rose to a peak level at 7 days, then declined to 4% of the maximum expression level by day 35. However, auxiliary agents significantly enhanced SEAP expression by day 35 to 2-fold compared with 150 mM sodium phosphate alone (p<0.02 for Pluronic® F68 and p<0.04 for Triton X-100™) over the time course. Thus, injection of plasmid DNA dissolved in a 150 mM sodium phosphate solution with certain auxiliary agents resulted in higher levels of sustained expression of SEAP than when dissolved in sodium phosphate alone.

Example 12

Serum Hematocrit Levels Following Intramuscular Injection of Plasmid DNA Encoding Murine Erythropoietin is Enhanced when the Plasmid is Injected in a Sodium Phosphate Solution with an Auxiliary Agent Plasmid DNA (5 $\mu$g) encoding mouse erythropoietin (EPO; VR2901) or negative control plasmid DNA encoding canine blood clotting factor IX (VR1902) was injected into quadriceps muscles of immunocompetent mice in 50 $\mu$l 150 mM sodium phosphate solution either alone or with added 0.01% (v/v) NONIDET NP-40® (Ameresco). The mice were monitored over time for serum hematocrit levels, which correlate with the expression of erythropoietin. The results are shown in FIG. 13. Hematocrit levels rose steadily over for at least 21 days and remained at peak levels out to day 56 in the mice injected with VR2901. Control mice injected with VR1902 exhibited a constant hematocrit averaging 48. Injection of plasmid DNA dissolved in 150 mM sodium phosphate solution with 0.01% NONIDET NP-40® resulted in higher hematocrit levels than the injection of plasmid DNA dissolved in 150 mM sodium phosphate solution alone at all the time points tested, (p=0.05% with auxilary agent, a 10% rise in hematocrit seen after day 14). Thus, injection of plasmid DNA dissolved in a 150 mM sodium phosphate solution with an auxiliary agent resulted in a higher level of sustained expression of EPO than when dissolved in sodium phosphate alone.

Example 13

Equivalent or Elevated Serum Hematocrit Levels Following Intramuscular Injection of Plasmid DNA Encoding Murine Erythropoietin are Achieved with Less Plasmid DNA when the Plasmid is Injected in a Sodium Phosphate Solution as Opposed to Saline Plasmid DNA encoding mouse erythropoietin (EPO; VR2901) or negative control plasmid DNA encoding canine blood clotting factor IX (VR1902) was injected into quadriceps muscles of five groups of immunocompetent mice in 50 μl of either 150 mM sodium phosphate solution or saline. Group 1 mice received 10 μg of VR2901 dissolved in 150 mM sodium phosphate, group 2 received 2.5 μg VR2901 dissolved in 150 mM sodium phosphate, group 3 received 10 μg VR2901 dissolved in saline, group 4 received 2.5 μg VR2901 dissolved in saline, and group 5 received 10 μg VR1902 dissolved in 150 mM sodium phosphate. The mice were monitored over four weeks for serum hematocrit levels, which correlate with the expression of erythropoeitin. The results are shown in FIG. 14. Hematocrit levels rose steadily for at least 21 days and remained at peak levels up to four weeks in the mice injected with VR2901. Control mice injected with VR1902 exhibited a constant hematocrit averaging 48. Injection of both concentrations of plasmid DNA dissolved in 150 mM sodium phosphate solution resulted in higher hematocrit levels than the injection of either concentration of plasmid DNA dissolved in saline. This demonstrates that when injections are done in 150 mM sodium phosphate solution, one can use four-times less the amount of DNA than injections done in saline, and get a an equivalent or better increase of hematocrit. Thus, injections of plasmid DNA dissolved in a 150 mM sodium phosphate solution allow for a considerable reduction in the amount of plasmid DNA required to achieve a therapeutic response.

Example 14

Equivalent or Improved Expression of Human Placental Alkaline Phosphatase Following Intramuscular Injection of Plasmid DNA is Achieved with Lower Plasmid Dosages when the Plasmid is Injected in a Sodium Phosphate Solution with an Auxiliary Agent Plasmid DNA (100 μg or 300 μg) encoding a secreted form of human placental alkaline phosphatase (SEAP; VR3301) was injected into mouse muscle in 50 μl 150 mM sodium phosphate solution either alone or with added 2% (w/v) Pluronic® F68 or 0.01% (v/v) Triton X-100™. The mice were monitored for blood levels of SEAP at day 7 post-injection. The results are shown in FIG. 15. Plasmid DNA was injected into the tibialis anterior muscles, and nude mice were used to prevent an immune response to the foreign transgene product. The levels of SEAP expression achieved with the 100 μg dosage of plasmid DNA with 0.01% Triton X100™ was nearly equivalent to the level of SEAP expression achieved with the 300 μg dosage of plasmid DNA in 150 mM sodium phosphate alone, and the level of SEAP expression achieved with the 100 μg dosage of plasmid DNA with Pluronic® F68 was equivalent to the level of SEAP expression achieved with the 300 μg dosage of plasmid DNA in 150 mM sodium phosphate alone. Thus, injection of plasmid DNA dissolved in a 150 mM sodium phosphate solution with certain auxiliary agents allows the amount of DNA in the dosage to be significantly reduced, e.g., threefold in this example.

Example 15

Plasmid DNA Immunization Utilizing Sodium Phosphate Solutions Containing Certain Auxiliary Agents The effect of sodium phosphate solution containing certain auxiliary agents on the elicitation of an immune response upon injection of pDNA encoding an immunogen was examined as follows. Mice were treated bilaterally in the quadriceps muscles with 5 μg of plasmid VR1412 (10 μg total DNA), encoding β-galactosidase, which was dissolved in 50 μl of 150 mM sodium phosphate solution or 150 mM sodium phosphate solution containing 0.01% (v/v) Triton X-100™, 4% (w/v) Pluronic® F68, or 0.5% (w/v) Pluronic® P65. Another group of five mice were treated with 50 μg total plasmid VR1412, in 150 mM sodium phosphate alone. The results are shown in FIG. 16A (titer at two weeks), 16B (titer at four weeks), and 16C (titer at ten weeks). At two weeks, anti-β-galactosidase antibody was detected in four of the five mice vaccinated with 10 μg VR1412 in 150 mM phosphate buffer+0.5% Pluronic® P65. In fact, the levels of antibody detected with 10 μg of VR1412 in 150 mM phosphate buffer+0.5% Pluronic® P65 were similar to levels seen with 50 μg of VR-1412 without an auxiliary agent in 150 mM phosphate buffer. In addition, at two weeks, one of the five mice vaccinated with 10 μg VR1412 in 150 mM sodium phosphate+4% Pluronic® F68 showed anti-β-galactosidase antibody. At four weeks, anti-β-galactosidase antibody was detected in five of the five mice vaccinated with VR1412 in 150 mM phosphate buffer+0.5% Pluronic® P65. Also, at four weeks two of the five mice vaccinated with VR-1412 in 150 mM sodium phosphate+4% Pluronic® F68 showed anti-β-galactosidase antibody and three of the five mice vaccinated with VR-1412 in 150 mM sodium phosphate buffer+0.01% Triton X-100™ were positive for anti-β-galactosidase antibody. At ten weeks, anti-β-galactosidase antibody was detected in five of the five mice vaccinated with VR1412 in 150 mM phosphate buffer+0.5% Pluronic® P65. Also, at 10 weeks three of the five mice vaccinated with VR-1412 in 150 mM sodium phosphate+4% Pluronic® F68 showed anti-β-galactosidase antibody and four of the five mice vaccinated with VR-1412 in 150 mM sodium phosphate buffer+0.01% Triton X-100™ were positive for anti-β-galactosidase antibody. In contrast, none of the mice vaccinated with 10 μg VR1412 in 150 mM sodium phosphate solution not containing an auxiliary agent showed anti-β-galactosidase antibody, either at the two week or four week time point. These results demonstrate that the amount of DNA necessary to produce an antibody response is significantly reduced by delivery of the polynucleotide in 150 mM sodium phosphate plus an auxiliary agent.

FIG. 16D shows that the addition of an auxiliary agent such as Pluronic® F68 (4%) or Pluronic® P65 (0.5%) has no effect on the cytotoxic T cell lysis (CTL). BALB/c mice (n=5) were vaccinated bilaterally in the rectus femoris muscles with 5 μg of VR1412 (10 μg total DNA), which was dissolved in 50 μl of 150 mM Na phosphate solution containing either no auxiliary agent, 4% Pluronic® F68 or 0.5% Pluronic® P65. Mice were vaccinated on day 0 then boosted on day 20. Seven weeks following the initial immunization, cytotoxic T cell activity was determined. There was no significant difference in cytotoxic T cell activity among the groups vaccinated. Thus, mice vaccinated with a DNA solution of 150 mM Na phosphate alone or containing the auxiliary agent Pluronic® F68 (4%) or Pluronic® P65 (0.5%) demonstrated an equivalent amount of cytotoxic T cell activity.

Example 16

Serum Hematocrit Levels in Domestic Cats Following Intramuscular Injection of Plasmid DNA Encoding Feline Erythropoietin is Enhanced when the Plasmid is Injected in a Sodium Phosphate Solution with an Auxiliary Agent Plasmid DNA encoding feline erythropoietin (fEpo; VR2921) was prepared by insertion of the coding region for Epo into plasmid VR1012 by standard methods. The plasmid was delivered intramuscularly to four groups of cats in 2 ml of 150 mM sodium phosphate solution either alone (group 1, 5 mg/ml DNA, n=4; group 2, 3 mg/ml DNA, n=3; or group 3, 1 mg/ml DNA, n=5) or with added 0.01% (v/v) Triton X-100™ (group 4, 1 mg/ml DNA, n=4). Two milliliters of DNA were delivered as 1-ml injections into each rectus femoris muscle. Following injection, cats were monitored at 7 day intervals for serum hematocrit levels, which correlate with the expression of erythropoietin. Hematocrit levels were elevated in 3 of 4 cats in group 4 and remained elevated for periods in excess of 40 days. No cats in groups 1 and 2 exhibited elevated hematocrits, and one cat in group 3 exhibited a borderline elevation of hematocrit. Thus, injection of plasmid DNA dissolved in 150 mM sodium phosphate solution with added 0.01% (v/v) Triton X-100™ resulted in a greatly improved hematocrit response compared to the injection of plasmid DNA dissolved in 150 mM sodium phosphate solution alone, even though the group 4 cats received only one fifth the DNA given to the cats in group 1, and only one third the DNA given to the cats in group 2.

Example 17

Anti-tumor Effect of Systemic mIFN-α pDNA Treatment is Enhanced when the Plasmid is Administered in a Sodium Phosphate Solution Female C57BL/6 mice, 6–8 weeks, were injected subcutaneously with $10^4$ B16F10 tumor cells as described (Horton, H. M. et al., Proc. Natl. Acad. Sci. USA 96:1553–1558 (1999)). Four days later, the mice were injected i.m. with 100 µg (50 µg DNA/50 µl per muscle) of either VR4111 (mIFN-α pDNA) or VR1055 (control plasmid DNA) into the rectus femoris. The mouse IFN-α gene was a generous gift from Paula Pitha-Rowe (Johns Hopkins University). The IFN-α gene was subcloned into the VR1055 vector as described (Horton et al., 1999). The VR4111 was delivered in either saline, PBS or 150 mM sodium phosphate (pH 7.0). The VR1055 was delivered in saline. The i.m. injections were administered twice per week for 3 weeks. Beginning on day 11 after the tumor cell injection, the subcutaneous tumors were measured 3 times per week using calipers (length×width×height) and tumor volume was calculated using the formula: tumor volume ($mm^3$)=0.52 (length×width×height). Each treatment group consisted of 10 mice. Mouse survival was analyzed using a Kaplan-Meier survival plot followed by a Logrank (Mantel-Cox) test to identify significant differences in survival between groups. Differences were considered statistically significant when the p value was less than 0.05.

Tumor growth and survival were monitored for 35 days. The median tumor volumes for the groups containing at least 7 mice are shown in FIG. 17A. FIG. 17A shows that mice injected with IFN-α plasmid DNA in the 150 mM sodium phosphate solution had a lower rate of tumor growth compared with the blank DNA treated controls at all time points up to 22 days ($p \leq 0.001$). At the time points after considerable tumor growth (i.e., after 22 days), average tumor sizes in the 150 mM sodium phosphate group were 2- to 3-fold smaller than those from the saline or PBS groups. However, sodium phosphate+DNA only showed a statistically lower tumor volume than saline DNA at the last saline time point (27 days) (955 vs. 2069 $mm^3$; n=9; p=0.03). The PBS and sodium phosphate groups were not significantly different from one another at the other points after 27 days (n=9–10; p=0.07 to 0.17).

The mouse survival results from the same IFN-α DNA induced anti-tumor study are shown in FIG. 17B. In the control blank DNA injected group, no mice survived beyond day 25, whereas 2 out of 10 mice survived to day 38 in the saline groups and 4 out of 10 mice survived to day 41 in the PBS and 150 mM sodium phosphate groups. All three of the VR4111 DNA treated groups (saline, PBS and 150 mM sodium phosphate) showed a statistically significant survival difference compared with the blank DNA in saline treated group (p<0.007, Kaplan-Meier test, n=9–10). The PBS and 150 mM sodium phosphate groups appeared to yield a higher % survival than the saline group. It is expected that the use of an auxiliary agent (e.g., 0.01% Pluronic® L64, 0.01% Triton X-100™, or Pluronic® R 25R2) would further reduce tumor burden if combined with the sodium phosphate salt in the vehicle.

Example 18

Serum Hematocrit Levels in Domestic Dogs Following Intramuscular Injection of Plasmid DNA Encoding Canine Erythropoietin is Enhanced when the Plasmid is Injected in a Sodium Phosphate Solution with an Auxiliary Agent Plasmid DNA encoding canine erythropoietin (cEpo; VR2920) was prepared by insertion of the coding region for cEpo into plasmid VR1012 by standard methods. The plasmid was delivered intramuscularly to two groups of dogs in 10 ml of 150 mM sodium phosphate solution either alone (group 1, 20 mg/ml DNA, n=6) or with added 0.001% (v/v) Triton X-100™ (group 2, 20 mg/ml DNA, n=6). Ten milliliters of DNA were delivered as 5-ml injections into each of the rectus femoris muscle. The dogs were monitored at seven day intervals for serum hematocrit levels, which correlate with the expression of erythropoietin. Hematocrit levels were elevated in 5 of 6 dogs in group 2. Conversely, hematocrit levels were elevated in only 2 of 6 dogs in group 1. Thus, injection of plasmid DNA dissolved in 150 mM sodium phosphate solution with added 0.001% (v/v) Triton X-100™ resulted in a greatly improved hematocrit response than the injection of plasmid DNA dissolved in 150 mM sodium phosphate solution alone.

Example 19

Prevention or Treatment of Malaria in Humans Utilizing Intramuscular Injection of Plasmid DNA Encoding a Malarial Antigen in a Sodium Phosphate Solution with an Auxiliary Agent In order to prevent or treat malaria in humans, a composition comprising plasmid DNA encoding a Plasmodium falciparum circumsporozoite protein (PfCSP) is prepared according to standard methods. Human subjects are injected three times with 0.1, 0.5, 1.0, 2.5, or 5.0 mg of the plasmid DNA dissolved in an aqueous solution of about 150 mM sodium phosphate and about 4.0% (w/v) Pluronic® F68 at 4-week intervals in alternate deltoids. Serum is removed from the subjects and the Plasmodium falciparum antibody levels are determined by serial dilution using a standard ELISA assay. Immune responses of human subjects to the antibody are induced, as indicated by normalized GMT values.

Example 20

Prevention of Influenza in Humans Utilizing Intramuscular Injection of Plasmid DNA Encoding an Influenza-A virus Antigen in a Sodium Phosphate Solution with an Auxiliary Agent To prevent influenza virus infection in humans, a composition comprising plasmid DNA encoding an influenza A virus hemagglutinin (HA) is prepared according to standard methods. Subjects are injected three times with 0.1, 0.5, 1.0, 2.5, or 5.0 mg of the plasmid DNA dissolved in an aqueous solution of about 150 mM sodium phosphate and about 4.0% (w/v) Pluronic® F68 at 4-week intervals in alternate deltoids. Serum is removed from the humans and antibody levels to the influenza antigen is determined by serial dilution using a standard ELISA assay. Immune responses of the human subjects to HA antigen are induced with significantly lowered dosages of DNA, as indicated by normalized GMT values.

Example 21

Treatment Regimen with Human Interferon-omega to Treat Human Patients with Chronic Hepatitis B or C Utilizing Intramuscular Injection of Plasmid DNA in a Sodium Phosphate Solution with an Auxiliary Agent The effect of a sodium phosphate solution containing an auxiliary agent on the expression of a therapeutic polypeptide in humans following intramuscular injection of plasmid DNA encoding the polypeptides is examined as follows. To decrease the chronic infection of Hepatitis B and C, about 1–50 mg, preferably about 10–30 mg of a plasmid encoding human interferon-omega (IFN-ω); VR4151) dissolved in an aqueous solution of about 150 mM sodium phosphate and about 4.0% (w/v) Pluronic® F68 is injected intramuscularly into a human patient biweekly or monthly. At appropriate time points post-injection, serum from the patient is assayed for circulating levels of IFN-ω, which are detectable at lower dosages than might be required if the plasmid DNA is dissolved in water or saline. The therapy regimen is continued for a minimum of 24 weeks during which time the patients are monitored for, for example, levels of serum alanine aminotransferase and clearance of hepatitis C virus (HCV) RNA in HCV patients, and serum HBsAg and HBV DNA in HBV patients. Liver biopsies are performed at the end of the treatment period. A successful outcome of the therapy in a HBV or HCV patient is indicated, for example, by a normalization of serum alanine aminotransferase levels, a decrease in serum levels of HBsAg, a disappearance or decrease in detectable virus in the patient's serum, and histological improvement in the liver. In some cases, this therapy is used in conjunction with anti-virals such as lamivudine for HBV and ribavirin for HCV.

Example 22

Figure 19B:
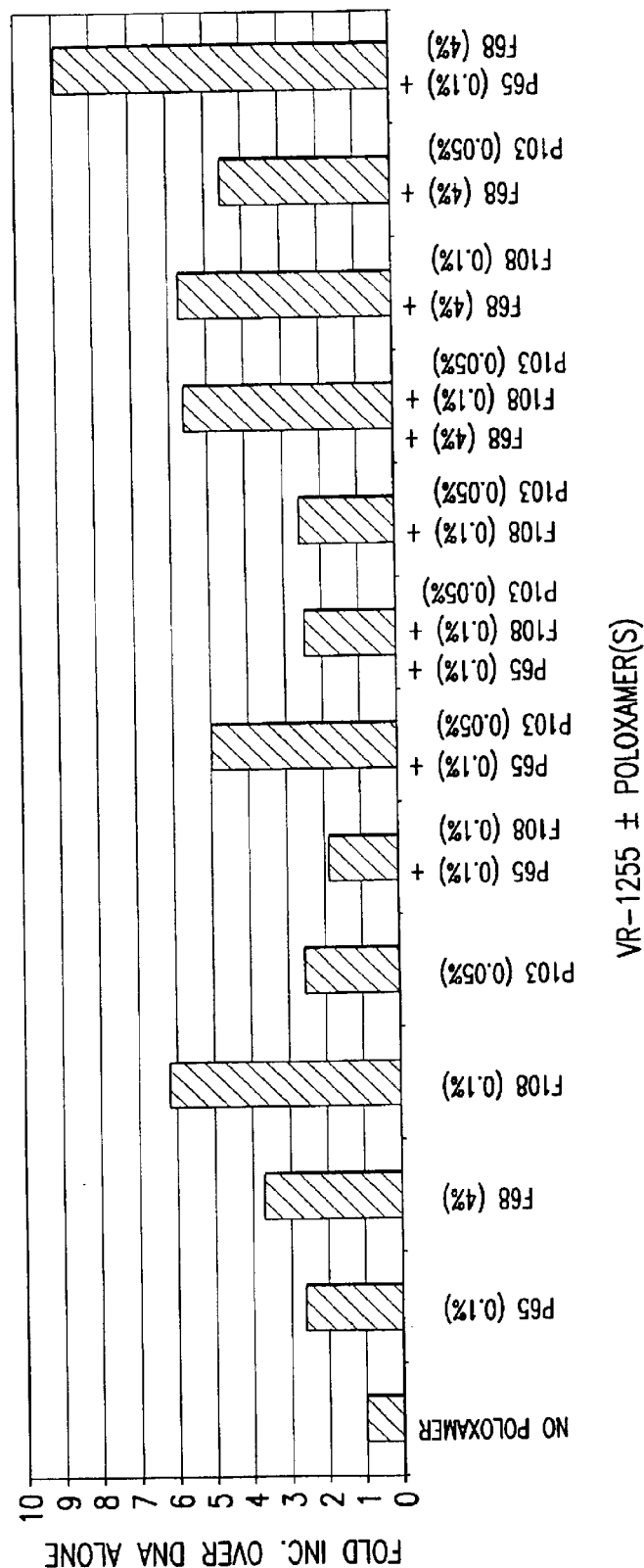

Expression of Firefly Luciferase Following Intramuscular Injection of Plasmid DNA is Enhanced when the Plasmid is Injected in a Sodium Phosphate Solution with a Combination of Two or More Auxiliary Agents Plasmid DNA encoding firefly luciferase (VR1255) was injected into mouse quadriceps muscle as 50 µg DNA dissolved in 50 µl of 150 mM sodium phosphate either alone, containing a single auxiliary agent, or containing a combination of two or more auxiliary agents. A total of 127 muscles (n=8–10 per experiment) were collected 7 days later and extracted and assayed for luciferase enzyme activity. The results are shown in FIG. 19 and Table IV.

Certain auxiliary agent combinations enhanced luciferase expression over that observed with 150 mM sodium phosphate alone or with 150 mM sodium phosphate plus a single auxiliary agent. For example, the combination of 0.10% (w/v) Pluronic® P65 and 4.0% (w/v) Pluronic® F68 in 150 mM sodium phosphate solution increased expression by 8.93 fold over expression with 150 mM sodium phosphate solution alone (p=0.02) and at least 2-fold over expression with either of the two auxiliary agents alone in 150 mM sodium phosphate solution.

Example 23

Effect of Alternate Salt Solutions on Luciferase Plasmid DNA Expression in Murine Muscles In this example, injection of plasmid DNA encoding luciferase dissolved in 150 mM solutions of various salts which vary either the cation or the anion of normal saline were compared with saline for their ability to stimulate luciferase expression in murine muscle. The results are shown in FIG. 18.

Plasmid VR1255 dissolved in the various solutions was tested for day 7 expression in quadriceps muscle as described in Example 1 above. As shown in FIG. 18, injection of the plasmid DNA in solutions of the sodium salts of phosphate, acetate, bicarbonate or sulfate all significantly increased luciferase expression compared with saline or potassium chloride. Similarly, injection of the plasmid DNA in solutions of the potassium salts of phosphate, acetate, or bicarbonate all increased luciferase expression compared with saline or potassium chloride, with potassium phosphate showing a significant increase. In addition injection of the plasmid DNA in 150 mM disodium salt solutions of glycerophosphate and glucose-6-phosphate both increased luciferase expression compared with either saline or potassium chloride, with disodium glycerophosphate showing a significant increase. Thus, various 150 mM salt solutions exhibit stimulatory effects on luciferase expression in the mouse quadriceps model.

Example 24

Expression of Firefly Luciferase in Rats Following Intramuscular Injection of Plasmid DNA Encoding Firefly Luciferase is Enhanced when the Plasmid is Injected in a Sodium Phosphate Solution with an Auxiliary Agent Plasmid DNA encoding firefly luciferase (VR1255) was injected into rat quadriceps muscle as 10 µg DNA dissolved in 150 mM sodium phosphate solution either alone (1 µg/µl DNA, n=8) or with added 4.0% (w/v) Pluronic® F68 (1 µg/µl DNA, n=8). Rat muscles were collected 3 days later and processed to determine the level of expression. For this, each muscle was first frozen and cut into ten sections (approximately 2 mm thick each). Each section was then extracted and assayed for luciferase activity. As shown in FIG. 20A, adding Pluronic® F68 enhanced luciferase expression by 5-fold over that observed with 150 mM sodium phosphate alone (p=0.003).

Plasmid DNA encoding firefly luciferase (VR1255) was injected into rat quadriceps muscle as 50 µg DNA dissolved in PBS (1 µg/µl DNA, n=8), or in 150 mM sodium phosphate solution either alone (1 µg/µl DNA, n=8) or with added 0.01% (w/v) Pluronic® R 25R2 (1 µg/µl DNA, n=8). Rat muscles were collected 3 days later and processed to determine the level of expression. For this, each muscle was first frozen and cut into ten sections (approximately 2 mm thick each). Each section was then extracted and assayed for luciferase activity. As shown in FIG. 20B, sodium phosphate alone enhanced expression about 2-fold over PBS, and adding Pluronic® R 25R2 to sodium phosphate enhanced luciferase expression by about 3-fold over that observed with 150 mM sodium phosphate alone. There was a significant increase in luciferase expression in the rat quadriceps muscles when the plasmid DNA was delivered in 150 mM sodium phosphate alone versus PBS alone (p=0.029), and when plasmid DNA was delivered in 150 mM sodium phosphate plus 0.01% (w/v) Pluronic® R 25R2 versus PBS (p=0.029).

Example 25

Serum Hematocrit Levels Following Intramuscular Injection of Plasmid DNA Encoding Murine Erythropoietin is Enhanced when the Plasmid is Injected with a Poloxanmer Plasmid DNA (1 µg) encoding mouse erythropoietin (EPO; VR2901) or negative control plasmid DNA encoding canine blood clotting factor IX (VR1902) was injected into quadriceps muscles of immunocompetent BALB/c mice in saline or 50 µl 150 mM sodium phosphate solution either alone or with added 0.01% (w/v) Pluronic® R 25R2. The mice were monitored at days 0, 7, 14, 21, and 28 for serum hematocrit levels, which correlate with the expression of erythropoeitin. The results are shown in FIG. 21. Control mice injected with VR 1902 exhibited a constant hematocrit level, averaging 48%. Mice injected with plasmid DNA dissolved in saline with 0.01% Pluronic® R 25R2 resulted in significantly higher hematocrit levels than those injected with plasmid DNA dissolved in saline alone on days 21 and 28 ($p<0.05$). Mice injected with plasmid DNA dissolved in 150 mM sodium phosphate with 0.01% Pluronic® R 25R2 resulted in significantly higher hematocrit levels than those injected with plasmid DNA dissolved in 150 mM sodium phosphate alone on day 14 ($p<0.05$). The highest hematocrit levels were seen in mice injected with plasmid DNA dissolved in 150 mM sodium phosphate with 0.01% Pluronic® R 25R2 at days 14, 21, and 28. Furthermore, hematocrit levels increased significantly over time when plasmid was injected either in 150 mM sodium phosphate solution alone, or in 150 mM sodium phosphate solution with 0.01% Pluronic® R 25R2. Thus, injection of a single 1 µdose of plasmid DNA dissolved in a saline or 150-mM sodium phosphate solution with Pluronic® R 25R2 resulted in a higher hematocrit level than when dissolved in saline or sodium phosphate alone, with sodium phosphate, alone or with Pluronic® R 25R2 showing significant enhancement at 14, 21, and 28.

Plasmid DNA (10 µg) encoding mouse erythropoietin (EPO; VR2996) was injected into quadriceps muscles of immunocompetent BALB/c mice in 50 µl 150 mM sodium phosphate solution either alone or with added 4% (w/v) Pluronic® F68. The mice were monitored at days 7, 14, and 28 for serum hematocrit levels, which correlate with the expression of erythropoietin. Control serum levels were measured before any injections. The results are shown in FIG. 22. Mice injected with plasmid DNA dissolved in 150 mM sodium phosphate solution with 4% Pluronic® F68 resulted in significantly higher hematocrit levels than those injected with plasmid DNA dissolved in 150 mM sodium phosphate solution alone on days 7, 14, and 30. Thus, injection of plasmid DNA dissolved in a 150-mM sodium phosphate solution with Pluronic® F68 resulted in a higher hematocrit level than when dissolved in sodium phosphate alone.

Example 26

Expression of Firefly Luciferase Following Intramuscular Injection of Plasmid DNA is Enhanced When the Plasmid is Injected in a Sodium Phosphate Solution with 0.01% Pluronic® R 25R2

BALB/c mice (n=5, i.e., 10 muscles) were injected on day 0 with varying doses of pLUX (VR1255) in 50 microliters of a 150 mM sodium phosphate solution with or without Pluronic® R 25R2 (0.01%). Muscles were harvested on day 7 and assayed for luciferase activity. As showin in FIG. 23, there was a significant enhancement of luciferase activity when mice were injected with VR1255+0.01% Pluronic® R 25R2 compared to VR1255 alone ($p<0.05$). This enhancement was seen in all DNA doses tested.

BALB/c mice (n=5, i.e., 10 muscles) were injected on day 0 with 50 micrograms of pLUX (VR1255) in 50 microliters of a 150 mM sodium phosphate solution with or without Pluronic® R 25R2 (0.01%). Muscles were harvested on days 1, 3, 7, 10 and 28 and assayed for luciferase activity. As shown in FIG. 24, there was a significant enhancement of luciferase activity when mice were injected with VR1255+ 0.01% Pluronic® R 25R2 compared to VR1255 alone on days 1, 7, and 10 ($p<0.05$).

Example 27

Transfection of Muscle Fibers Following Intramuscular Injection of Plasmid DNA is Enhanced when the Plasmid is Injected in a Sodium Phosphate Solution with 0.01% Pluronic® R 25R2

BALB/c mice were injected in the rectus femoris with 50 µg of VR1412 (β-galactosidase) in 50 µl of normal saline or 150 mM sodium phosphate solution, each either alone, or with with 0.01% Pluronic® R 25R2. Whole quadriceps muscle groups were harvested on day 7. Muscles were snap frozen in OTC medium (n=10 muscles for each group). 10 micron cross-sections were stained with x-gal (substrate for β-gal). Fibers expressing β-gal (stained blue) were counted. The percentage of muscle fibers positive for β-gal expression are shown in FIG. 25, and a comparison of average muscle sections injected with plasmid DNA in saline and plasmid DNA in sodium phosphate solution plus 0.01% Pluronic® R 25R2 are shown in FIG. 26. These results show that 0.01% Pluronic® R 25R2 can increase the number of muscle cells transfected whether it is in saline or 150 mM sodium phosphate solution. However, the highest number of transfected cells were obtained with the combination of Pluronic® R 25R2, 0.01% in 150 mM sodium phosphate.

All publications cited in this specification are hereby incorporated herein by reference. While the invention has been described with reference to a particularly preferred embodiment, it will be appreciated that modifications can be made without departing from the spirit of the invention. Such modifications are intended to fall within the scope of the appended claims.

TABLE I

Effects of Selected Sodium Chloride Vehicles on Luciferase Plasmid DNA expression in Muscle

| ng Lux per Muscle | ± Std. Error | n | Fold Saline | Salt Solution |
|---|---|---|---|---|
| 4 | 1 | 30 | 0.03 | Double-distilled water |
| 119 | 6 | 413 | 1.0 | 150 mM Sodium Chloride (saline) |
| 186 | 11 | 357 | 1.6 | 150 mM Sodium Chloride (saline) + 10 mM Sodum Phosphate (PBS) |
| 117 | 64 | 20 | 1.0 | 150 mM Sodum Chloride (saline) + 100 mM Sodium Phosphate |
| 112 | 38 | 20 | 0.9 | 100 mM Sodium Chloride |

TABLE I-continued

Effects of Selected Sodium Chloride Vehicles on Luciferase Plasmid DNA expression in Muscle

| ng Lux per Muscle | ± Std. Error | n | Fold Saline | Salt Solution |
|---|---|---|---|---|
| 203 | 42 | 40 | 1.7 | 100 mM Sodium Chloride + 50 mM Sodium Phosphate |

TABLE II

Effects of Selected Vehicles on Luciferase Plasmid DNA expression in Muscle

| ng Lux/ Muscle | ± Std. Error | n | Fold Saline | Salt Solution | Formula |
|---|---|---|---|---|---|
| A. Chloride Salts at 150 mM | | | | | |
| 119 | 6 | 413 | 1.0 | Sodium Chloride | NaCl |
| 124 | 32 | 10 | 1.0 | Potassium Chloride | KCl |
| 1 | 0.4 | 10 | <0.1 | Magnesium Chloride | $MgCl_2 \cdot 6H_2O$ |
| 0.3 | 0.2 | 10 | <0.1 | Calcium Chloride | $CaCl_2 \cdot 2H_2O$ |
| 0.1 | 0.1 | 6 | <0.1 | Zinc Chloride | $ZnCl_2$ |
| 0.0 | 0.0 | 4 | <0.1 | Ferrous Chloride | $FeCl_2 \cdot 4H_2O$ |
| B. Phosphate salts at 150 mM | | | | | |
| 481 | 36 | 120 | 4.0 | Sodium Phosphate | $NaH_2PO_4$/$Na_2HPO_4$ |
| 282 | 56 | 20 | 2.4 | Sodium dibasic | $Na_2HPO_4$ |
| 198 | 44 | 20 | 1.7 | Sodium monobasic | $NaH_2PO_4$ |
| 449 | 40 | 20 | 3.8 | Potassium Phosphate | $KH_2PO_4$/$K_2HPO_4$ |
| 22 | 6 | 8 | 0.2 | Magnesium Phosphate | $MgHPO_4 \cdot 3H_2O$ |
| 12 | 2 | 8 | 0.1 | Calcium Phosphate | $CaHPO_4$ |
| 4 | 1 | 8 | <0.1 | Aluminum Phosphate | $AlPO_4$ |
| 0.4 | 0 | 10 | <0.1 | Ferric Phosphate | $FePO_4$ |
| C. Sodium salts at 150 mM | | | | | |
| 119 | 6 | 413 | 1.0 | Sodium Chloride | NaCl |
| 481 | 36 | 120 | 4.0 | Sodium Phosphate | $NaH_2PO_4$/$Na_2HPO_4$ |
| 498 | 119 | 10 | 4.1 | Sodium Acetate | $C_2H_3O_2Na \cdot 3H_2O$ |
| 364 | 64 | 19 | 3.1 | Sodium Pyruvate | $C_3H_3O_3Na$ |
| 330 | 47 | 20 | 2.8 | Sodium Bicarbonate | $NaHCO_3$ |
| 312 | 83 | 10 | 2.6 | Sodium Sulfate | $Na_2SO_4$ |
| 90 | 25 | 14 | <0.1 | Sodium Citrate | $C_6H_5Na_3O \cdot 2H_2O$ |
| 15 | 2 | 8 | <0.1 | Sodium Oxalate | $C_2O_4Na_2$ |

TABLE III-A

| Salt | pH | lux |
|---|---|---|
| Zinc Chloride | 5.0 | 0.1 |
| Ferrous Chloride | 5.0 | 0.0 |
| Aluminum Phosphate | 5.0 | 4 |
| 150 mM NaCl (Saline) | 5.5 | 119 |
| 100 mM NaCl | 5.5 | 112 |
| Potassium Chloride | 5.5 | 124 |
| Magnesium Chloride | 5.5 | 1 |
| Calcium Chloride | 5.5 | 0.3 |
| Sodium Chloride | 5.5 | 119 |
| NaP - monobasic | 5.5 | 198 |
| Sodium Sulfate | 5.5 | 312 |
| Calcium Phosphate | 6.0 | 12 |
| Sodium Pyruvate | 6.0 | 364 |
| Ferric Phosphate | 6.5 | 0.4 |
| Sodium Acetate | 6.5 | 498 |
| Sodium Oxalate | 6.5 | 15 |
| Magnesium Phosphate | 7.0 | 22 |
| Saline + 10 mM Na—P (PBS) | 7.2 | 186 |
| 75 mM NaCl + 75 mM Na—P | 7.2 | 177 |
| 50 mM Sodium Phosphate | 7.2 | 254 |
| 100 mM Sodium Phosphate | 7.2 | 270 |
| 150 mM Sodium Phosphate | 7.2 | 481 |
| Sodium Phosphate | 7.2 | 481 |
| Potassium Phosphate | 7.5 | 449 |
| Sodium Citrate | 7.5 | 108 |
| 50 mM Sodium Citrate | 7.5 | 83 |
| NaP - dibasic | 8.0 | 282 |
| Sodium Pyrophosphate | 9.0 | 3 |
| Sodium Bicarbonate | 9.0 | 330 |

TABLE III-B

| Salt | Osm | lux |
|---|---|---|
| Calcium Phosphate | 36 | 12 |
| Aluminum Phosphate | 37 | 4 |
| Magnesium Phosphate | 39 | 22 |
| 50 mM Sodium Phosphate | 83 | 254 |
| 50 mM Sodium Citrate | 164 | 83 |
| Ferric Phosphate | 165 | 0.4 |
| 100 mM NaCl | 215 | 112 |
| 100 mM Sodium Phosphate | 232 | 270 |
| Sodium Acetate | 271 | 498 |
| Sodium Pyruvate | 271 | 364 |
| Sodium Bicarbonate | 727 | 330 |
| NaP - monobasic | 277 | 198 |
| Potassium Chloride | 280 | 124 |
| 150 mM NaCl + 10 mM Na—P | 292 | 186 |
| 75 mM NaCl + 75 mM Na—P | 308 | 177 |
| 150 mM Sodium Phosphate | 308 | 481 |
| 150 mM NaCl (Saline) | 310 | 119 |
| Potassium Phosphate | 323 | 449 |
| Sodium Oxalate | 346 | 15 |
| Sodium Sulfate | 349 | 312 |
| NaP - dibasic | 357 | 282 |
| Zinc Chloride | 358 | 0.1 |
| Magnesium Chloride | 360 | 1 |
| Calcium Chloride | 362 | 0.3 |
| Ferrous Chloride | 362 | 0.0 |
| Sodium Pyrophosphate | 363 | 3 |
| Sodium Citrate | 394 | 108 |

TABLE IV

| Added Auxiliary Agents | Average µg luciferase muscle | Fold inc. | P value over control |
|---|---|---|---|
| VR-1255 in 150 mM NaP (Control) | 0.37 | — | — |
| Pluronic ® P65 (0.1%) | 0.96 | 2.61 | 0.09 |
| Pluronic ® F68 (4%) | 1.37 | 3.70 | 0.03 |
| Pluronic ® F108 (0.1%) | 2.28 | 6.18 | 0.001 |
| Pluronic ® P103 (0.05%) | 0.94 | 2.55 | 0.07 |
| Pluronic ® P65 (0.1%), and Pluronic ® F108 (0.1%) | 0.69 | 1.88 | 0.25 |

TABLE IV-continued

| Added Auxiliary Agents | Average μg luciferase muscle | Fold inc. | P value over control |
|---|---|---|---|
| Pluronic ® P65 (0.1%), and Pluronic ® P103 (0.05%) | 1.84 | 4.97 | 0.01 |
| Pluronic ® P65 (0.1%), Pluronic ® F108 (0.1%), and Pluronic ® P103 (0.05%) | 0.91 | 2.46 | 0.09 |
| Pluronic ® F108 (0.1%), and Pluronic ® P103 (0.05%) | 0.95 | 2.57 | 0.06 |
| Pluronic ® F68 (4%), Pluronic ® F108 (0.1%), and Pluronic ® P103 (0.05%) | 2.08 | 5.62 | 0.10 |
| Pluronic ® F68 (4%), and Pluronic ® F108 (0.1%) | 2.11 | 5.72 | 0.10 |
| Pluronic ® F68 (4%), and Pluronic ® P103 (0.05%) | 1.69 | 4.58 | 0.04 |
| Pluronic ® P65 (0.1%), and Pluronic ® F68 (4%) | 3.30 | 8.93 | 0.02 |

TABLE V

| Poloxamers tested | Concentrations tested | Optimal Concentration | FOLD x NaP |
|---|---|---|---|
| Pluronic ® F68 | 0.8% to 4% | 4.00% | 5 |
| Pluronic ® F77 | 0.1% to 8.0% | 1.00% | 2 |
| Pluronic ® F108 | 0.10% | 0.10% | 6 |
| Pluronic ® F127 | 0.005% to 0.5% | 0.10% | 3 |
| Pluronic ® P65 | 0.01% to 1.00% | 0.50% | 4 |
| Pluronic ® P85 | 0.001% to 1.00% | 0.10% | 1 |
| Pluronic ® P103 | 0.01% to 1.00% | 0.05% | 3 |
| Pluronic ® P104 | 0.01% to 1.00% | 0.10% | 3 |
| Pluronic ® P105 | 0.01% to 1.00% | 0.01% | 3 |
| Pluronic ® P123 | 0.001% to 0.1% | 0.01% | 2 |
| Pluronic ® L31 | 0.001% to 0.1% | 0.05% | 4 |
| Pluronic ® L43 | 0.001% to 1.00% | 0.10% | 2 |
| Pluronic ® L44 | 0.001% to 1.00% | 0.001% | 5 |
| Pluronic ® L61 | 0.001% to 0.1% | 0.01% | 6 |
| Pluronic ® L62 | 0.001% to 1.00% | 0.01% | 6 |
| Pluronic ® L64 | 0.001% to 1.00% | 0.01% | 5 |
| Pluronic ® L81 | 0.001% to 1.00% | 0.01% | 3 |
| Pluronic ® L92 | 0.001% to 1.00% | 0.05% | 5 |
| Pluronic ® L101 | 0.001% to 1.00% | 0.001% | 5 |
| Pluronic ® L121 | 0.001% to 1.00% | 0.10% | 3 |
| Pluronic ® R 17R4 | 0.002% to 1.00% | 0.10% | 5 |
| Pluronic ® R 25R4 | 0.001% to 0.05% | 0.01% | 5 |
| Pluronic ® R 25R2 | 0.002% to 1.00% | 0.01% | 7 |

TABLE VI

| Auxiliary agents tested | Concentrations tested | Optimal Concentration | FOLD x NaP |
|---|---|---|---|
| Actin | 0.2 to 1.0 mg/ml | 0.2 mg/ml % | 1.11 |
| BRIG 35 | 0.001% to 0.1% | 0.01% | 1.53 |
| CHAPS | 0.001% to 0.1% | 0.001% | 1.07 |
| DMSO | 0.001% to 0.1% | 0.001% | 1.66 |
| EDTA | 0.01 mM to 1 mM | 0.01 mM | 1.55 |
| EGTA | 1 mM to 10 mM | 1 mM | 0.05 |
| Lecithin | 0.001% to 0.01% | 0.001% | 1.15 |
| MEGA 7 | 0.01% to 0.1% | 0.01% | 1.20 |
| MEGA 8 | 0.01% to 0.1% | 0.01% | 1.09 |
| MEGA 9 | 0.01% to 0.1% | 0.01% | 1.08 |
| MYRJ 52 | 0.001% to 0.1% | 0.10% | 0.59 |
| MYRJ 53 | 0.001% to 0.1% | 0.01% | 0.80 |
| n-Dodecylmaltoside | 0.005% to 0.05% | 0.005% | 1.18 |
| n-octylglucoside | 0.005% to 0.1% | 0.005% | 2.21 |
| NP-40 | 0.001% to 1% | 0.01% | 2.72 |
| PEG 8000 | 1% to 4% | 3.00% | 1.51 |
| Polyoxyethylene 10 cetyl ether | 0.005% to 0.1% | 0.01% | 1.18 |
| Polyoxyethylene 20 stearyl ether | 0.005% to 0.1% | 0.01% | 1.50 |
| Propanediol | 0.01% to 0.2% | 0.20% | 0.99 |
| Saponin | 0.005% to 0.1% | 0.01% | 0.01 |
| SDS | 0.001% to 0.01% | 0.001% | 1.59 |
| Sorbitan monooleate | 0.005% to 0.2% | 0.20% | 1.29 |
| SPAN 20 | 0.001% to 0.1% | 0.01% | 1.00 |
| Stachyose | 10 mM to 600 mM | 100 mM | 2.32 |
| Surfactin | 0.001% to 0.10% | 0.00% | 0.79 |
| Tergitol | 0.005% to 0.10% | 0.01% | 1.81 |
| Thesit | 0.005% to 0.1% | 0.01% | 2.40 |
| Triton X-100 | 0.001% to 2% | 0.01% | 2.60 |
| Triton X-114 | 0.005% to 0.01% | 0.01% | 2.21 |
| Triton-x-N60 | 0.005% to 0.05% | 0.01% | 0.97 |
| Tween 20 | 0.001% to 0.5% | 0.10% | 1.92 |
| Tween 80 | 0.0001 to 0.5% | 0.10% | 1.77 |
| Zwittergent | 0.005% to 0.05% | 0.01% | 1.44 |

What is claimed is:

1. A method for expressing a polypeptide in a vertebrate, comprising administering into a tissue or cavity of said vertebrate a composition comprising:

(a) about 1 ng to about 30 mg of a polynucleotide in aqueous solution, wherein the polynucleotide expresses a polypeptide upon delivery to vertebrate cells in vivo;

(b) a salt M-X dissolved in said aqueous solution at a molar concentration ranging from about 50 mM to about 250 mM, and reaction, association, and dissociation products thereof, wherein M is a cation selected from the group consisting of sodium and potassium, wherein X is an anion selected from the group consisting of phosphate, acetate, bicarbonate, sulfate, and pyruvate; and (c) an auxiliary agent selected from the group consisting of a poloxamer and a reverse poloxamer;

wherein said aqueous solution contains chloride ion at a molar concentration ranging from 0 mM to about 50 mM, and wherein said polypeptide is expressed in the vertebrate in an amount sufficient to be detectable.

2. The method of claim 1, wherein the auxiliary agent is a poloxamer.

3. The method of claim 1, wherein the auxiliary agent is a reverse poloxamer.

4. The method of claim 2, wherein the poloxamer has a molecular weight from 1000 grams per mole to greater than 16000 grams per mole.

5. The method of claim 2, wherein the poloxamer has an approximate hydrophobe molecular weight from 900 grams per mole to 3600 grams per mole and an approximate hydrophile weight percentage of 10% to 80%.

6. The method of claim 3, wherein the reverse poloxamer has an approximate hydrophobe molecular weight of 1000 grams per mole to 3100 grams per mole and an approximate hydrophile weight percentage of 10% to 80%.

7. The method of claim 6, wherein the reverse poloxamer has an approximate hydrophobe molecular weight of about 2500 grams per mole and an approximate hydrophile weight percentage of about 20%.

8. The method of claim 2, wherein the poloxamer is selected from the group consisting of a poloxamer having an approximate hydrophobe molecular weight of 1800 grams per mole and an approximate hydrophile weight percentage of 80%; a poloxamer having an approximate hydrophobe molecular weight of 2100 grams per mole and an approximate hydrophile weight percentage of 70%; a poloxamer having an approximate hydrophobe molecular weight of 3000 grams per mole and an approximate hydrophile weight percentage of 80%; a poloxamer having an approximate hydrophobe molecular weight of 2400 grams per mole and an approximate hydrophile weight percentage of 40%; a poloxamer having an approximate hydrophobe molecular weight of 1200 grams per mole and an approximate hydrophile weight percentage of 40%; a poloxamer having an approximate hydrophobe molecular weight of 1800 grams per mole and an approximate hydrophile weight percentage of 20%; and a poloxamer having an approximate hydrophobe molecular weight of 1800 grams per mole and an approximate hydrophile weight percentage of 40%.

9. The method of claim 3, wherein the reverse poloxamer is selected from the group consisting of a reverse poloxamer having an approximate hydrophobe molecular weight of 1700 grams per mole and an approximate hydrophile weight percentage of 40%; a reverse poloxamer having an approximate hydrophobe molecular weight of 2500 grams per mole and an approximate hydrophile weight percentage of 40%; and a reverse poloxamer having an approximate hydrophobe molecular weight of 2500 grams per mole and an approximate hydrophile weight percentage of 20%.

10. The method of claim 9, wherein the reverse poloxamer has an approximate hydrophobe molecular weight of 2500 grams per mole and an approximate hydrophile weight percentage of 20%.

11. The method of claim 1, wherein the auxiliary agent is selected from the group consisting of about 0.1% (w/v) to about 6.0% (w/v) of a poloxamer having an approximate hydrophobe molecular weight of 1800 grams per mole and an approximate hydrophile weight percentage of 80%; about 0.001% (w/v) to about 2.0% (w/v) of a poloxamer having an approximate hydrophobe molecular weight of 2100 grams per mole and an approximate hydrophile weight percentage of 70%; and about 0.01% (w/v) to about 1% (w/v) of a poloxamer having an approximate hydrophobe molecular weight of 1800 grams per mole and an approximate hydrophile weight percentage of 50%.

12. The method of claim 3, wherein the reverse poloxamer has an approximate hydrophobe molecular weight of 2500 grams per mole and an approximate hydrophile weight percentage of 20% and is present in the composition in a concentration of about 0.001% (w/v) to about 1.0% (w/v).

13. The method of claim 1, wherein the auxiliary agent is selected from the group consisting of about 0.5% to about 4.0% (w/v) of a poloxamer having an approximate hydrophobe molecular weight of 1800 grams per mole and an approximate hydrophile weight percentage of 80%; about 0.1% (w/v) to about 1.7% (w/v) of a poloxamer having an approximate hydrophobe molecular weight of 2100 grams per mole and an approximate hydrophile weight percentage of 70%; and about 0.01% (w/v) to about 0.5% (w/v) of a poloxamer having an approximate hydrophobe molecular weight of 1800 grams per mole and an approximate hydrophile weight percentage of 40%.

14. The method of claim 1, wherein the auxiliary agent is selected from the group consisting of 4%(w/v) of a poloxamer having an approximate hydrophobe molecular weight of 1800 grams per mole and an approximate hydrophile weight percentage of 80%, 1.0% (w/v) of a poloxamer having an approximate hydrophobe molecular weight of 2100 grams per mole and an approximate hydrophile weight percentage of 70%; and 0.5% (w/v) of a poloxamer having an approximate hydrophobe molecular weight of 1800 grams per mole and an approximate hydrophile weight percentage of 50%.

15. The method of claim 2, wherein the poloxamer is selected from the group consisting of a poloxamer having an approximate hydrophobe molecular weight of 1800 grams per mole and an approximate hydrophile weight percentage of 50%; a poloxamer having an approximate hydrophobe molecular weight of 3000 grams per mole and an approximate hydrophile weight percentage of 30%; a poloxamer having an approximate hydrophobe molecular weight of 3000 grams per mole and an approximate hydrophile weight percentage of 40%; a poloxamer having an approximate hydrophobe molecular weight of 3000 grams per mole and an approximate hydrophile weight percentage of 50%; a poloxamer having an approximate hydrophobe molecular weight of 3600 grams per mole and an approximate hydrophile weight percentage of 30%; a poloxamer having an approximate hydrophobe molecular weight of 900 grams per mole and an approximate hydrophile weight percentage of 10%; a poloxamer having an approximate hydrophobe molecular weight of 1200 grams per mole and an approximate hydrophile weight percentage of 30%; a poloxamer having an approximate hydrophobe molecular weight of 1800 grams per mole and an approximate hydrophile weight percentage of 10%; a poloxamer having an approximate hydrophobe molecular weight of 2400 grams per mole and an approximate hydrophile weight percentage of 10%; a poloxamer having an approximate hydrophobe molecular weight of 2700 grams per mole and an approximate hydrophile weight percentage of 20%; a poloxamer having an approximate hydrophobe molecular weight of 3000 grams per mole and an approximate hydrophile weight percentage of 10%; and a poloxamer having an approximate hydrophobe molecular weight of 3600 grams per mole and an approximate hydrophile weight percentage of 10%.

16. The method of claim 1, wherein the auxiliary agent is selected from the group consisting of about 0.01% (w/v) to about 1.0% (w/v) of a poloxamer having an approximate hydrophobe molecular weight of 3000 grams per mole and an approximate hydrophile weight percentage of 80%; about 0.01% (w/v) to about 1.0% (w/v) of a poloxamer having an approximate hydrophobe molecular weight of 3000 grams per mole and an approximate hydrophile weight percentage of 30%; about 0.0005% (w/v) to about 1.0% (w/v) of a poloxamer having an approximate hydrophobe molecular weight of 1200 grams per mole and an approximate hydrophile weight percentage of 40%; about 0.01% (w/v) to about 1.0% (w/v) of a poloxamer having an approximate hydrophobe molecular weight of 1800 grams per mole and an approximate hydrophile weight percentage of 40%; about 0.002% (w/v) to about 1.0% (w/v) of a reverse poloxamer having an approximate hydrophobe molecular weight of 1700 grams per mole and an approximate hydrophile weight percentage of 40%; about 0.002% (w/v) to about 1.0% (w/v) of a reverse poloxamer having an approximate hydrophobe molecular weight of 2500 grams per mole and an approximate hydrophile weight percentage of 40%; and about 0.001% (w/v) to about 1.0% (w/v) of a reverse poloxamer having an approximate hydrophobe molecular weight of 2500 grams per mole and an approximate hydrophile weight percentage of 20%.

17. The method of claim 1, wherein the auxiliary agent is selected from the group consisting of about 0.05% (w/v) to about 0.5% (w/v) of a poloxamer having an approximate hydrophobe molecular weight of 3000 grams per mole and an approximate hydrophile weight percentage of 80%; about 0.1% (w/v) to about 1% (w/v) of a poloxamer having an approximate hydrophobe molecular weight of 1800 grams per mole and an approximate hydrophile weight percentage of 50%; about 0.001% (w/v) to about 0.10% (w/v) of a poloxamer having an approximate hydrophobe molecular weight of 1200 grams per mole and an approximate hydrophile weight percentage of 40%; about 0.01% (w/v) to about 0.10% (w/v) of a reverse poloxamer having an approximate hydrophobe molecular weight of 1700 grams per mole and an approximate hydrophile weight percentage of 40%; about 0.0 1% (w/v) to about 0.10% (w/v) of a reverse poloxamer having an approximate hydrophobe molecular weight of 2500 grams per mole and an approximate hydrophile weight percentage of 40%; and about 0.001% (w/v) to about 0.1% (w/v) of a reverse poloxamer having an approximate hydrophobe molecular weight of 2500 grams per mole and an approximate hydrophile weight percentage of 20%.

18. The method of claim 17, wherein the auxiliary agent is about 0.00 1% (w/v) to about 0.1% (w/v) of a reverse poloxamer having an approximate hydrophobe molecular weight of 2500 grams per mole and an approximate hydrophile weight percentage of 20%.

19. The method of claim 1, wherein the auxiliary agent is selected from the group consisting of 0.1% (w/v) of a poloxamer having an approximate hydrophobe molecular weight of 3000 grams per mole and an approximate hydrophile weight percentage of 80%; 0.05% (w/v) of a poloxamer having an approximate hydrophobe molecular weight of 3000 grams per mole and an approximate hydrophile weight percentage of 30%; 0.001% (w/v) of a poloxamer having an approximate hydrophobe molecular weight of 1200 grams per mole and an approximate hydrophile weight percentage of 40%; about 0.01% (w/v) to about 0.1% (w/v) of a poloxamer having an approximate hydrophobe molecular weight of 1800 grams per mole and an approximate hydrophile weight percentage of 40%; 0.10% (w/v) of a reverse poloxamer having an approximate hydrophobe molecular weight of 1700 grams per mole and an approximate hydrophile weight percentage of 40%; 0.01% (w/v) of a reverse poloxamer having an approximate hydrophobe molecular weight of 2500 grams per mole and an approximate hydrophile weight percentage of 40%; and 0.01% (w/v) of a reverse poloxamer having an approximate hydrophobe molecular weight of 2500 grams per mole and an approximate hydrophile weight percentage of 20%.

20. The method of claim 19, wherein the auxiliary agent is 0.01% (w/v) of a reverse poloxamer having an approximate hydrophobe molecular weight of 2500 grams per mole and an approximate hydrophile weight percentage of 20%.

21. The method of claim 1, wherein the auxiliary agent is selected from the group consisting of about 0.001% (w/v) to about 0.1% (w/v) of a poloxamer having an approximate hydrophobe molecular weight of 900 grams per mole and an approximate hydrophile weight percentage of 10%; about 0.001% (w/v) to about 0.1% (w/v) of a poloxamer having an approximate hydrophobe molecular weight of 1800 grams per mole and an approximate hydrophile weight percentage of 10%; and about 0.001% (w/v) to about 1.0% (w/v) of a poloxamer having an approximate hydrophobe molecular weight of 2700 grams per mole and an approximate hydrophile weight percentage of 20%.

22. The method of claim 1, wherein the auxiliary agent is selected from the group consisting of 0.05% (w/v) of a poloxamer having an approximate hydrophobe molecular weight of 900 grams per mole and an approximate hydrophile weight percentage of 10%; 0.0 1% (w/v) of a poloxamer having an approximate hydrophobe molecular weight of 1800 grams per mole and an approximate hydrophile weight percentage of 10%; and 0.05% (w/v) of a poloxamer having an approximate hydrophobe molecular weight of 2700 grams per mole and an approximate hydrophile weight percentage of 20%.

23. The method of claim 1, wherein M is selected from the group consisting of sodium and potassium, and wherein X is selected from the group consisting of phosphate, acetate, and bicarbonate.

24. The method of claim 23, wherein said salt is sodium phosphate or potassium phosphate.

25. The method of claim 1, wherein salt is dissolved in said aqueous solution at a concentration ranging from about 100 mM to 200 mM.

26. The method of claim 1, wherein said salt is dissolved in said aqueous solution at a concentration of about 150 mM.

27. The method of claim 1, wherein said aqueous solution contains chloride ion at a molar concentration ranging from 0mM to about 30 mM.

28. The method of claim 1, wherein said aqueous solution contains chloride ion at a molar concentration ranging from 0 mM to about 15 mM.

29. The method of claim 1, wherein said aqueous solution contains chloride ion at a molar concentration ranging from 0 mM to about 5 mM.

30. The method of claim 1, wherein said polynucleotide is DNA operably associated with a promoter.

31. The method of claim 30, wherein said polynucleotide is contained on a plasmid.

32. The method of claim 1, wherein said polynucleotide is RNA.

33. The method of claim 32, wherein said polynucleotide is contained in messenger RNA.

34. The method of claim 1, wherein said polypeptide is selected from the group consisting of a therapeutic polypeptide, an antigenic polypeptide, an immunogenic polypeptide, an immunomodulatory polypeptide, and a functional self polypeptide.

35. The method of claim 34, wherein said therapeutic polypeptide is selected from the group consisting of granulocyte macrophage colony stimulating factor, granulocyte colony stimulating factor, macrophage colony stimulating factor colony stimulating factor, interleukin 2, interleukin-3, interleukin 4, interleukin 5, interleukin 6, interleukin 7, interleukin 8, interleukin 10, interleukin 12, interleukin 15, interleukin 18, interferon alpha, interferon beta, interferon gamma, interferon omega, interferon tau, interferon gamma inducing factor I, transforming growth factor beta, RANTES, macrophage inflammatory proteins, Leishmania elongation initiating factor, platelet derived growth factor, tumor necrosis factor, epidermal growth factor, vascular epithelial growth factor, fibroblast growth factor, nerve growth factor, brain derived neurotrophic factor, neurotrophin-2, neurotrophin-3, neurotrophin-4, neurotrophin-5, glial cell line-derived neurotrophic factor, ciliary neurotrophic factor, erythropoietin, insulin, and therapeutically active fragments thereof.

36. The method of claim 34, wherein said immunogenic polypeptide is selected from the group consisting of a bacterial polypeptide, a viral polypeptide, a fungal polypeptide, a parasite polypeptide, an allergen, a tumor specific polypeptide, and immunogenic fragments thereof.

37. The method of claim 34, wherein said immunomodulatory polypeptide is selected from the group consisting of a cytokine, a chemokine, and immunomodulatory fragments thereof.

38. The method of claim 34, wherein said functional self polypeptide is selected from the group consisting of insulin, dystrophin, cystic fibrosis transmembrane conductance regulator, granulocyte macrophage colony stimulating factor, granulocyte colony stimulating factor, macrophage colony stimulating factor colony stimulating factor, interleukin 2, interleukin-3, interleukin 4, interleukin 5, interleukin 6, interleukin 7, interleukin 8, interleukin 10, interleukin 12, interleukin 15, interleukin 18, interferon alpha, interferon beta, interferon gamma, interferon omega, interferon tau, interferon gamma inducing factor I, transforming growth factor beta, RANTES, macrophage inflammatory proteins, platelet derived growth factor, tumor necrosis factor, epidermal growth factor, vascular epithelial growth factor, fibroblast growth factor, nerve growth factor, brain derived neurotrophic factor, neurotrophin-2, neurotrophin-3, neurotrophin-4, neurotrophin-5, glial cell line-derived neurotrophic factor, ciliary neurotrophic factor, erythropoietin, and therapeutically active fragments thereof.

39. The method of claim 1, further comprising a transfection facilitating agent selected from the group consisting of cationic lipids, calcium phosphate, alum, gold, tungsten, or other metal particles, transfection facilitating peptides, transfection facilitating proteins, and transfection facilitating polymers.

40. The method of claim 39, wherein said transfection facilitating agent is a cationic lipid.

41. The method of claim 1, wherein said vertebrate is a mammal.

42. The method of claim 41, wherein said mammal is a human.

43. The method of claim 1, wherein said tissue is selected from the group consisting of muscle, skin, brain tissue, lung tissue, liver tissue, spleen tissue, bone marrow tissue, thymus tissue, heart tissue, lymph tissue, blood tissue, bone tissue, connective tissue, mucosal tissue, pancreas tissue, kidney tissue, gall bladder tissue, intestinal tissue, testicular tissue, ovarian tissue, uterine tissue, vaginal tissue, rectal tissue, nervous system tissue, eye tissue, glandular tissue, and tongue tissue.

44. The method of claim 1, wherein said cavity is selected from the group consisting of the lungs, the mouth, the nasal cavity, the stomach, the peritoneal cavity, the intestine, a heart chamber, veins, arteries, capillaries, lymphatic cavities, the uterine cavity, the vaginal cavity, the rectal cavity, joint cavities, ventricles in brain, spinal canal, and the ocular cavities.

45. The method of claim 1, wherein said cavity comprises a mucosal surface.

46. The method of claim 45 wherein said mucosal surface is lung tissue.

47. The method of claim 43, wherein said tissue is muscle.

48. The method of claim 47, wherein said tissue is skeletal muscle, smooth muscle, or myocardium.

49. The method of claim 1, wherein said administration is by a route selected from the group consisting of intramuscular, intravenous, intratracheal, intranasal, transdermal, interdermal, subcutaneous, intraocular, vaginal, rectal, intraperitoneal, intraintestinal and inhalation.

50. The method of claim 1, wherein said administration route is intravenous.

51. The method of claim 1, wherein said administration route is intramuscular.

52. The method of claim 51, wherein said administration is by intramuscular injection.

53. The method of claim 1, wherein said administration is mediated by a catheter.

54. A composition for delivering a polypeptide into a vertebrate, comprising:
    (a) about 1 ng to about 30 mg of a polynucleotide in aqueous solution, wherein the polynucleotide expresses a polypeptide upon delivery to vertebrate cells in vivo;
    (b) a salt M-X dissolved in said aqueous solution at a molar concentration ranging from about 50 mM to about 250 mM, and reaction, association, and dissociation products thereof, wherein M is a cation selected from the group consisting of sodium and potassium, wherein X is an anion selected from the group consisting of phosphate, acetate, sulfate, and pyruvate; and
    (c) an auxiliary agent selected from the group consisting of a poloxamer and a reverse poloxamer;
    wherein said aqueous solution contains chloride ion at a molar concentration ranging from 0 mM to about 50 mM, and wherein said polypeptide is expressed in the vertebrate in an amount sufficient to be detectable.

55. The composition of claim 54, wherein said salt is dissolved in said aqueous solution at a concentration ranging from about 100 mM to 200 mM.

56. The composition of claim 54, wherein said salt is dissolved in said aqueous solution at a concentration of about 150 mM.

57. The composition of claim 54, wherein X of said salt is phosphate.

58. The composition of claim 54, wherein said aqueous solution contains chloride ion at a molar concentration ranging from 0 mM to about 30 mM.

59. The composition of claim 54, wherein said aqueous solution contains chloride ion at a molar concentration ranging from 0 mM to about 15 mM.

60. The composition of claim 54, wherein said aqueous solution contains chloride ion at a molar concentration ranging from 0 mM to about 5 mM.

* * * * *